US011232851B2

(12) United States Patent
Yang et al.

(10) Patent No.: US 11,232,851 B2
(45) Date of Patent: Jan. 25, 2022

(54) SYSTEM AND METHOD FOR MODELING AND SUBTRACTING BACKGROUND SIGNALS FROM A MELT CURVE

(71) Applicant: Canon U.S. Life Sciences, Inc., Rockville, MD (US)

(72) Inventors: Yang Yang, Sunnyvale, CA (US); Sophie Paquerault, Rockville, MD (US); Bradley Scott Denney, Irvine, CA (US); Lance Charlton, Rancho Santa Margarita, CA (US); Jeanette Paek, Los Alamitos, CA (US); Attaullah Seikh, Irvine, CA (US); Vyshnnavi Parthasarathy, Irvine, CA (US); Ken Pearson, Buena Park, CA (US); Hung Huang, Irvine, CA (US); Tejinder Uppal, Orange, CA (US)

(73) Assignee: Canon Information and Imaging Solutions, Inc., Melville, NY (US)

( * ) Notice: Subject to any disclaimer, the term of this patent is extended or adjusted under 35 U.S.C. 154(b) by 1071 days.

(21) Appl. No.: 15/631,832

(22) Filed: Jun. 23, 2017

(65) Prior Publication Data

US 2017/0372002 A1 Dec. 28, 2017

Related U.S. Application Data

(60) Provisional application No. 62/353,608, filed on Jun. 23, 2016, provisional application No. 62/511,076, filed on May 25, 2017, provisional application No. 62/511,070, filed on May 25, 2017, provisional application No. 62/511,057, filed on May 25, 2017, provisional application No. 62/511,064, filed on May 25, 2017, provisional application No. 62/353,602, filed on Jun. 23, 2016, provisional application No. 62/353,623, filed on Jun. 23, 2016, provisional application No. 62/353,615, filed on Jun. 23, 2016, provisional application No. 62/403,422, filed on Oct. 3, 2016.

(51) Int. Cl.
| | |
|---|---|
| G16B 25/00 | (2019.01) |
| G01N 25/04 | (2006.01) |
| C12Q 1/68 | (2018.01) |
| G01N 35/00 | (2006.01) |
| G16B 45/00 | (2019.01) |
| G16B 50/00 | (2019.01) |
| G01N 25/48 | (2006.01) |
| G16B 25/20 | (2019.01) |
| G16B 5/30 | (2019.01) |
| B01L 3/00 | (2006.01) |
| C12Q 1/6851 | (2018.01) |

(52) U.S. Cl.
CPC ............... *G16B 25/00* (2019.02); *C12Q 1/68* (2013.01); *G01N 25/04* (2013.01); *G01N 25/4846* (2013.01); *G01N 35/00029* (2013.01); *G01N 35/00871* (2013.01); *G16B 5/30* (2019.02); *G16B 25/20* (2019.02); *G16B 45/00* (2019.02); *G16B 50/00* (2019.02); *B01L 3/5027* (2013.01); *B01L 2300/02* (2013.01); *B01L 2300/023* (2013.01); *B01L 2300/0654* (2013.01); *B01L 2300/0829* (2013.01); *B01L 2300/18* (2013.01); *C12Q 1/6851* (2013.01); *G01N 2035/0091* (2013.01); *G01N 2035/00148* (2013.01); *G01N 2035/00366* (2013.01); *G01N 2035/00881* (2013.01)

(58) Field of Classification Search
None
See application file for complete search history.

(56) References Cited

U.S. PATENT DOCUMENTS

| | | | |
|---|---|---|---|
| 8,068,992 B2 | 11/2011 | Palais et al. | |
| 8,145,433 B2 | 3/2012 | Boles et al. | |
| 8,219,326 B2 | 7/2012 | Kurnik | |
| 8,483,972 B2 | 7/2013 | Kanderian et al. | |
| 8,538,733 B2 | 9/2013 | Cheng et al. | |
| 8,606,527 B2 | 12/2013 | Houser | |
| 8,980,556 B2 | 3/2015 | Buettner et al. | |
| 2011/0238323 A1 | 9/2011 | Robbins et al. | |
| 2012/0101740 A1 | 4/2012 | Orpana et al. | |
| 2014/0272927 A1 | 9/2014 | Coursey et al. | |
| 2014/0343862 A1 | 11/2014 | Cheng | |

OTHER PUBLICATIONS

Dwight et al.: "uMELT: prediction of high-resolution melting curves and dynamic melting profiles of PCR products in a rich web application," Bioinformatics Applications Note, vol. 27 No. 7 2011, pp. 1019-1020.

Nellåker: "Mixture models for analysis of melting temperature data," BMC Bioinformatics 2008, 9:370.

*Primary Examiner* — G Steven Vanni
(74) *Attorney, Agent, or Firm* — Canon U.S.A., Inc., IP Division

(57) ABSTRACT

The present invention relates to methods for the analysis of nucleic acids present in biological samples, and more specifically to normalize a high resolution melt curve to assist in the identification of one or more properties of the nucleic acids. The present invention provides methods and systems that incorporate a background identification algorithm according to invention principles using raw melt curve data to identify reactions that are unrelated actual DNA melt reactions. Furthermore, a web-based application for analyzing experimental data is provided. The raw experimental data obtained from a variety of instruments is processed and analyzed on a server and presented to a user through a user interface (UI).

12 Claims, 52 Drawing Sheets
(16 of 52 Drawing Sheet(s) Filed in Color)

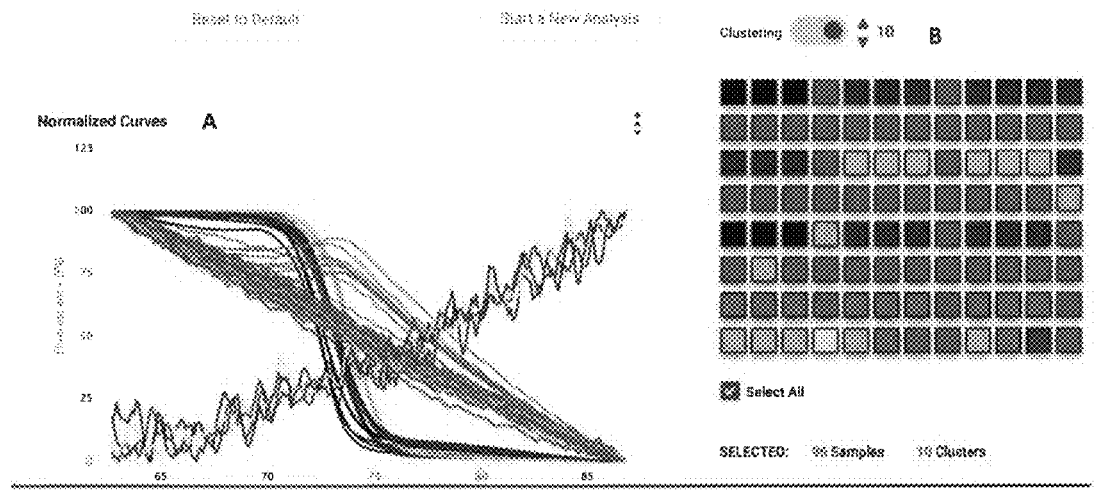
FIGs. 53A-B
FIGs. 54A-B

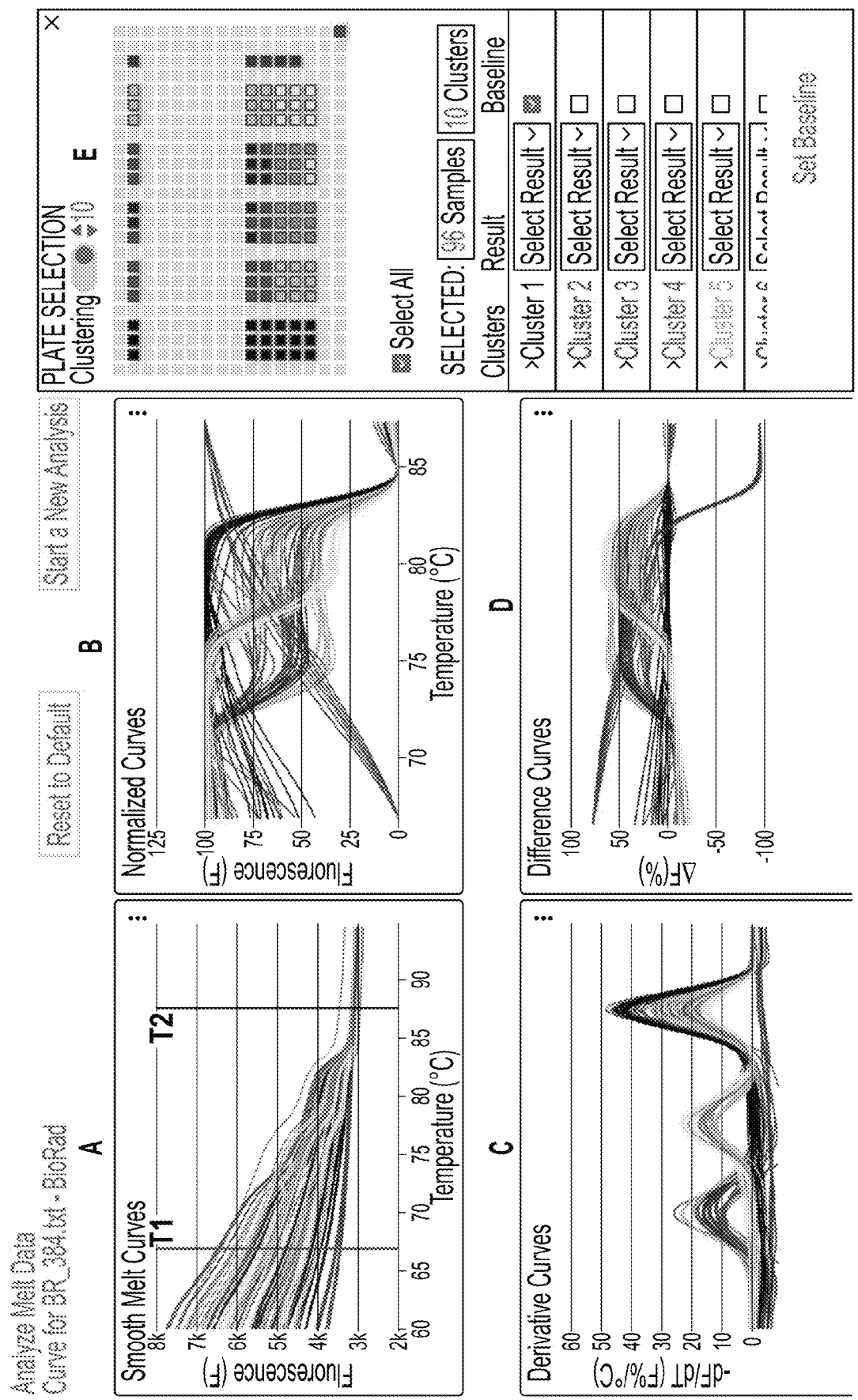
FIG. 55A-E

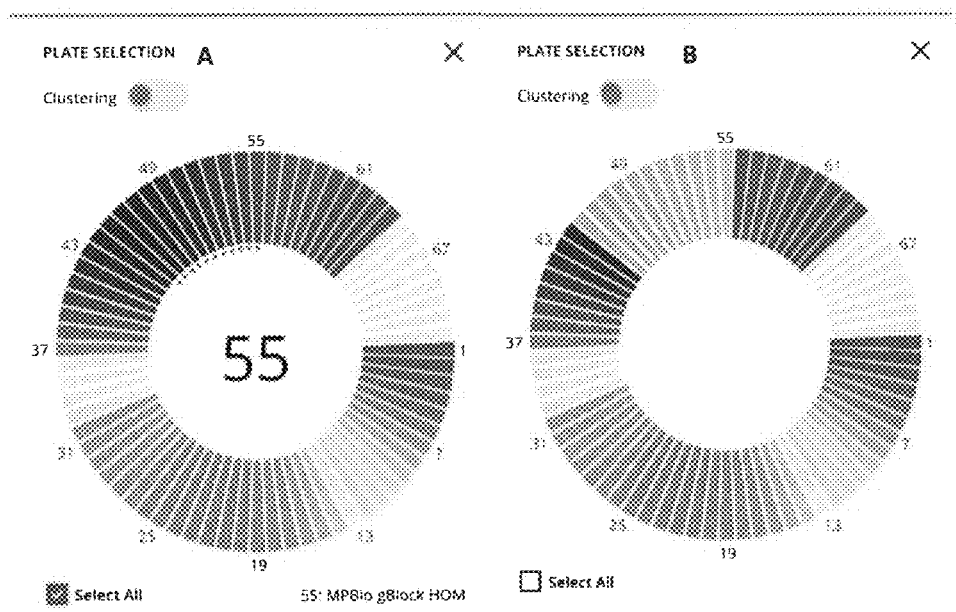
FIGs. 57A-B
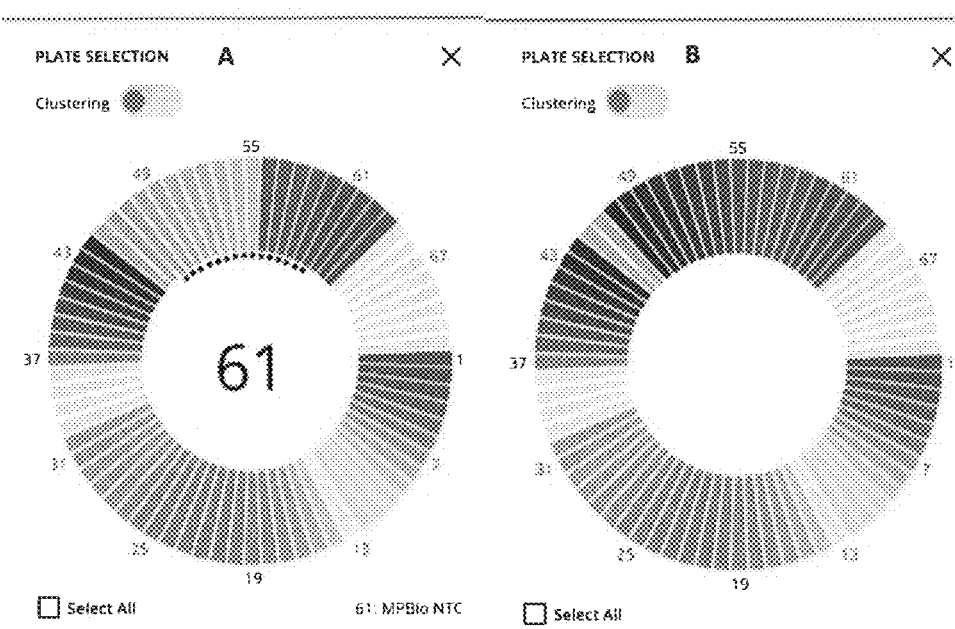
FIGs. 58A-B

SYSTEM AND METHOD FOR MODELING AND SUBTRACTING BACKGROUND SIGNALS FROM A MELT CURVE

CLAIM OF PRIORITY AND INCORPORATION BY REFERENCE

This application claims the benefit of priority to U.S. Provisional Patent Application Ser. Nos. 62/511,076 filed May 25, 2017, 62/511,070 filed May 25, 2017, 62/511,064 filed May 25, 2017, 62/511,057 filed May 25, 2017, 62/353,608, filed on Jun. 23, 2016, 62/353,623 filed Jun. 23, 2016, 62/353,615 filed Jun. 23, 2016 and 62/353,602 filed Jun. 23, 2016, which are incorporated herein by reference in their entirety. Furthermore, this application references and makes use of various techniques and features described in the following US patents and patent applications: U.S. Pat. No. 8,483,972, currently pending U.S. patent application Ser. No. 13/937,522 which is a continuation of the '972 patent, U.S. Pat. Nos. 8,145,433, 8,606,529, 8,180,572, and 9,292,653. Reference is also made to U.S. patent application Ser. No. 15/631,794 filed concurrent herewith on Jun. 23, 2017. Each of the above referenced US patents and pending patent applications are incorporated herein by reference in their entireties.

BACKGROUND

Field of the Invention

The present invention relates to methods for the analysis of nucleic acids present in biological samples, and more specifically to normalize a high resolution melt curve to assist in the identification of one or more properties of the nucleic acids.

Description of Related Art

The detection and identification of nucleic acids is central to medicine, forensic science, industrial processing, crop and animal breeding, and many other fields. A number of high throughput approaches to performing polymerase chain reactions (PCR) and other amplification reactions to identify and detect characteristics of nucleic acids have been developed. One example involves amplification reactions in microfluidic devices, as well as methods for detecting and analyzing amplified nucleic acids in or on the devices. These devices enable further characterization of the amplified DNA molecules contained therein. One method of characterizing the DNA is to examine the DNA's dissociation behavior as the DNA transitions from double stranded DNA (dsDNA) to single stranded DNA (ssDNA). The process of causing DNA to transition from dsDNA to ssDNA with increasing temperature is sometimes referred to as a "high-resolution temperature (thermal) melt (HRTm)" process, or simply a "high-resolution melt" process.

Melting profile analysis enables characterization of nucleic acids, e.g. genotyping or determination whether a mutation is present or absent. A sample melting profile is usually obtained by denaturing double stranded nucleic acids into single stranded nucleic acids. To monitor the sample melt, a fluorescent dye that indicates whether the two DNA strands are bound or not is used. Examples of such indicator dyes include non-specific binding dyes such as SYBR® Green I, whose fluorescence efficiency depends strongly on whether the DNA is double stranded or single stranded. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence.

Some nucleic acid assays have been designed so that it permits differentiation between different genotypes. Generally, for thermal melt analysis, a simple visual inspection of a thermal melt profile allows determination of the melting temperature of the nucleic acid in the sample. However, this inspection task may be challenging for some nucleic acid assays that have been designed for the identification of a single nucleotide change where the difference in melting temperature ($T_m$) between the wild type nucleic acid and a mutant nucleic acid is quite small (e.g. less than 0.25° C.). A sample melting curve is generally presented with the fluorescence information on the Y-axis versus the temperature on the X-axis. The negative derivative of melting curve is also frequently derived since providing an ease of determination of the sample characteristic (i.e., genotyping), knowing that each potential genotype is revealed by a unique signature or curve profile. The determination of a sample genotype is usually performed by visually comparing its melting profile with that of reference or baseline samples which genotypes are known. Examples of genotyping classification include identifying the genotype as homozygous wildtype (WT), heterozygous (HET) or homozygous mutant (HOM) depending on the alleles that make up the DNA.

A melting curve of a DNA sequence is obtained by measuring the amount of double-stranded DNA in the sample while the temperature of the product is sequentially increased. In exemplary operation, an amount of double-stranded DNA contained in a biological sample may be obtained during melt processing by measuring a fluorescence level of a dye bounded to double-stranded DNA during the Polymerase Chain Reaction (PCR)/amplification process which precedes the melt processing. The dye molecules bound to the double stranded DNA are actively fluorescing (e.g. emitting detectable light signatures) on the doubled-stranded DNA (dsDNA) and become inactive when the double stranded DNA or portions thereof are denatured into single-stranded DNA (ssDNA). The shape and relative position on the temperature scale of the resulting melting curve provides critical information relative to either the DNA type, or presence or absence of a mutation.

DNA melting curves generated on any existing instrument are typically not normalized on the fluorescence scale. The melt curves generated include not only information associated with the DNA, but also information associated on the remaining unused primers, dyes, and other reagents or instrumental component interaction that are necessary for the PCR/amplification of the DNA sample. FIG. 1 depicts an exemplary melt curve 10 along with a non-template control (NTC) curve 11. The melt curve 10 of FIG. 1 illustrates two types of regions based on the slope of the curve. A first type of region 12 having a slow downward slope is present at low and high temperatures is mostly produced by the melt of the remaining unused primers and other reagents in the product. A second type of region 14, shown here between the lines in the central region of the curve presenting a rapid downward slope is mostly revealing the DNA melt component.

Numerous methods have been suggested for identification of background information and subtraction of the background information from a sample melting curve. These methods are often referred as melting curve normalization methods. Conventional curve analysis and workflow are performed so that underlying genotyping of each sample curve be decided upon either in a manual or semi-manual manner. This may typically include a step of normalization followed by a step of comparing/differentiating pairs of melting curves, using either a baseline or well-known reference curve, or simply all possible pairs of melting curves generated for a plate or cartridge. It is sometimes beneficial for the normalization step to determine a melt region in melting curves. Accordingly, there is a need for an algorithm that allows for automatically determining start and end temperatures defining the melt region. After a differentiation step is performed, a classification step follows which assigns a given sample to a certain genotype or classify the sample as having a mutation or not. Furthermore, there is a need for interactive melting curve analysis involving computational operations over a cloud based web application.

SUMMARY OF THE INVENTION

According to one aspect of the invention, a first method and system for removing a background signal from a DNA melting curve is provided. Specifically, a device having at least one DNA sample is in communication with a thermal system that is continuously increasing the temperature of the at least one DNA sample to cause a DNA melting reaction resulting in denaturing dsDNA to ssDNA.

A controller in communication with the device and the thermal system provides instruction for generating a melting curve F(T) for a DNA sample, wherein F is a fluorescence signal indicative of a DNA denaturation process and T is the temperature of the DNA sample. Next, a mathematical model is fitted by the controller to the melting curve F(T). In one embodiment, the mathematical model is represented by a sum of a background reaction term and at least one DNA melting reaction term. Each DNA melting reaction term is indicative of the DNA denaturation process and the background reaction term is indicative of the background signal.

The mathematical model is fitted to the melting curve by calculating model parameters for a model curve. Then, a maximum difference between the melting curve derivative dF(T)/dT and the model derivative curve is estimated along with the temperature corresponding to the maximum difference. A DNA melting reaction term is iteratively added to the sum representing the mathematical model and the sum is refitted to the melting curve F(T) to recalculate all model parameters in response to the difference between the melting curve derivative and the model curve derivative being greater than a threshold. An initial temperature parameter for each newly added DNA melting reaction term is selected to be equal to the temperature corresponding to the maximum difference between the melting curve and the model curve derivative.

The iteration process is stopped when the difference between the melting curve and the model curve derivative is less than the threshold. The background reaction term having parameters estimated in the last iteration step is subtracted from the melting curve F(T).

In yet another aspect of the invention, a second method and system for removing a background signal from a DNA melting curve is provided. Specifically, a device having at least one DNA sample is in communication with a thermal system. The thermal system is continuously increasing the temperature of the at least one DNA sample to cause a DNA melting reaction resulting in denaturing dsDNA to ssDNA.

A controller in communication with the device executes instructions for generating a melting curve F(T) for a DNA sample, wherein F is a fluorescence signal indicative of a DNA denaturation process and T is the temperature of the DNA sample. Next, the melting curve is divided into three regions. The three regions include a pre-DNA melt region $[T_1, T_2]$ and a post-DNA melt region $[T_3, T_4]$ corresponding to a background reaction, and a central melt region $[T_2, T_3]$ corresponding to the DNA melting reaction. A background reaction model is fitted to the regions $[T_1, T_2]$ and $[T_3, T_4]$ of the melting curve by determining parameters of the background reaction model and calculating a background reaction curve. Then, the background reaction curve is subtracted from the melting curve F(T) in the temperature interval $[T_1, T_4]$.

A third method and system for removing a background signal from a DNA melting curve is provided in a further aspect of the invention. Specifically, a device having at least one DNA sample is in communication with a thermal system. The thermal system is continuously increasing the temperature of the at least one DNA sample to cause a DNA melting reaction resulting in denaturing dsDNA to ssDNA.

A controller in communication with the microfluidic device provides instructions for generating a melting curve F(T) for a DNA sample, wherein F is a fluorescence signal indicative of a DNA denaturation process and T is the temperature of the DNA sample. Next, the melting curve F(T) is transformed by the controller to a curve log(F(T)−u) for different values of a u factor. The process continues by fitting, for each value of the u factor, a first background model $B_1(T)=s_1T+t_1$ to a pre-DNA melt region $[T_1, T_2]$ of the transformed melting curve log(F(T)−u) and a second background model $B_2(T)=s_2T+t_2$ to a post-DNA melt region $[T_3, T_4]$ of the transformed melting curve log(f(T)−u) thereby determining $s_1$, $s_2$, $t_1$, $t_2$, $T_1$, $T_2$, $T_3$, and $T_4$. Then, the u factor is selected such that $s_1=s_2$. Finally, the background signal is removed from the melting curve F(T) based upon the first and second background models $B_1(T)$ and $B_2(T)$.

In yet another aspect of the invention, a fourth method and system for removing a background signal from a DNA melting curve is provided. A microfluidic device having at least one DNA sample is in communication with a thermal system. The thermal system is continuously increasing the temperature of the at least one DNA sample to cause a DNA melting reaction resulting in denaturing dsDNA to ssDNA. Furthermore, a controller is provided in communication with the microfluidic device to execute instructions including: (a) generating a melting curve F(T) for a DNA sample, wherein F is a fluorescence signal indicative of a DNA denaturation process and T is the temperature of the DNA sample; (b) transforming the melting curve F(T) to a curve log(F(T)−u) for a first approximation of a u factor; (c) calculating a first background model $B_1(T)=sT+t_1$ for a predefined pre-DNA melt region $[T_1, T_2]$ of the transformed melting curve log(F(T)−u) and a second background model $B_2(T)=sT+t_2$ for a predefined post-DNA melt region $[T_3, T_4]$ of the transformed melting curve log(F(T)−u) by minimizing a first objective function to calculate parameters s, $t_1$, and $t_2$; (d) taking s, $t_1$, and $t_2$ calculated in step (c) as an approximation to calculate a second approximation of the u factor, the second approximation for the u factor being calculated by minimizing a second objective function; (e) repeating steps (c) and (d) until the parameters u; $t_1$, and $t_2$, and s converge, wherein u, $t_1$, and $t_2$, ands ultimately minimize the first and second objective functions; and (f) removing the background signal from the curve F(T) based upon the first and second background models $B_1(T)$ and $B_2(T)$.

A method and system for identifying an internal template control region in a melting curve derivative is provided in another aspect of the invention. Specifically, a plurality of DNA samples undergoing melting analysis in a DNA vessel is provided. The DNA vessel is in communication with a temperature control system and an imaging system. Each sample includes an internal template control having a pre-determined melt temperature. The temperature in the plurality of DNA samples is ramped by the temperature control system to achieve DNA denaturing. A plurality of DNA melting curves is generated for the plurality of samples by using the imaging system to measure fluorescence as a function of temperature. A negative derivative plot is calculated for each generated DNA melting curve.

Next, start and end temperature values, ITC1 and ITC2, defining the internal template control region in the derivative plot of the plurality of DNA melting curves are calculated by a controller. Specifically, peaks and temperatures corresponding to the peaks are identified by a controller in each negative derivative plot. The temperatures corresponding to the peaks are clustered and temperature cluster centers are determined. Finally, the start and end temperature values are identified for the internal template control region based on the temperature cluster centers.

A method and system for normalizing a plurality of DNA melting curves by determining a melt region in a melting curve is provided in another aspect of the invention. Specifically, a plurality of DNA samples undergoing melting analysis in a DNA vessel is provided. The DNA vessel is in communication with a temperature control system and an imaging system. Each sample includes an internal template control having a pre-determined melt temperature. The temperature in the plurality of DNA samples is ramped by the temperature control system to achieve DNA denaturing. A plurality of DNA melting curves is generated for the plurality of samples by using the imaging system to measure fluorescence as a function of temperature. A negative derivative plot is calculated for each generated DNA melting curve.

A controller identifies start and end temperatures of the melt region of the melting curve to normalize the DNA melting curves based at least in part on the identified melt region of the melting curves. Specifically, the controller executes instructions comprising: (a) determining a first temperature interval to search for a start temperature of the melt region; (b) determining a second temperature interval to search for an end temperature of the melt region; (c) fixing the end temperature and calculating a statistic of the normalized derivative curve at each candidate start temperature from the first search interval; (d) determining the start temperature based on the statistic calculated in step (c); (e) fixing the start temperature obtained in step (d) and calculating the statistic of the normalized derivative curve at each candidate end temperature from the second search interval; and repeating steps (c)-(e) until the start and end temperatures converge.

In yet another aspect of the invention, a method and system for interactive data analysis involving a server based application in communication with a client machine is provided. In one embodiment, the server is a cloud server. Specifically, the system comprises a server communicating with a user interface on the client machine over a network. The server has memory including instructions to process raw experimental data received over the network from the client machine. The experimental data is formatted to define an instrument where the raw experimental data originated from. The UI is in communication with the client machine to present processed experimental data to a user, the UI reflecting a type of the instrument. The type of the instrument is characterized by a sample arrangement displayed through the UI.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

The accompanying drawings, which are incorporated herein and form part of the specification, illustrate various embodiments of the present invention.

Figure 1:
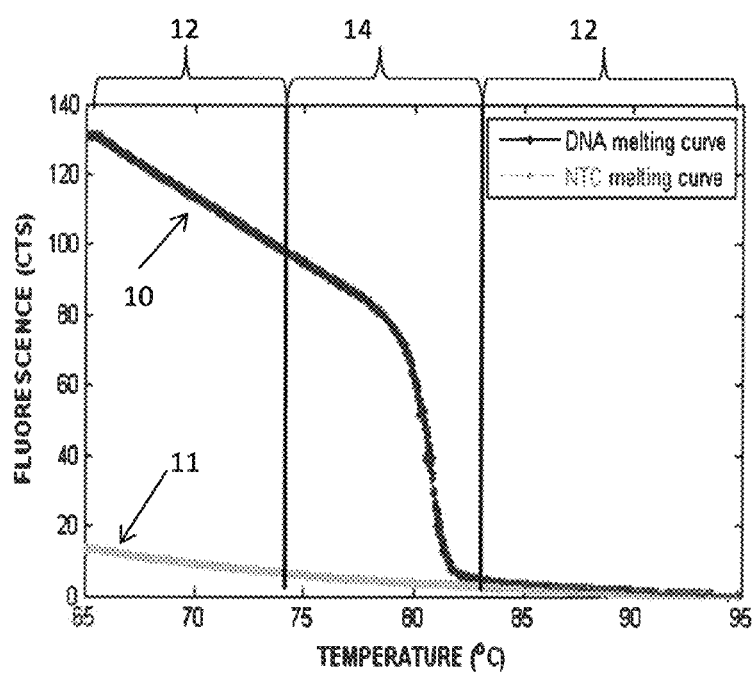

FIG. 1 illustrates a graph including an exemplary DNA melt curve and a control curve as is known in the prior art.

Figure 2:
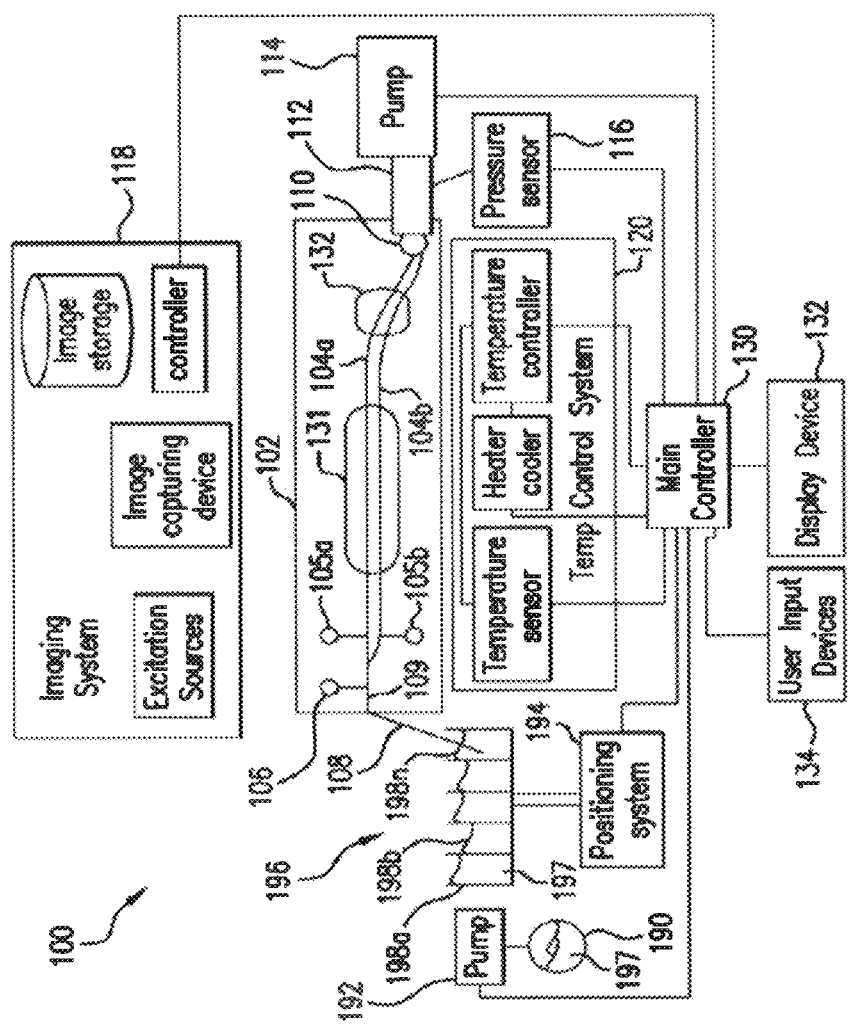

FIG. 2 is a block diagram detailing the components of a genetic analyzer device according to invention principles.

Figure 3:
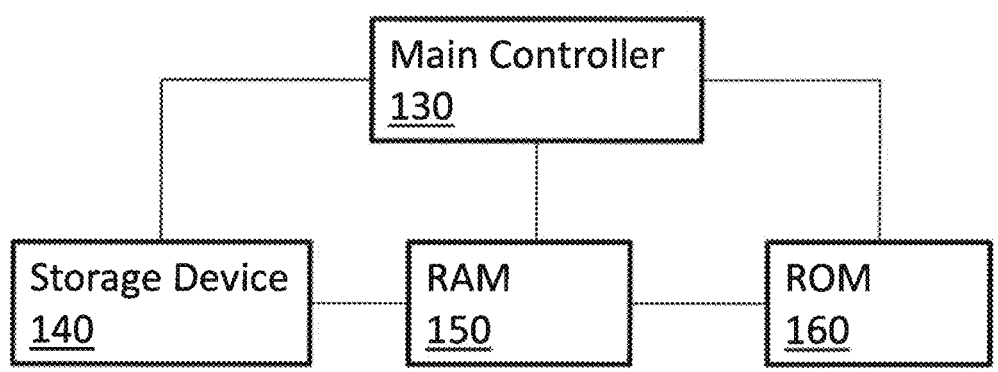

FIG. 3 is block diagram detailing additional components of the genetic analyzer device according to invention principles.

Figure 4:
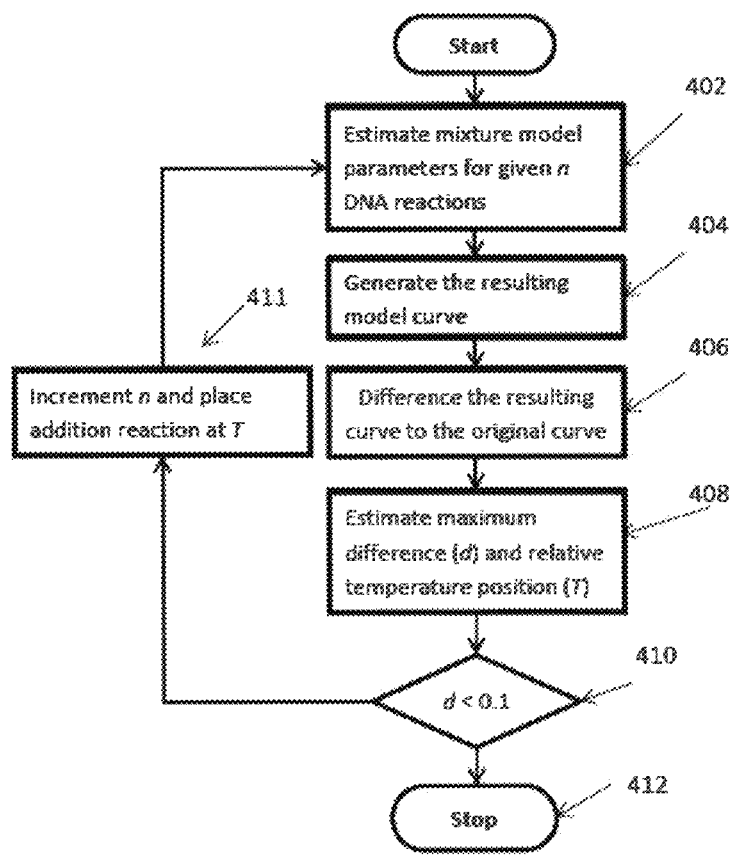

FIG. 4 is a flow diagram detailing an algorithm according to invention principles.

Figure 5A:
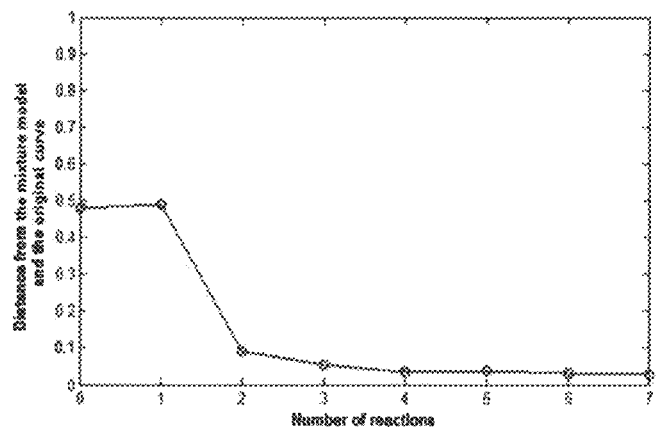
Figure 5B:
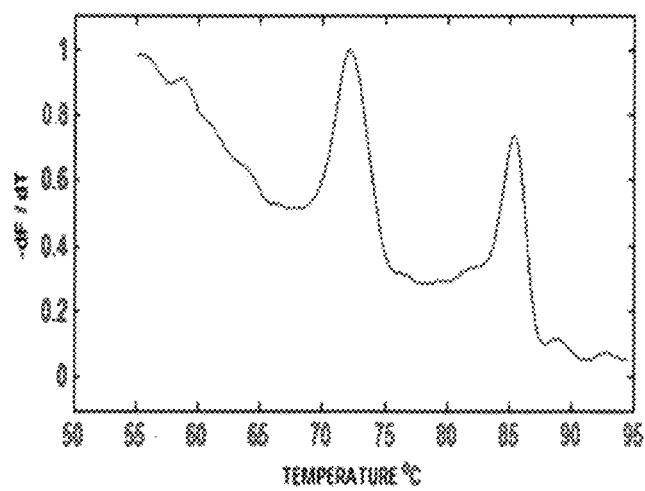

FIGS. 5A & 5B are graphs illustrating aspects of the invention.

Figure 6:
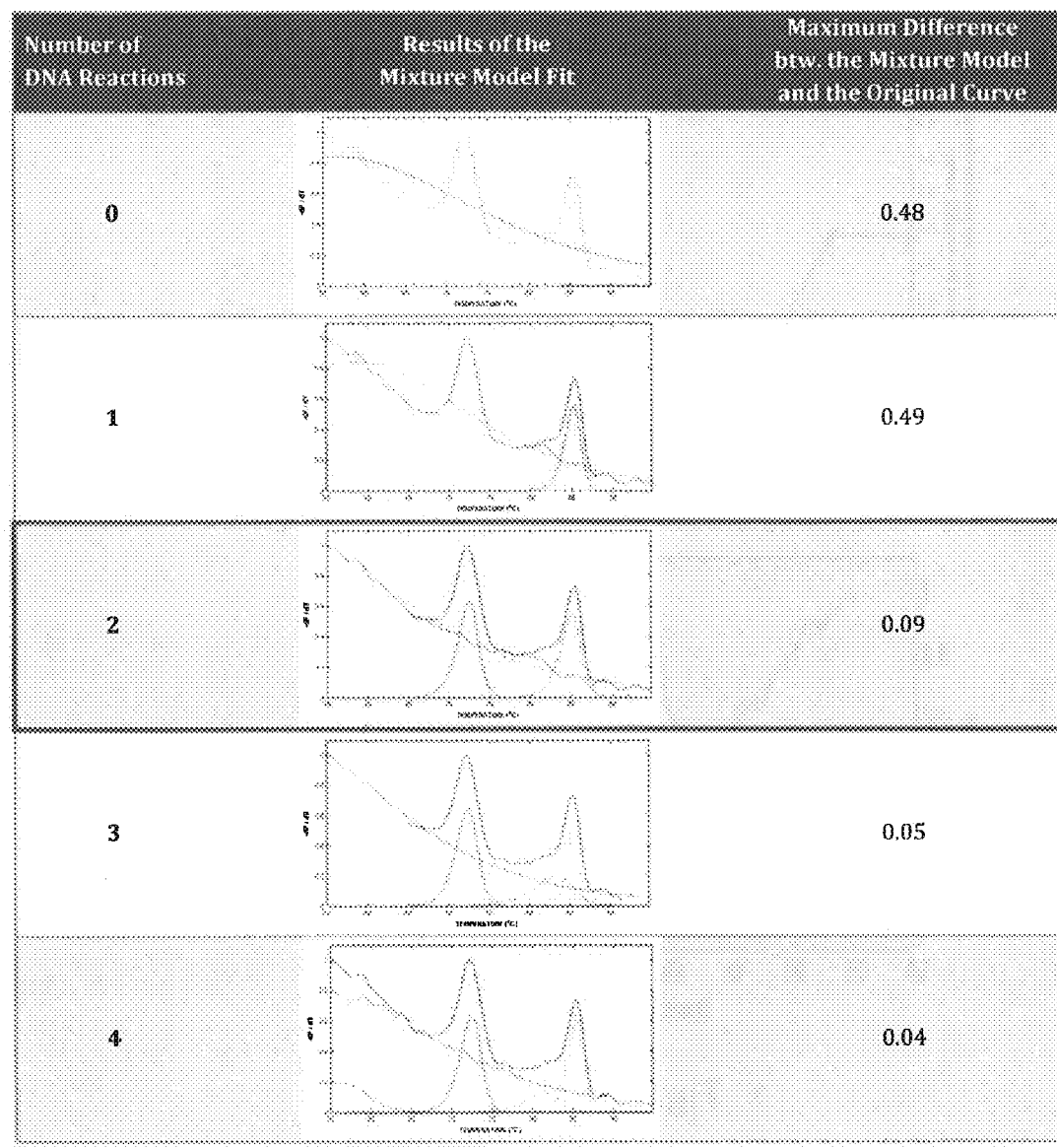

FIG. 6 is a table illustrating various outcomes of the algorithm according to invention principles.

Figure 7:
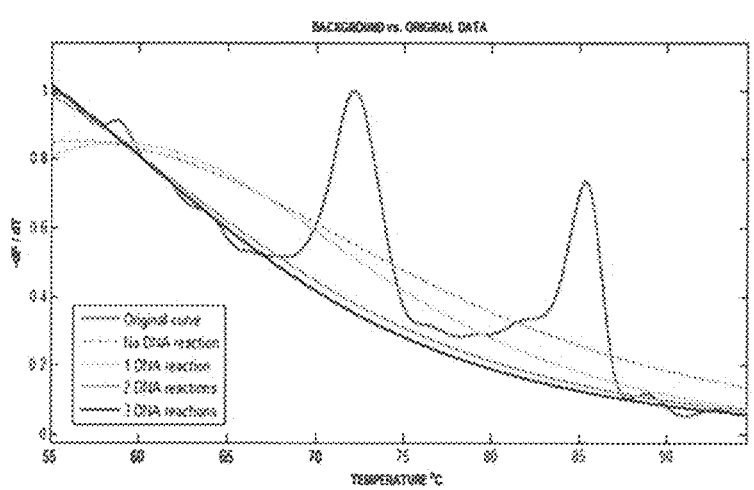

FIG. 7 illustrates graphical representations of data output by the algorithm according to invention principles.

Figure 8:
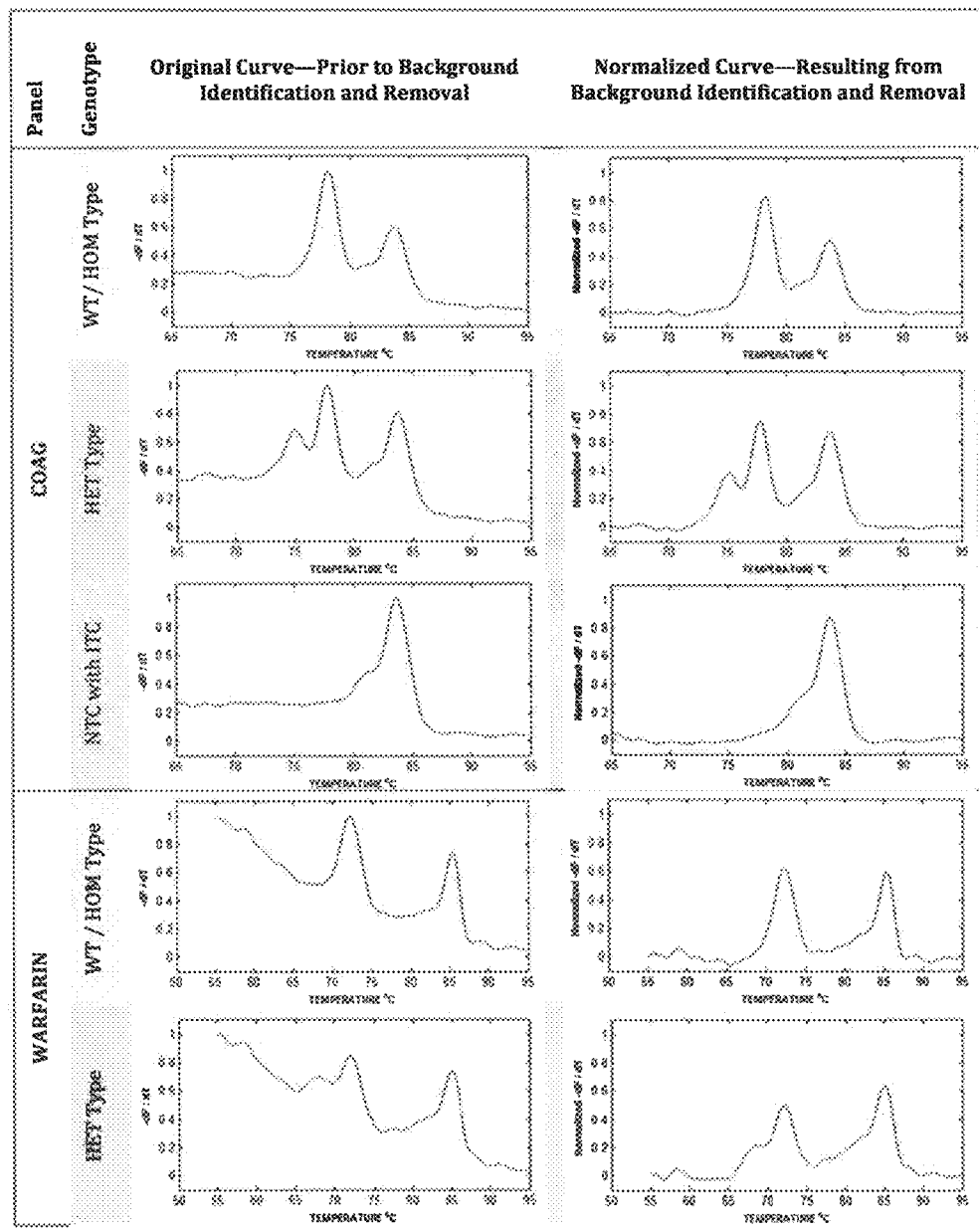

FIG. 8 illustrates graphical representations of data output by the algorithm according to invention principles.

Figure 9:
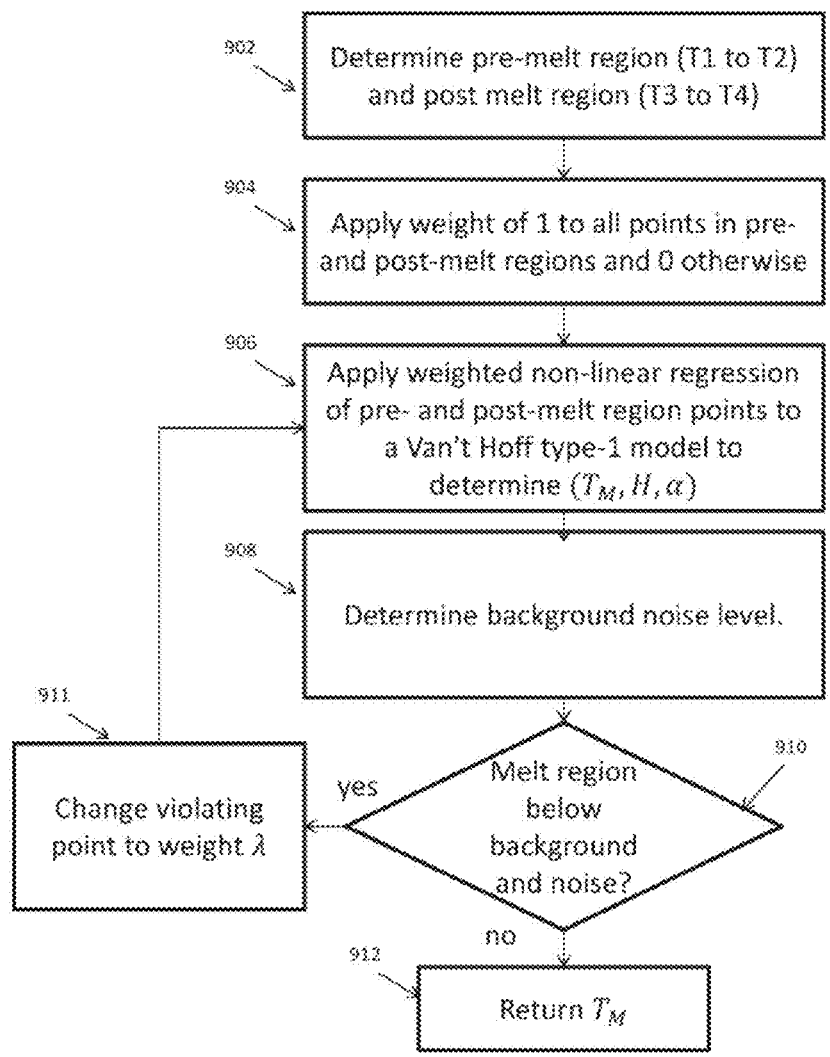

FIG. 9 illustrates an algorithm according to invention principles.

Figure 10A:
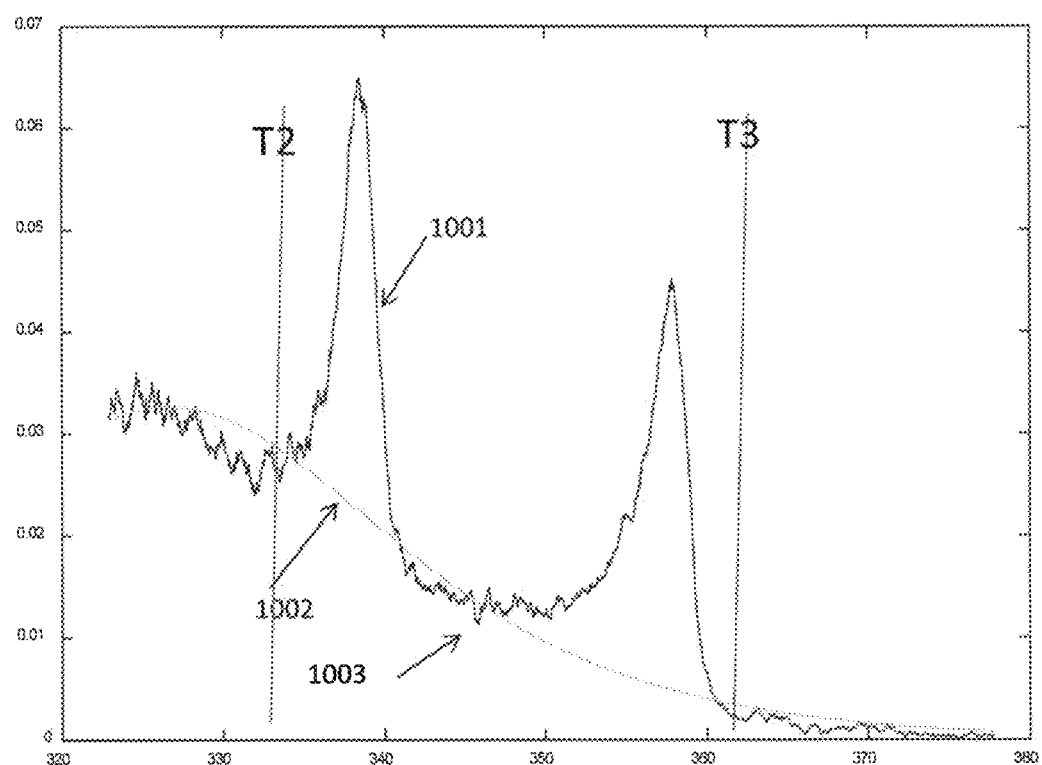
Figure 10B:
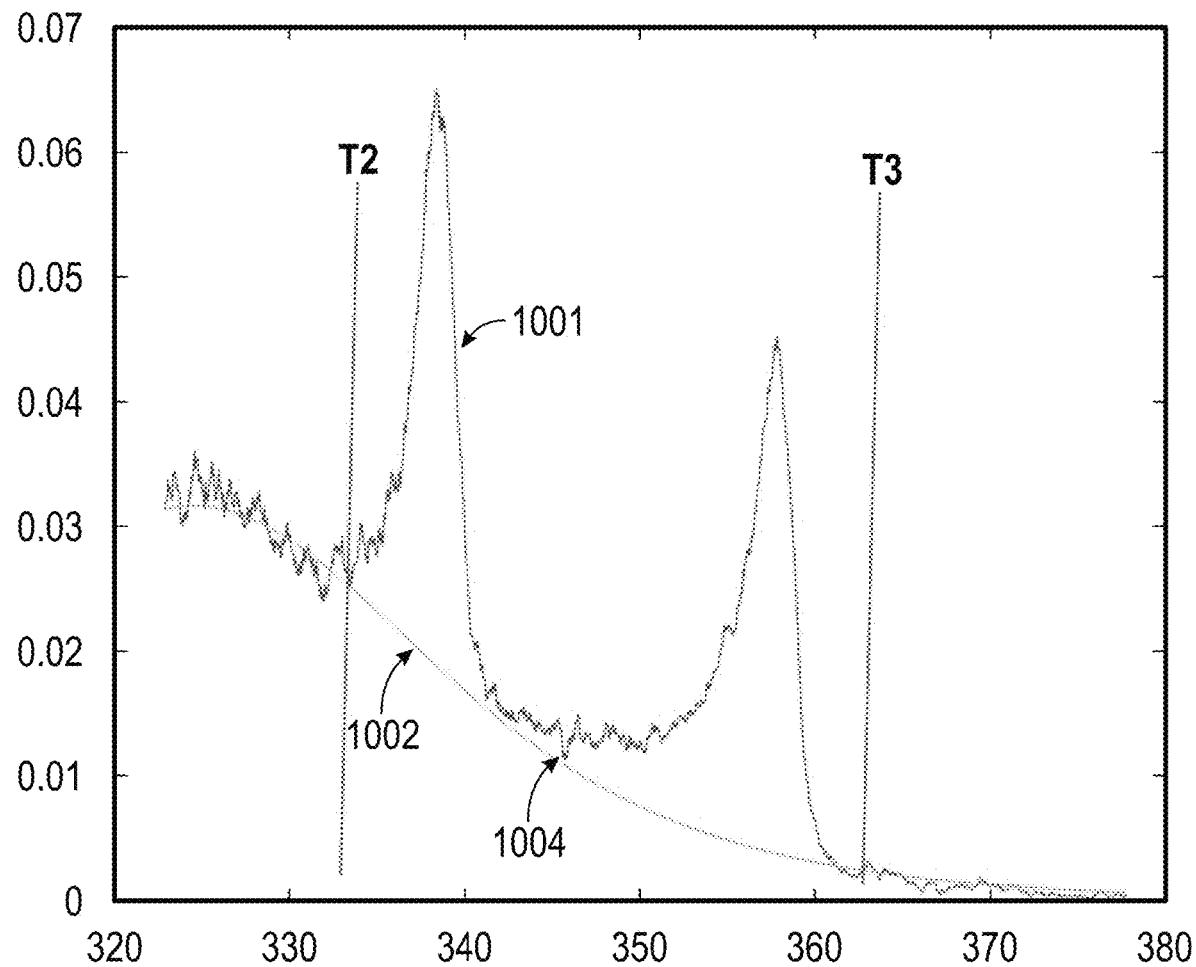
Figure 11A:
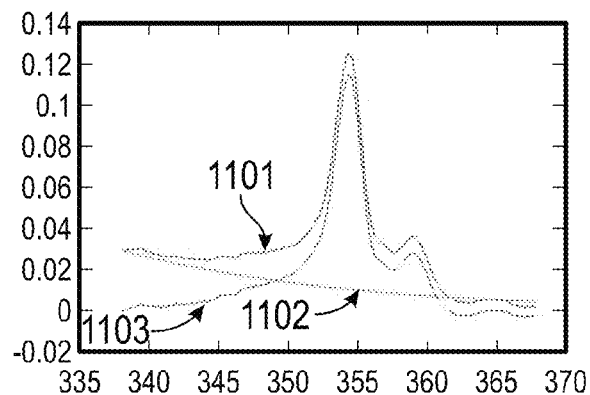
Figure 11B:
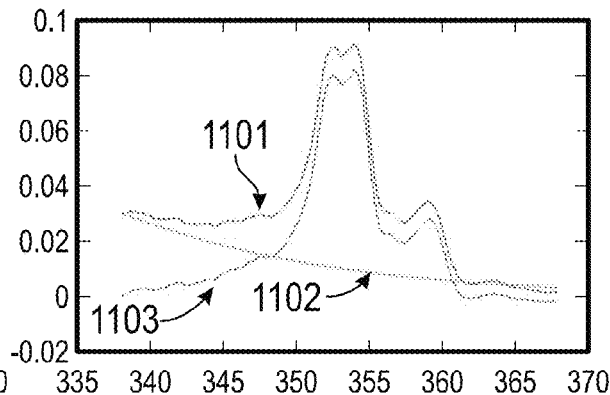
Figure 11C:
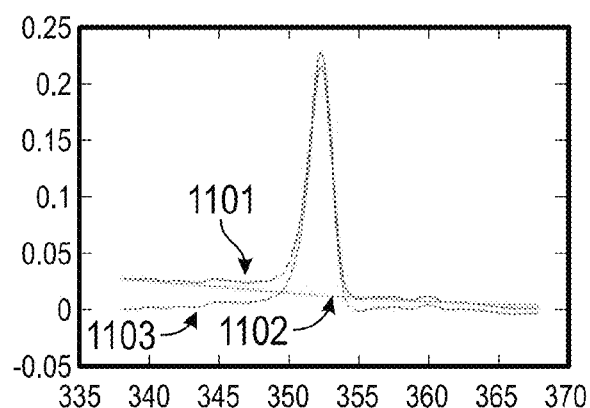
Figure 11D:
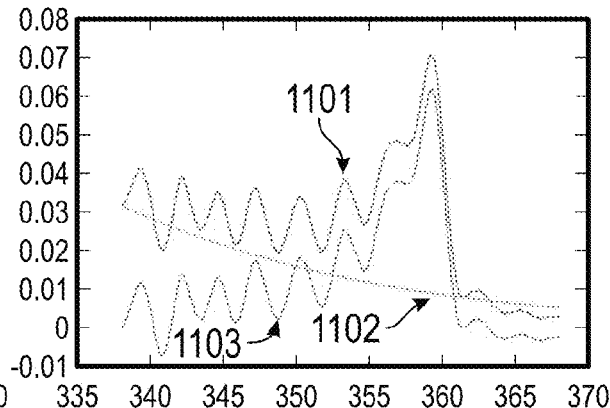

FIGS. 10A and 10B illustrate graphical representations of data output by the algorithm according to invention principles.

FIGS. 11A-11D illustrate graphical representations of data output by the algorithm according to invention principles.

Figure 12:
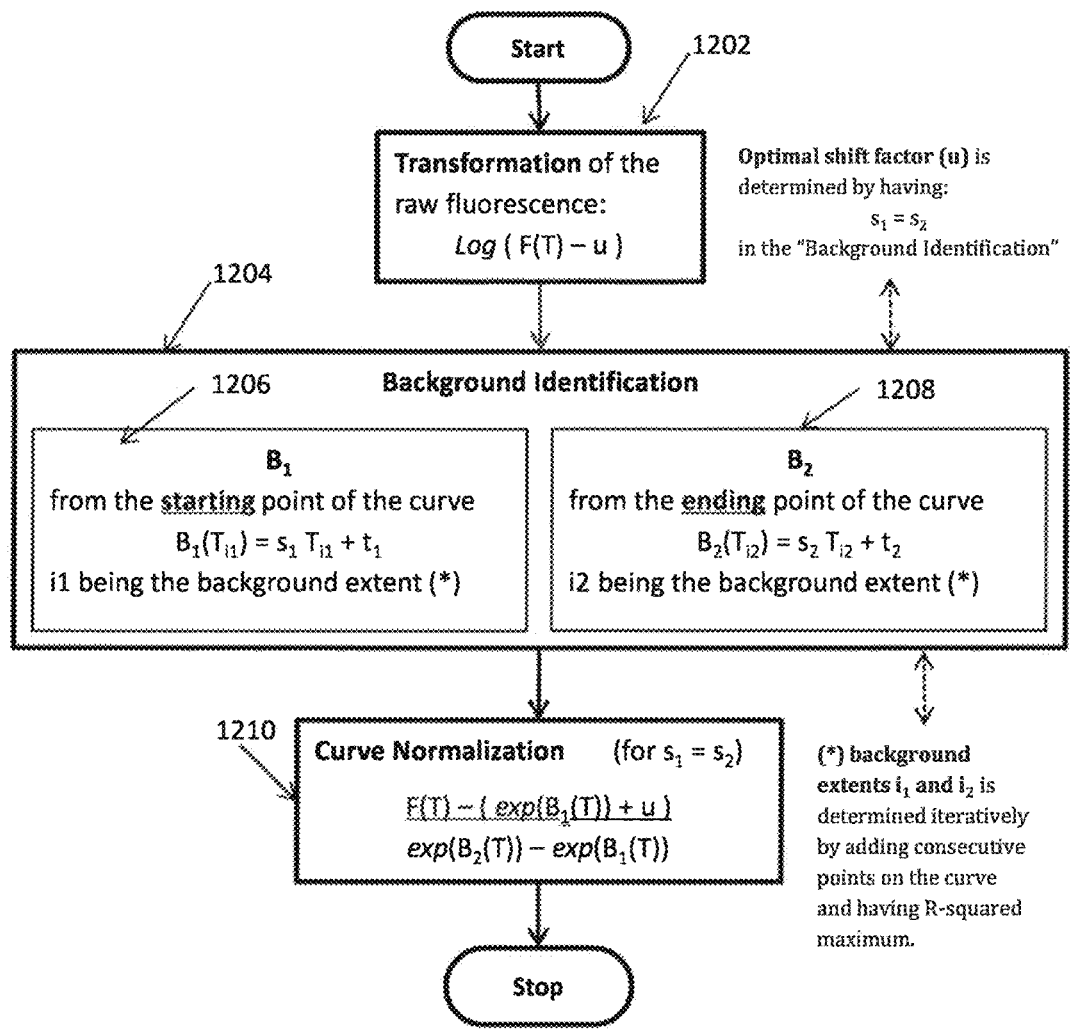

FIG. 12 illustrates an algorithm according to invention principles.

Figure 13A:
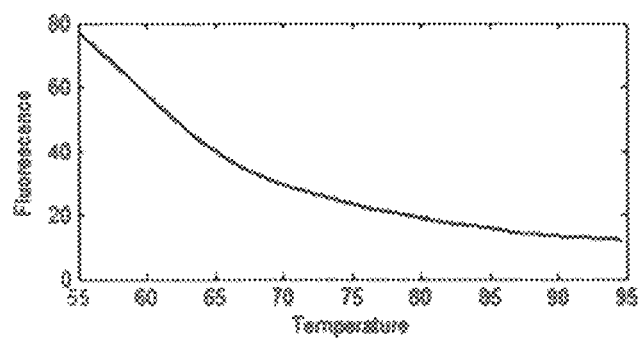
Figure 13B:
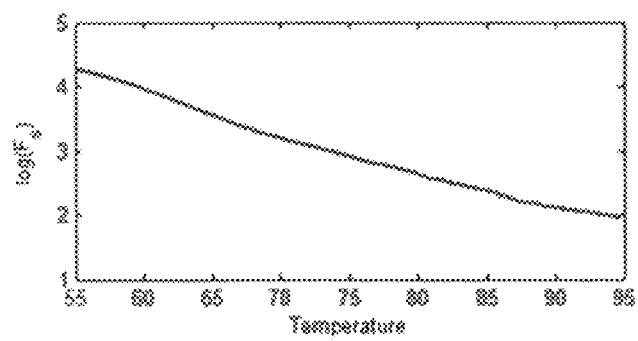

FIGS. 13A and 13B illustrate graphical representations of data output by the algorithm according to invention principles.

Figure 14A:
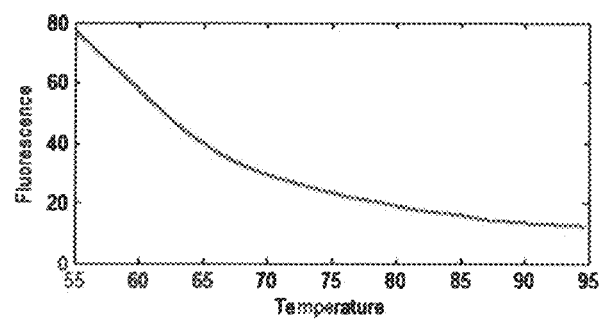
Figure 14B:
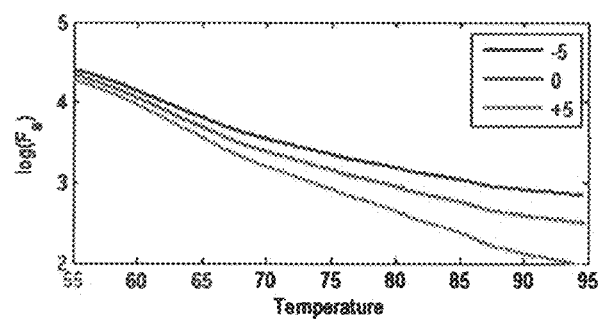

FIGS. 14A and 14B illustrate graphical representations of data output by the algorithm according to invention principles.

Figure 15A:
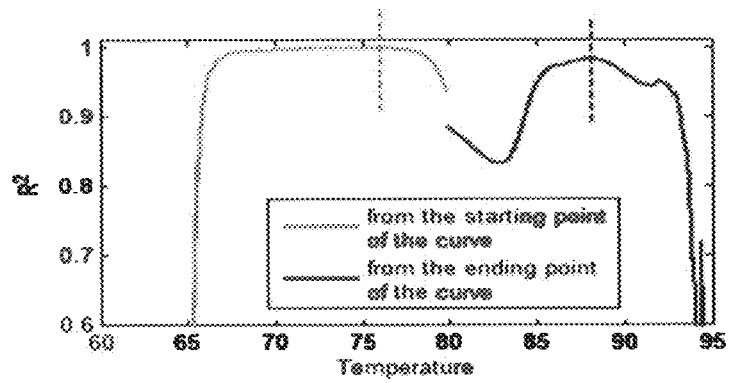
Figure 15B:
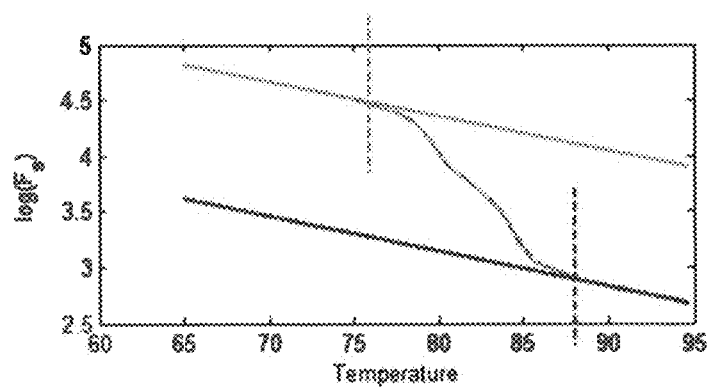

FIGS. 15A and 15B illustrate graphical representations of data output by the algorithm according to invention principles.

Figure 16:
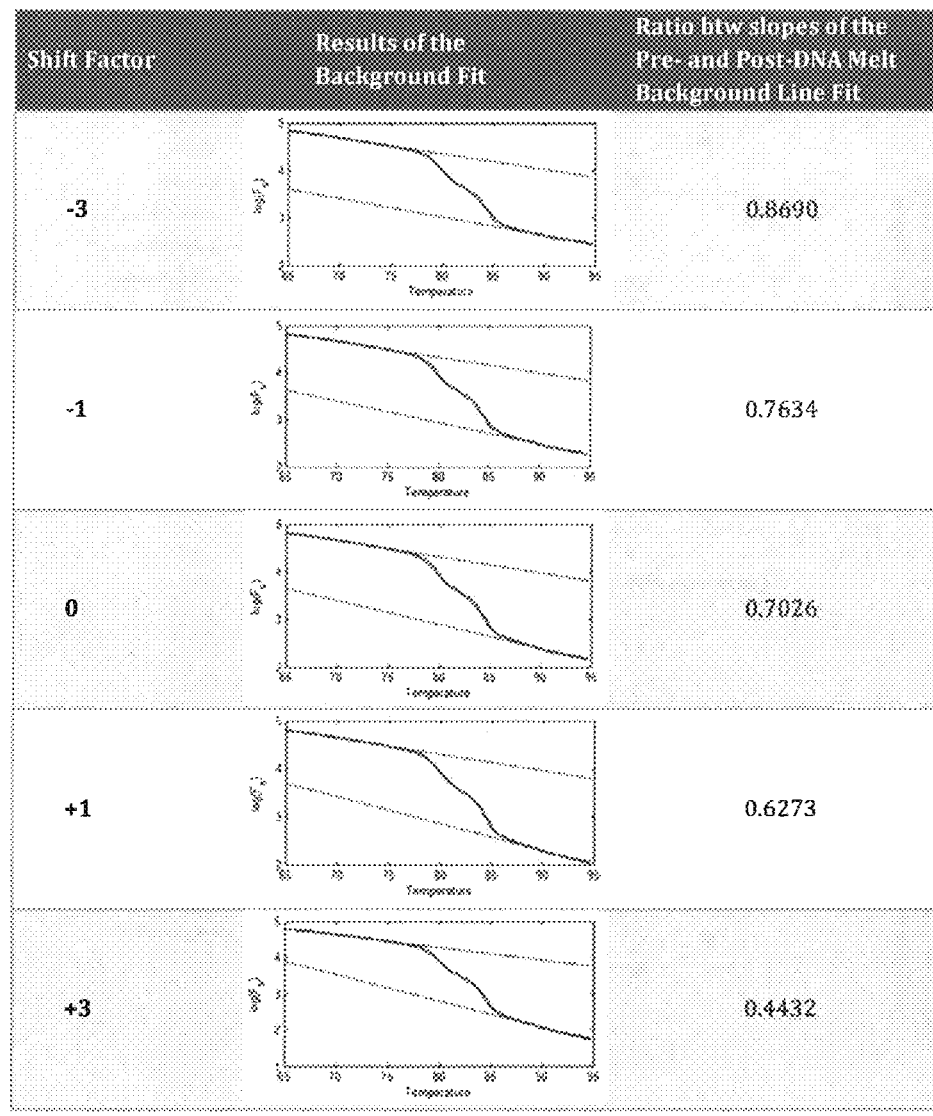

FIG. 16 is a table illustrating various outcomes of the algorithm according to invention principles.

Figure 17A:
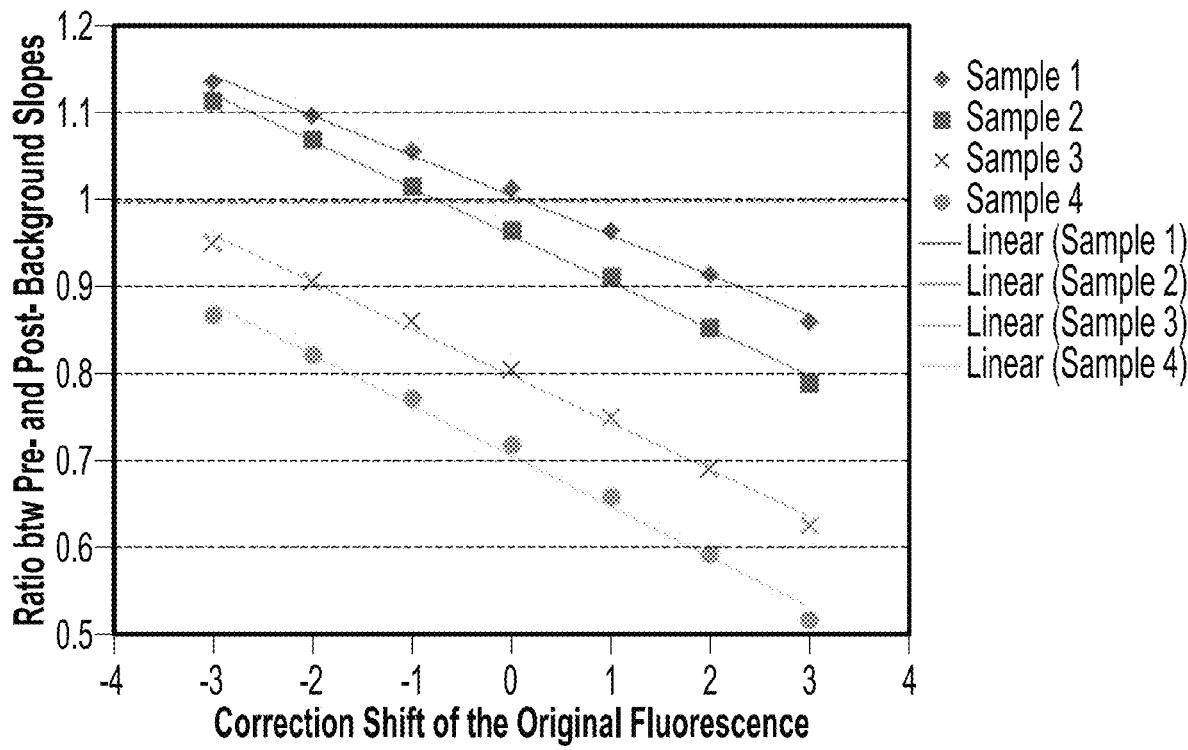
Figure 17B:
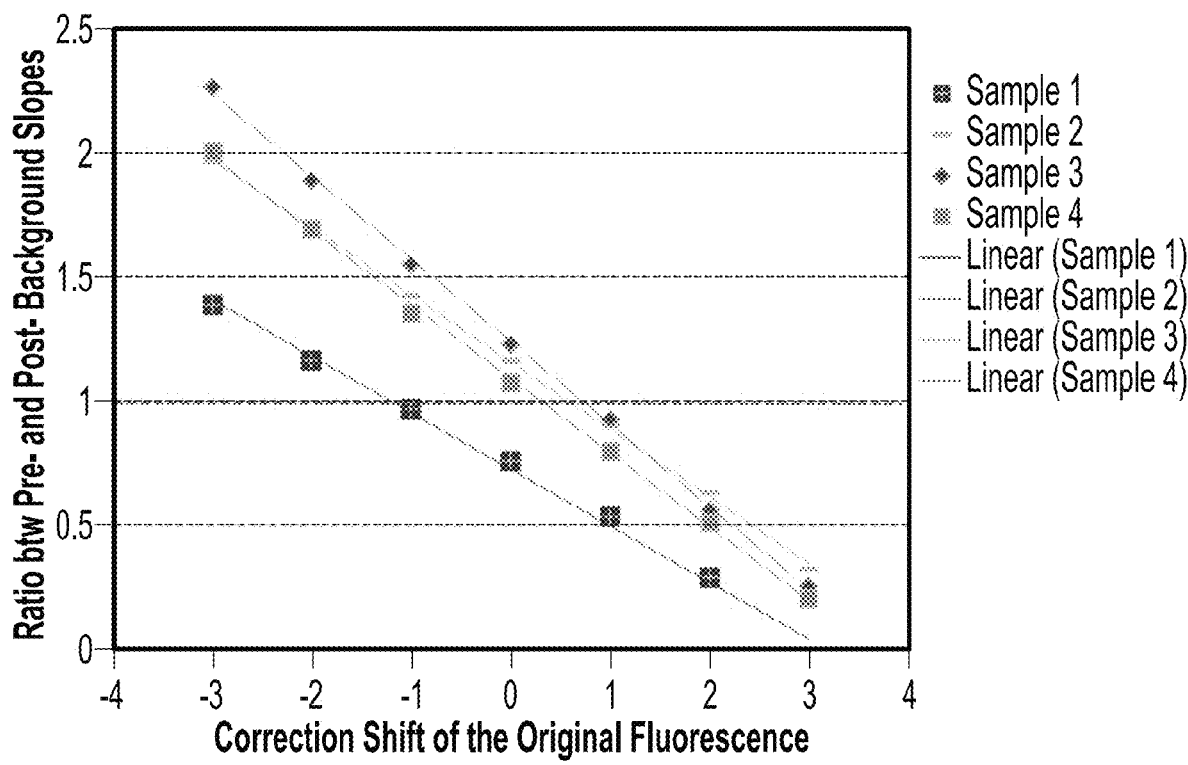

FIGS. 17A and 17B illustrate graphical representations of data output by the algorithm according to invention principles.

Figure 18:
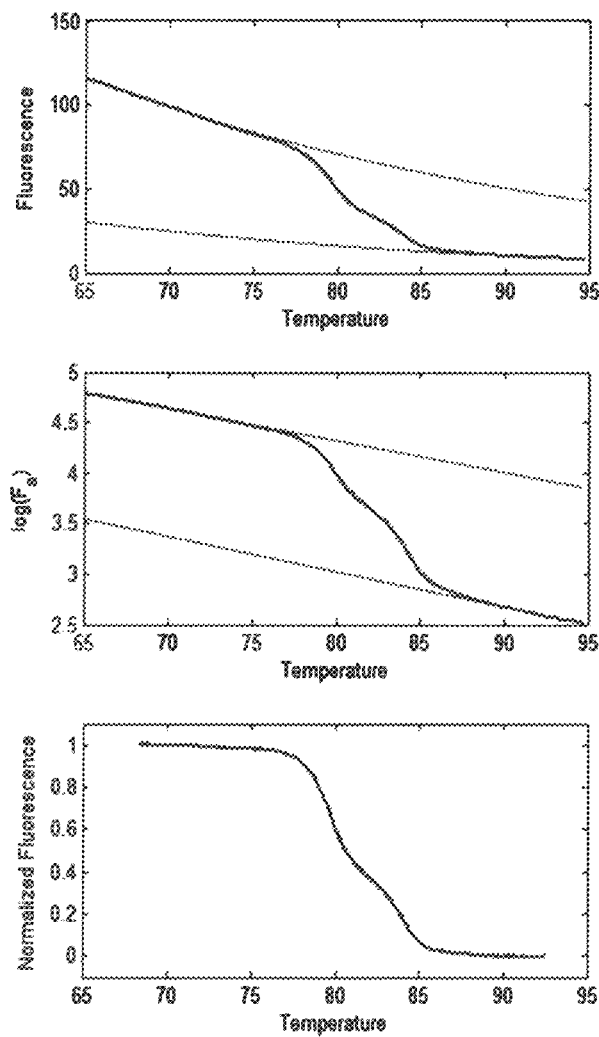

FIG. 18 illustrates graphical representations of data output by the algorithm according to invention principles.

Figure 19:
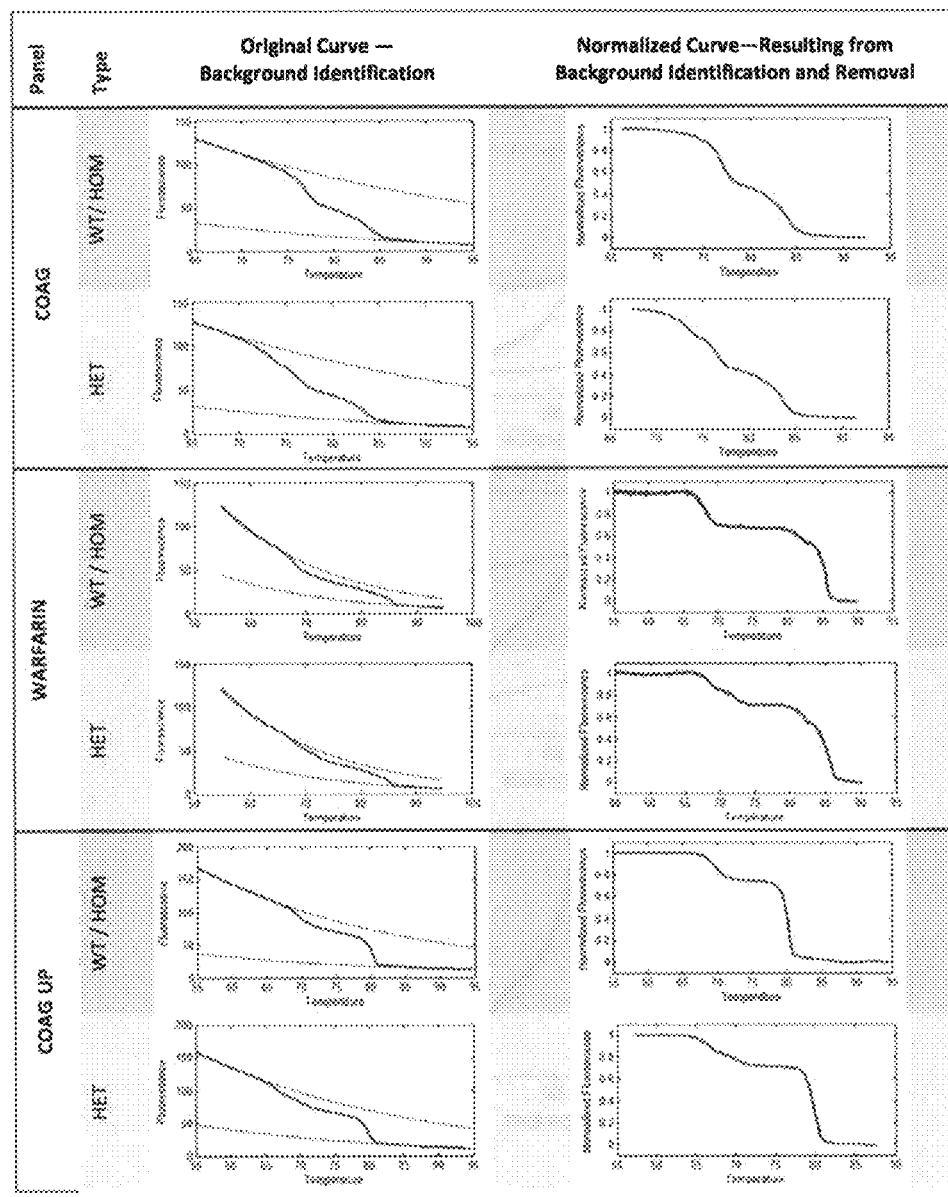

FIG. 19 illustrates graphical representations of data output by the algorithm according to invention principles.

Figure 20:
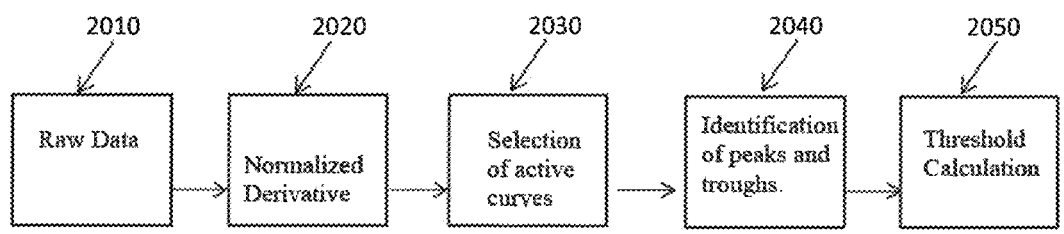

FIG. 20 is a block diagram for automated peak identification in a melting curve derivative.

Figure 21:
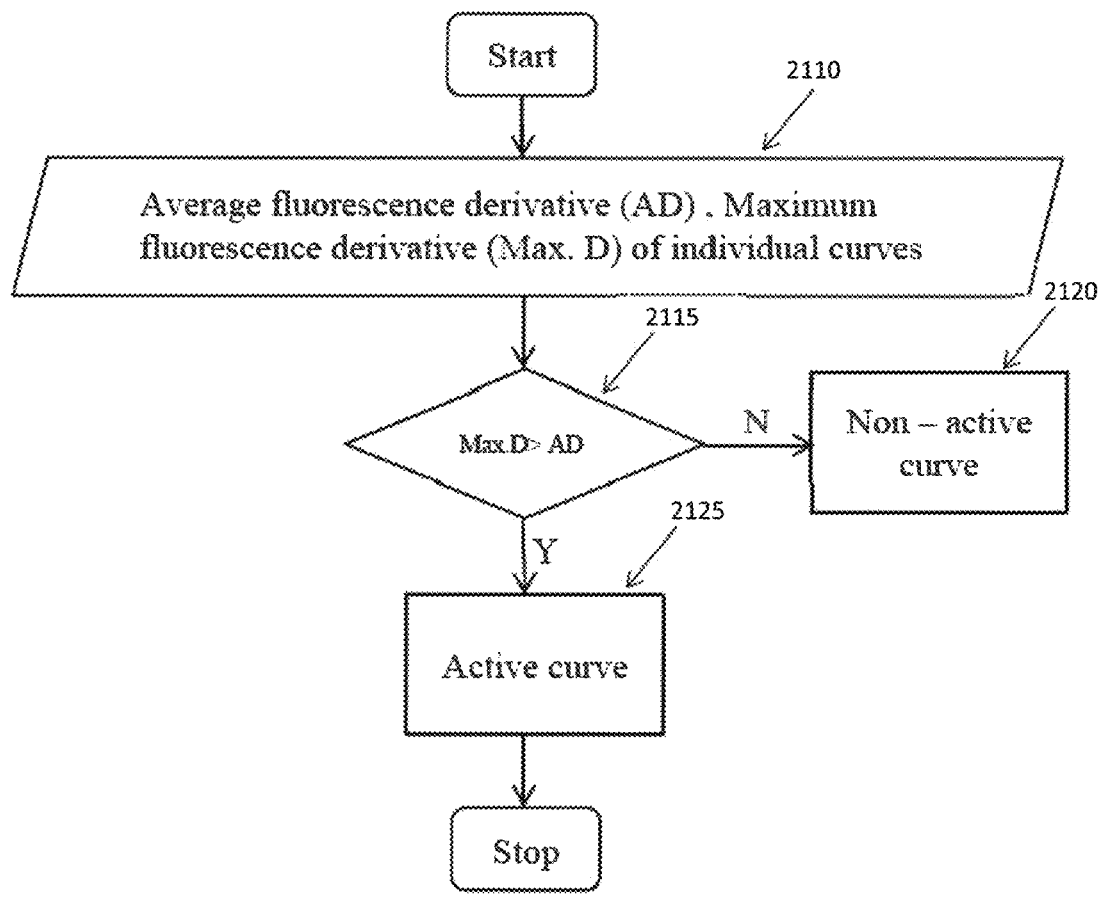

FIG. 21 is a flowchart demonstrating a process of active curves selection.

Figure 22:
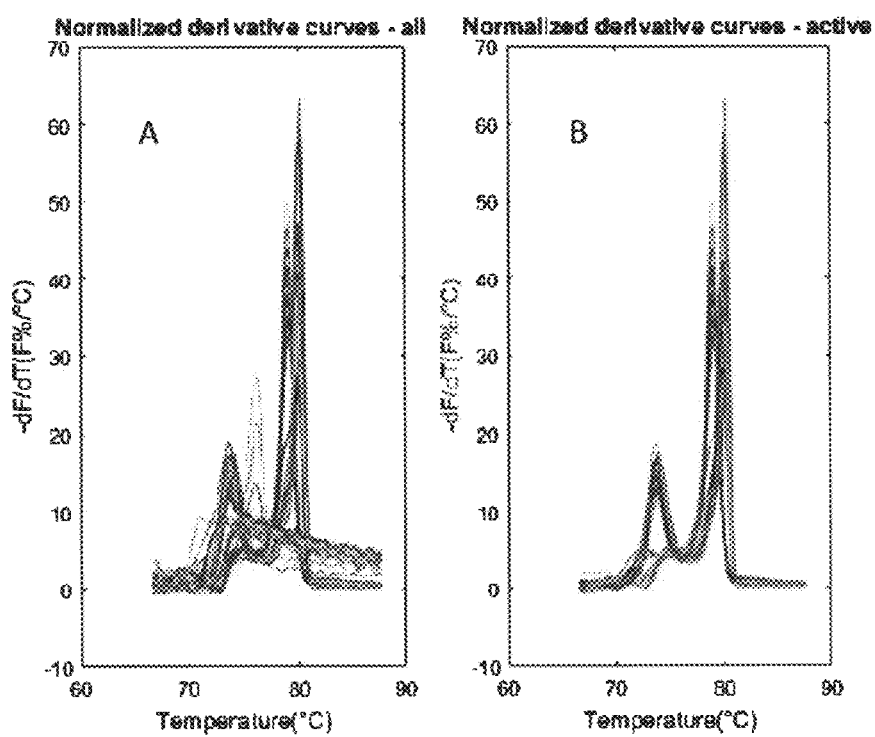

FIG. 22A demonstrates plots of all normalized derivative curves.

FIG. 22B demonstrates plots of only active normalized derivative curves.

Figure 23:
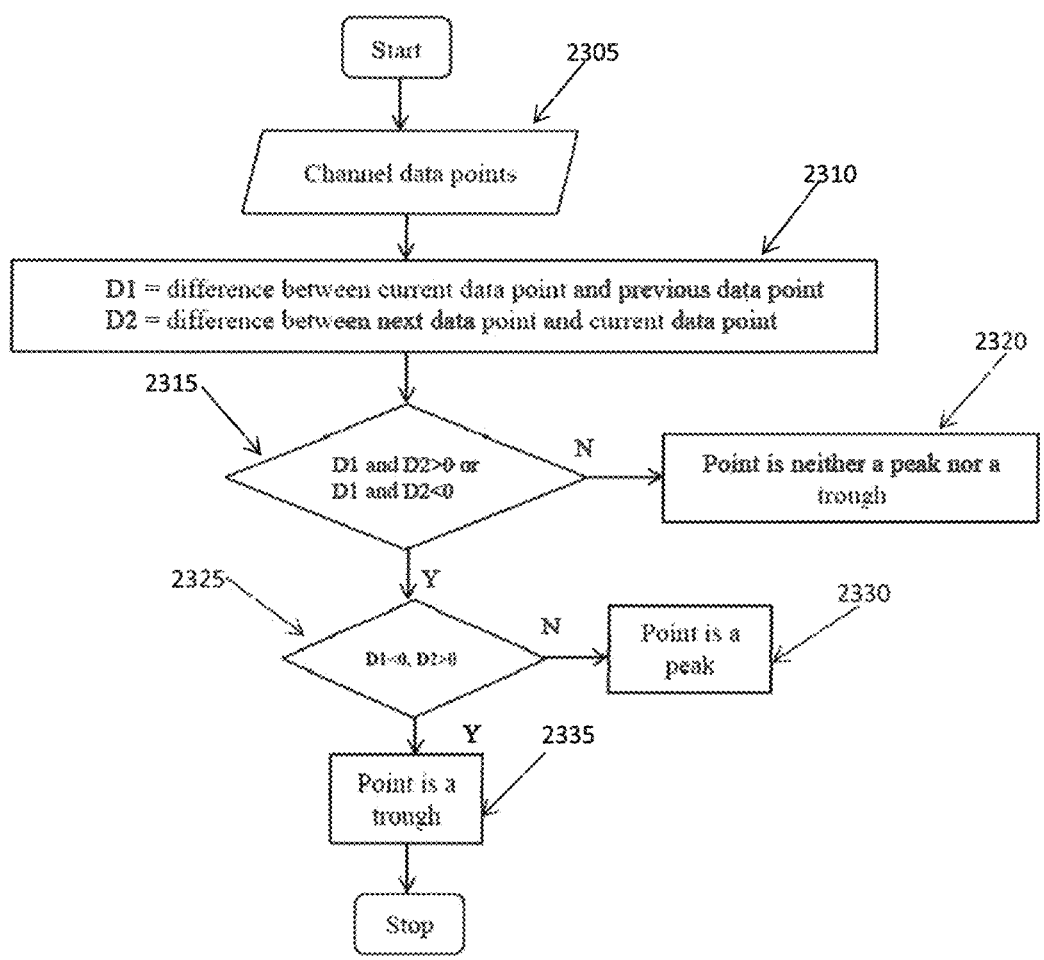

FIG. 23 is a flowchart demonstrating a process of peak detection.

Figure 24:
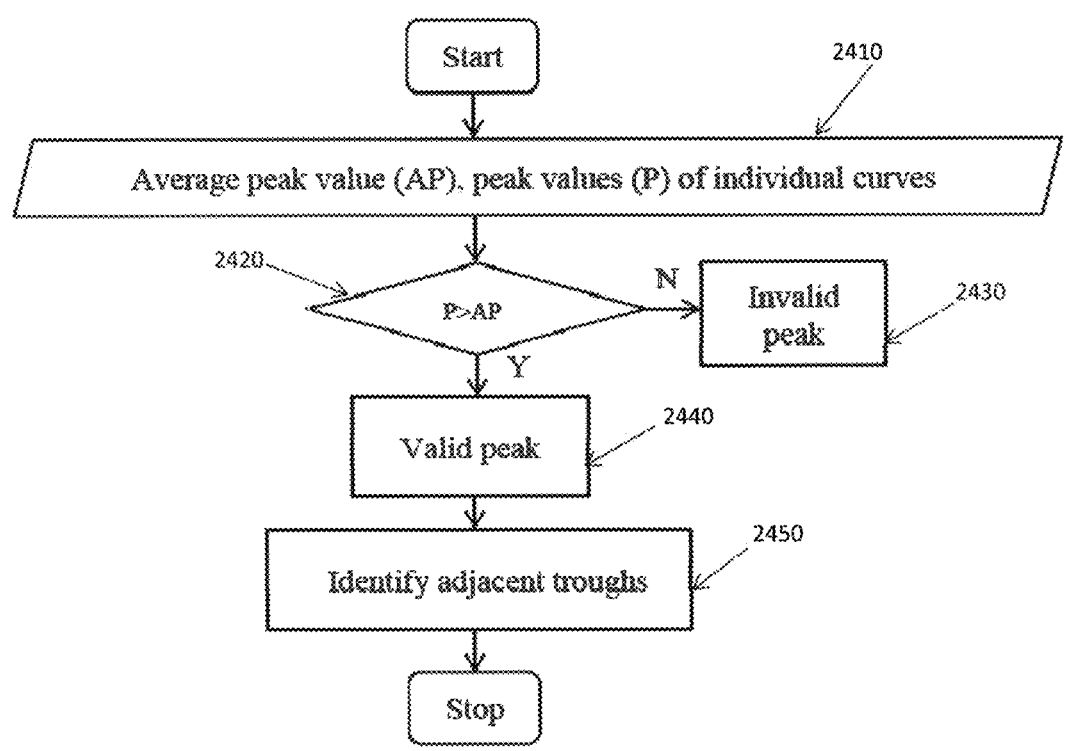

FIG. 24 is a flowchart demonstrating a process of valid peak classification.

Figure 25:
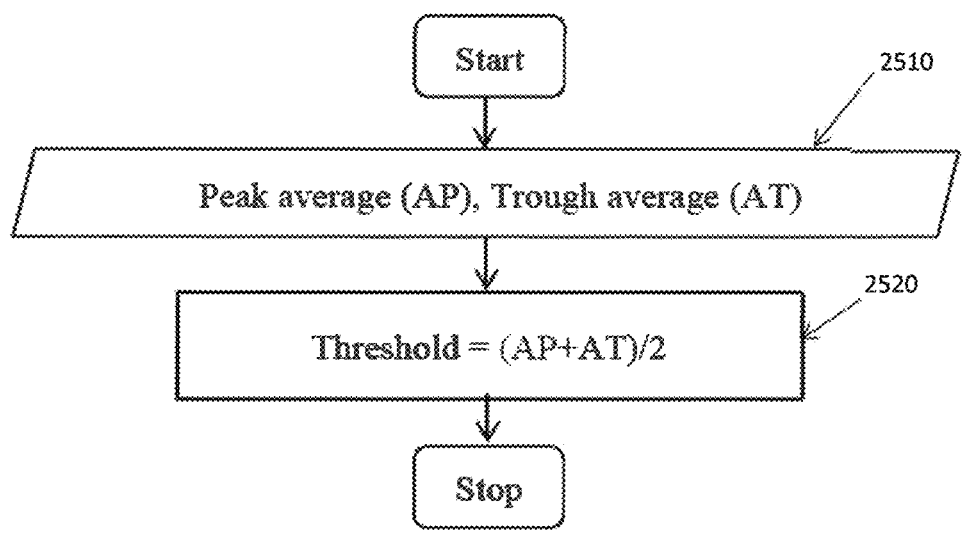

FIG. 25 is a flowchart demonstrating a process of threshold calculation.

Figure 26:
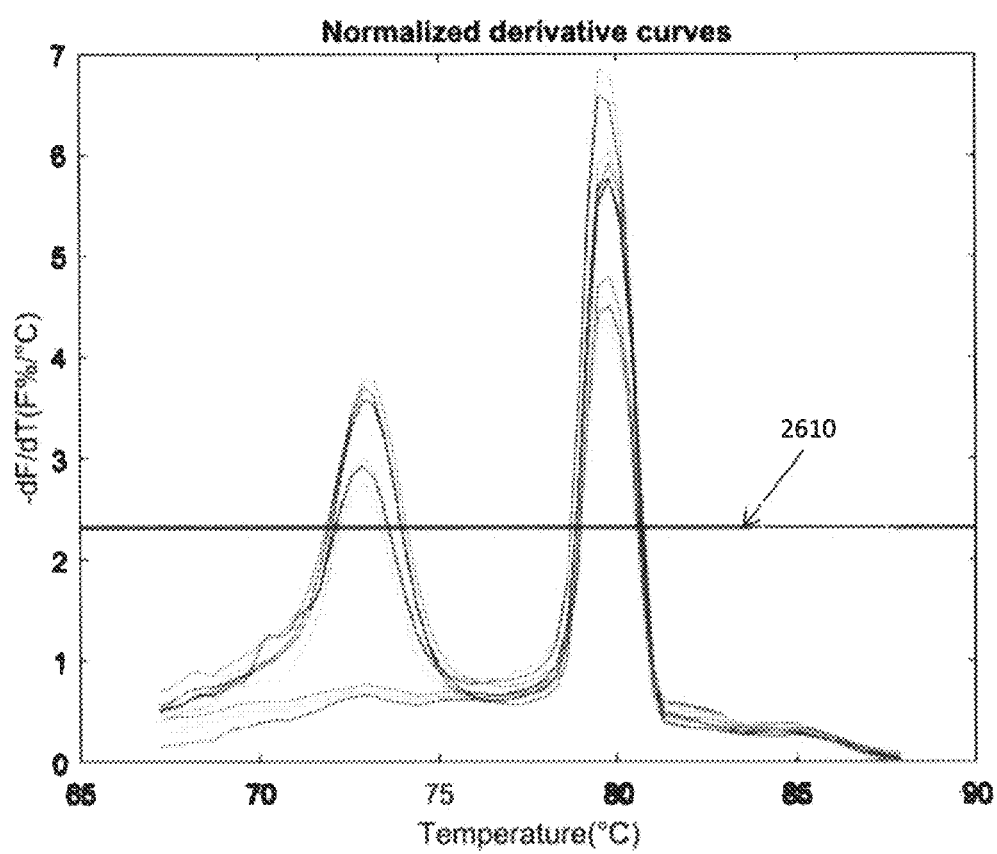

FIG. 26 demonstrates normalized derivative curves with threshold bar placed using the process of FIG. 25.

Figure 27:
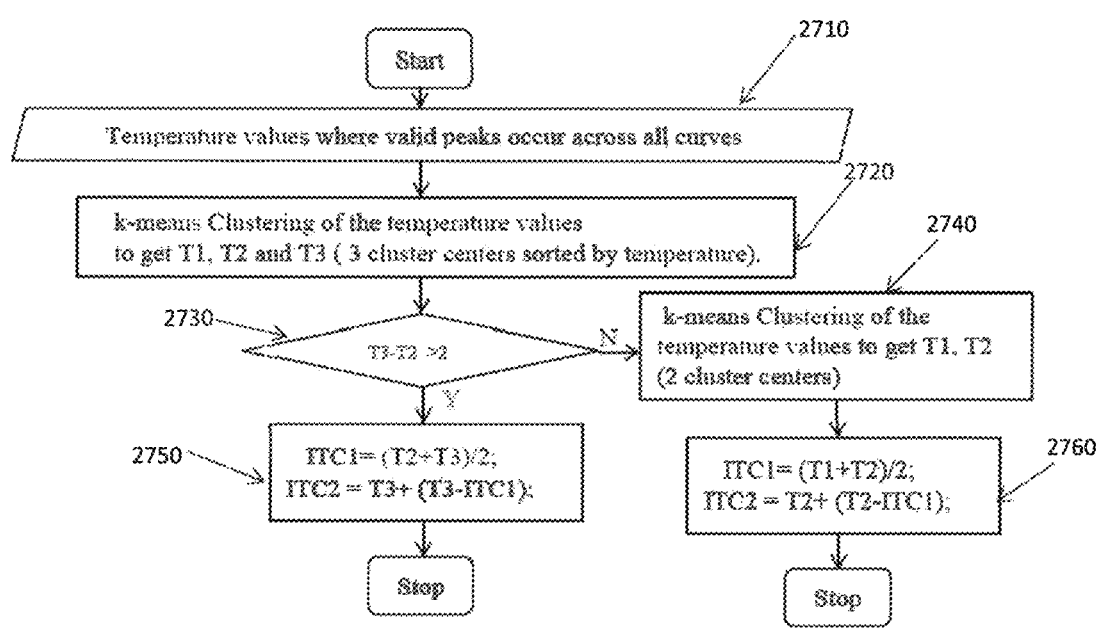

FIG. 27 is a flowchart demonstrating a process for ITC region definition.

Figure 28:
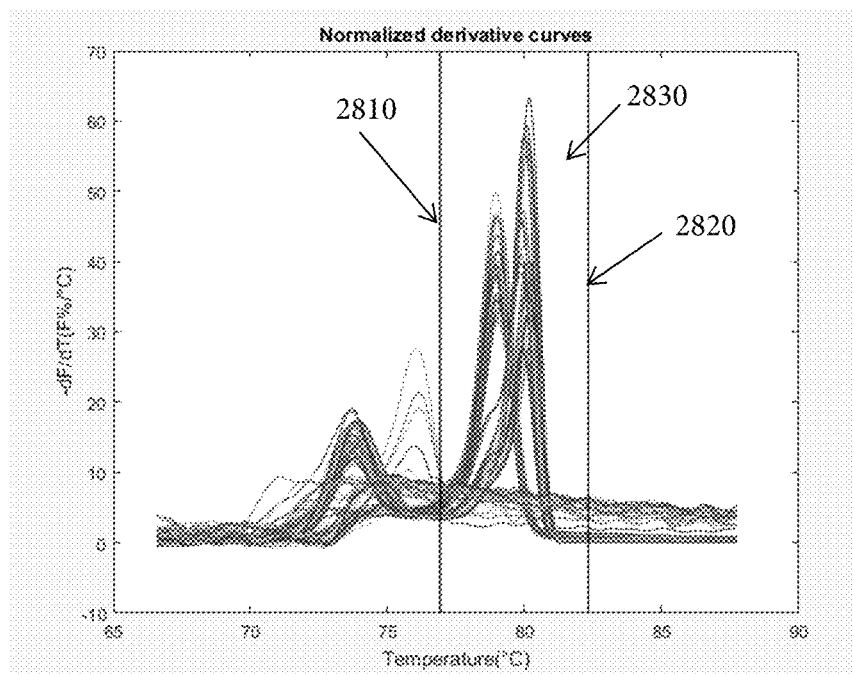

FIG. 28 demonstrates normalized derivative curves with ITC bars placed using the process of FIG. 26.

Figure 29:
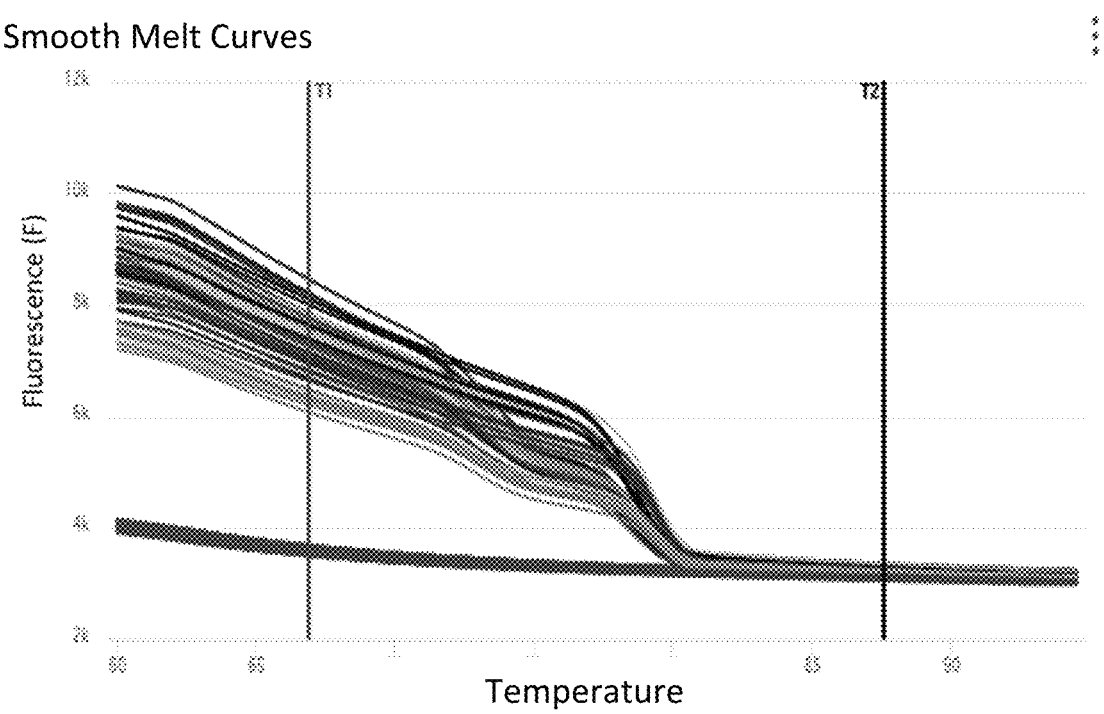

FIG. 29 demonstrates DNA melting curves with two vertical bars defining a melt region.

Figure 30:
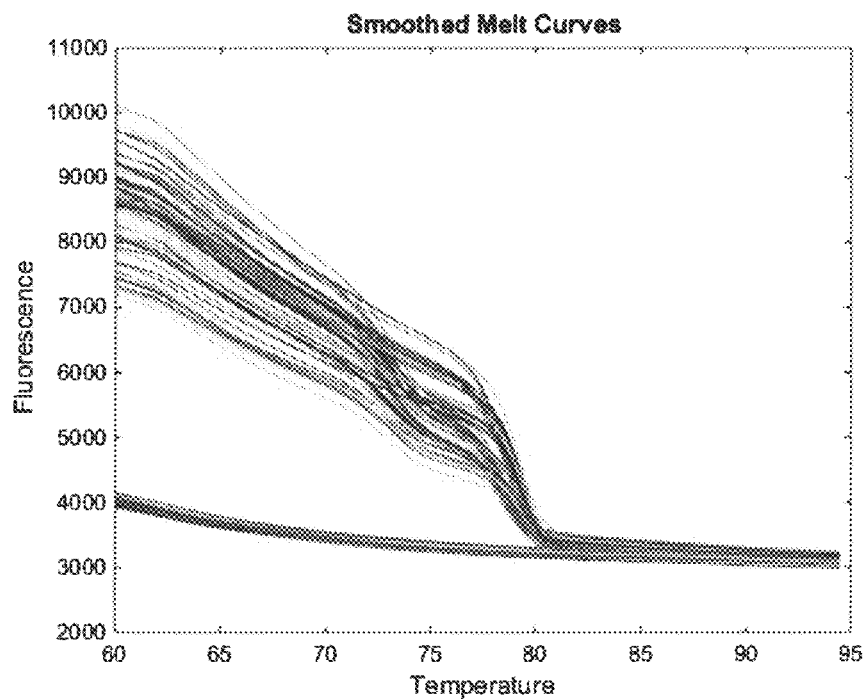

FIG. 30 demonstrates original raw melting curves after smoothing.

Figure 31:
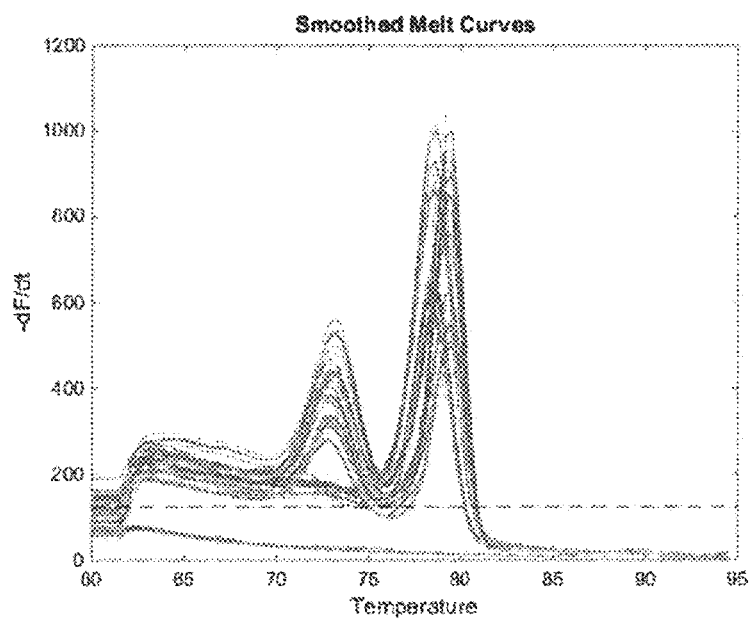

FIG. 31 demonstrates negative derivatives of the smoothed raw melting curves as shown in FIG. 29. The dashed line shows the mean negative derivative of all of the curves.

Figure 32:
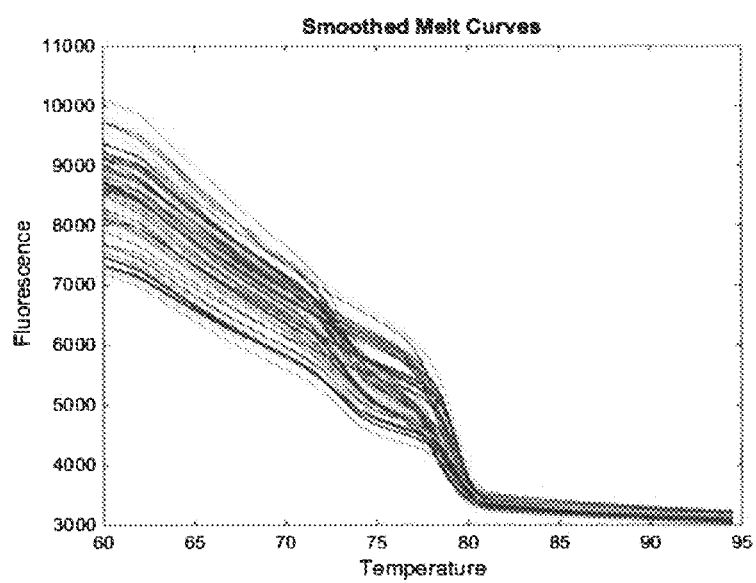

FIG. 32 demonstrates smoothed melting curves with non-active melting curves removed.

Figure 33:
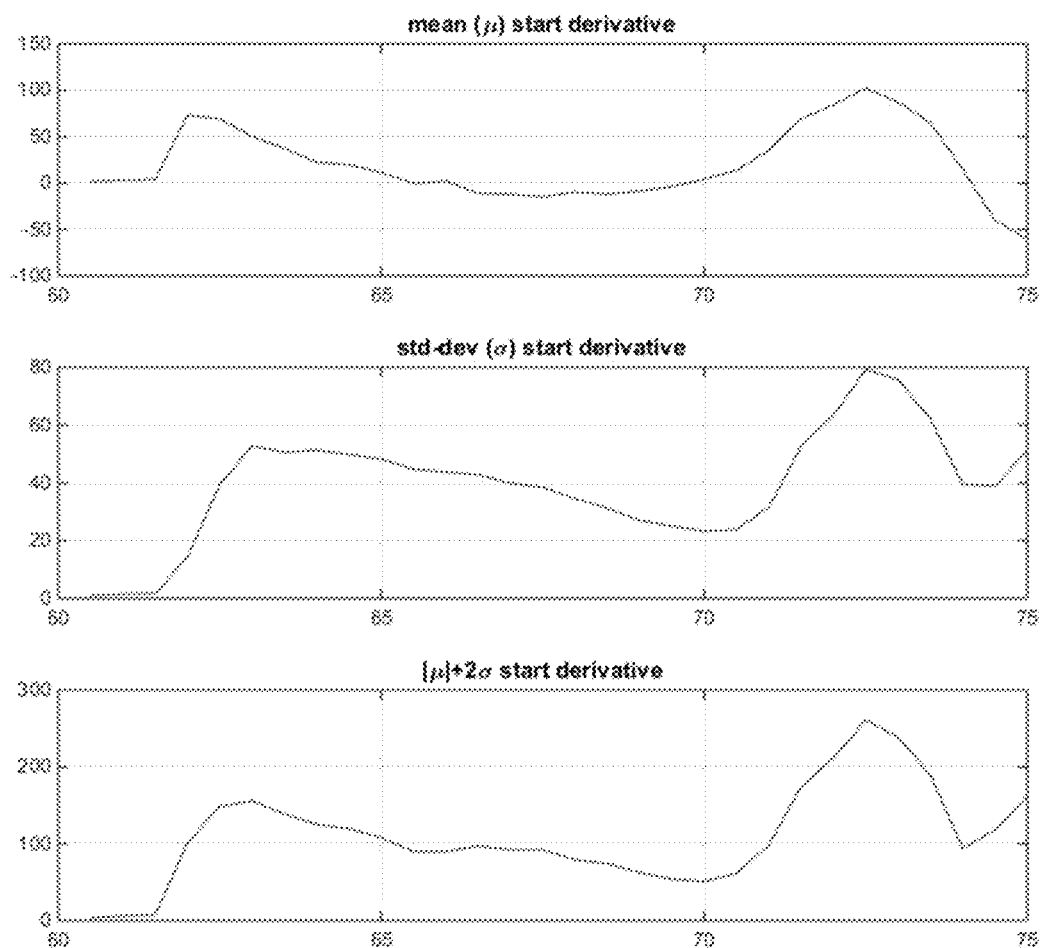

FIGS. 33A-C demonstrate the mean $\mu$, the standard deviation $\sigma$, and combination thereof $|\mu|+2\sigma$ for the normalized negative derivatives of active melting curves, $\mu$ and $\sigma$ being calculated at a plurality of start temperatures from the start temperature search interval.

FIGS. 34A-C demonstrate the mean $\mu$, the standard deviation $\sigma$, and combination thereof $|\mu|+2\sigma$ for the normalized negative derivatives of active melting curves, $\mu$ and $\sigma$ being calculated at a plurality of end temperatures from the end temperature search interval with the start temperature being fixed based on FIG. 33C.

FIGS. 35A-C demonstrate another iteration in calculation of the mean $\mu$, the standard deviation $\sigma$, and combination thereof $|\mu|+2\sigma$ for the normalized negative derivatives of active melting curves, $\mu$ and $\sigma$ being calculated at a plurality of start temperatures from the start temperature search interval with the end temperature being fixed based on FIG. 33C.

Figure 36:
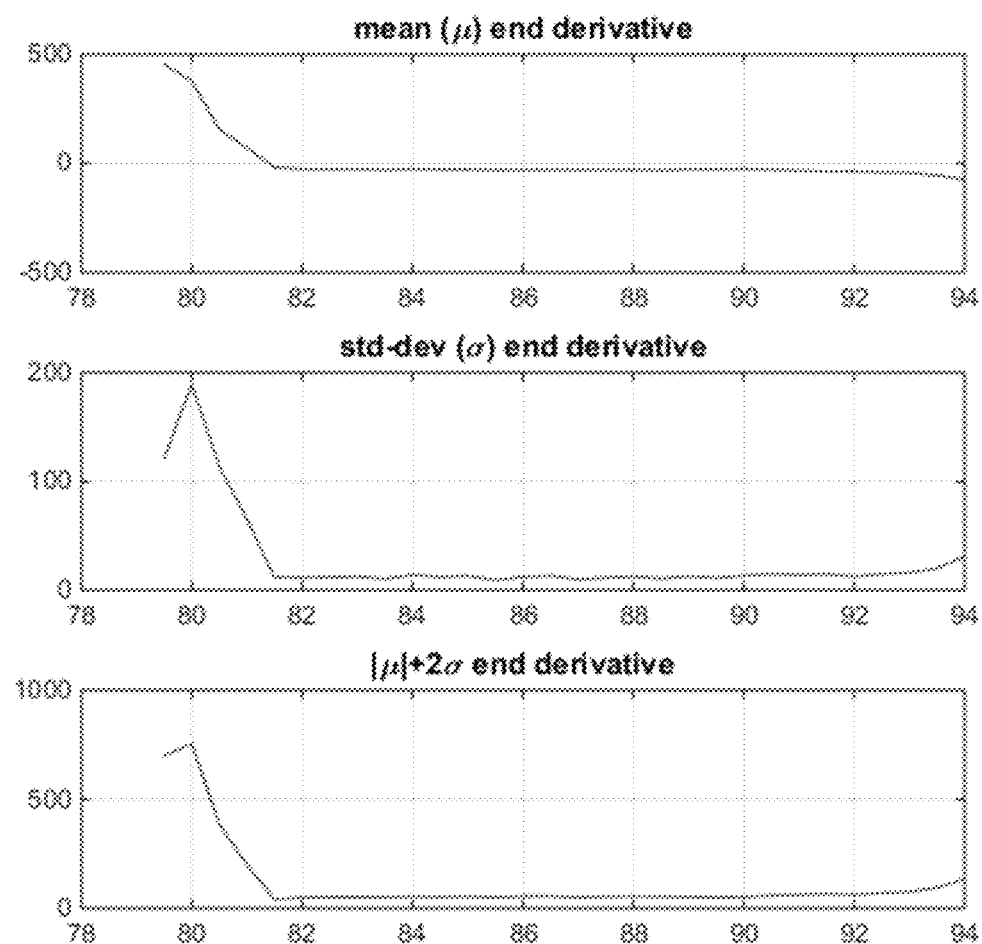

FIGS. 36A-C demonstrate another iteration in calculation of the mean $\mu$, the standard deviation $\sigma$, and combination thereof $|\mu|+2\sigma$ for the normalized negative derivatives of active melting curves, $\mu$ and $\sigma$ being calculated at a plurality of end temperatures from the end temperature search interval with the start temperature being fixed based on FIG. 34C.

Figure 37:
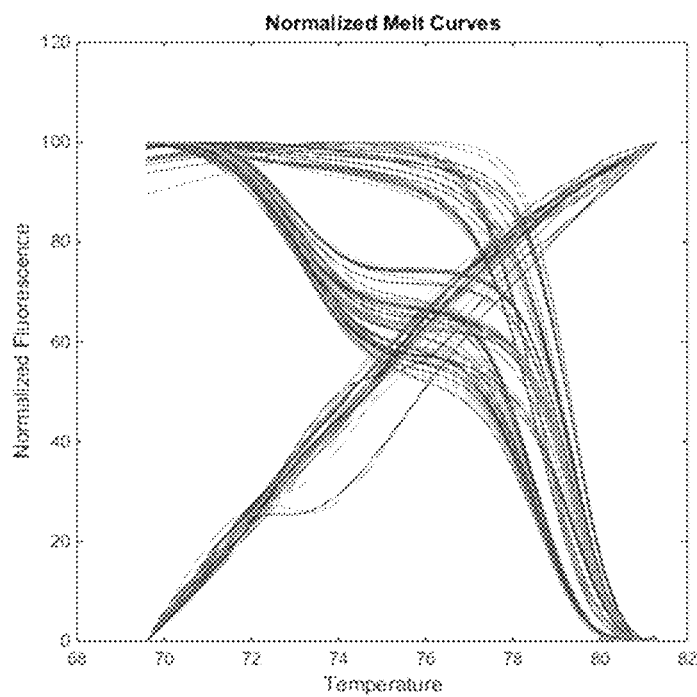

FIG. 37 demonstrates normalized active and non-active melting curves from the detected start and end melt region temperatures.

Figure 38:
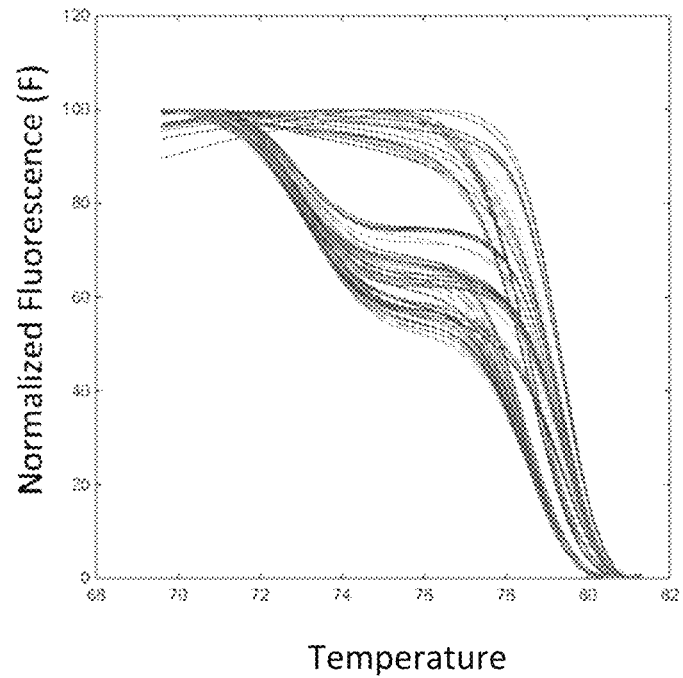

FIG. 38 demonstrates normalized active melting curves from the detected start and end melt region temperatures.

Figure 39:
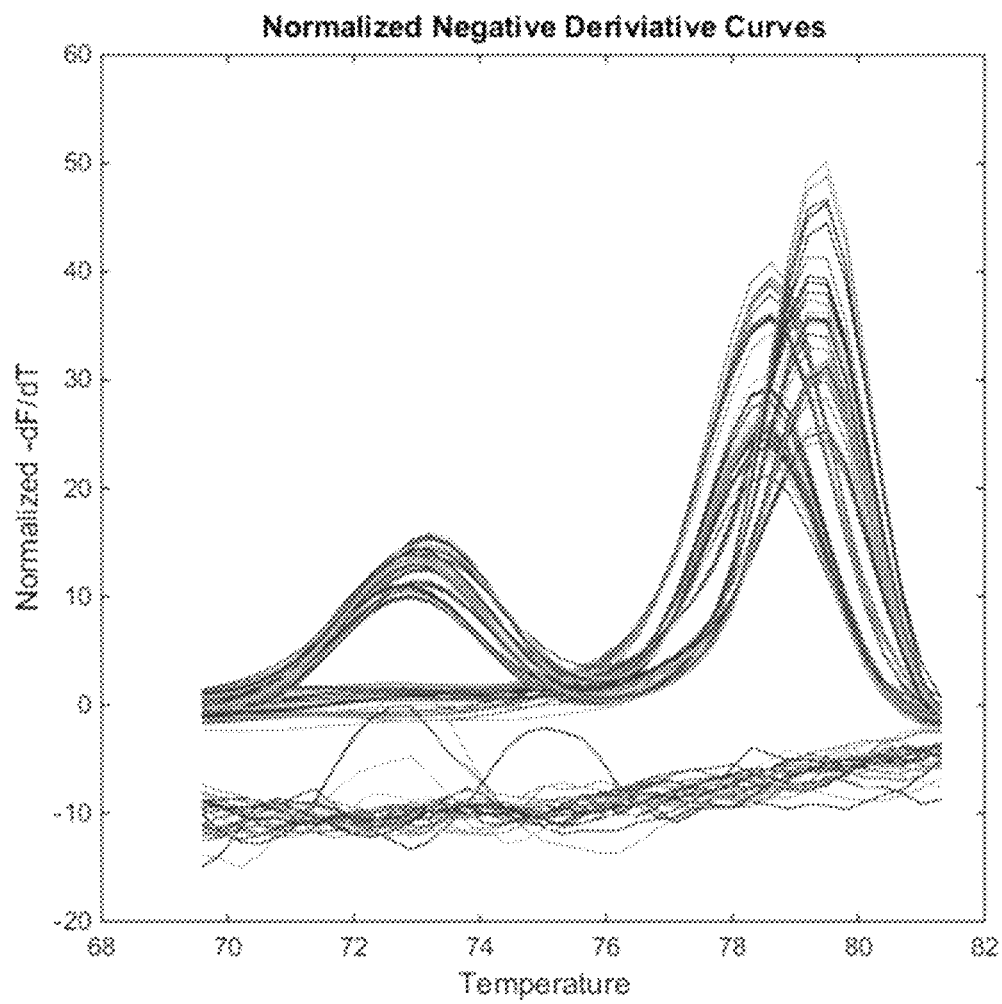

FIG. 39 demonstrates normalized negative derivatives of active and non-active melting curves.

Figure 40:
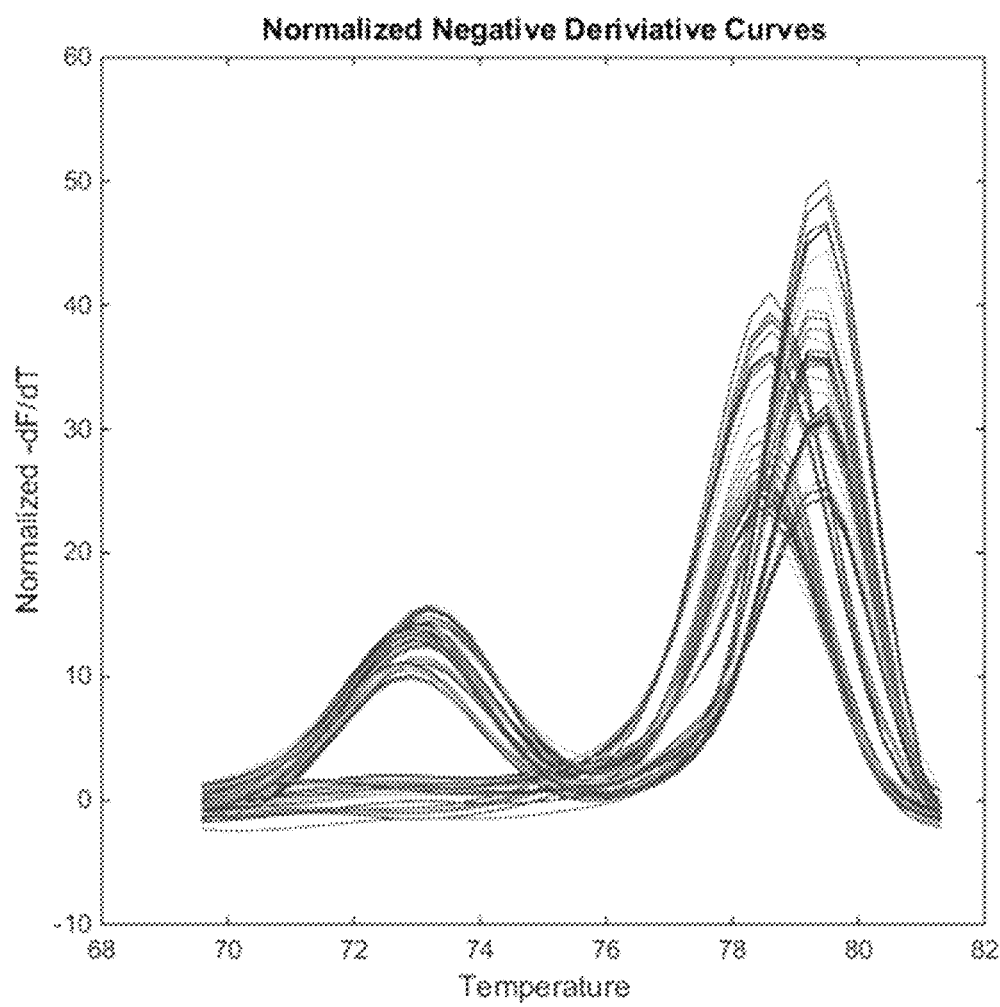

FIG. 40 demonstrates normalized negative derivatives of active melting curves.

Figure 41:
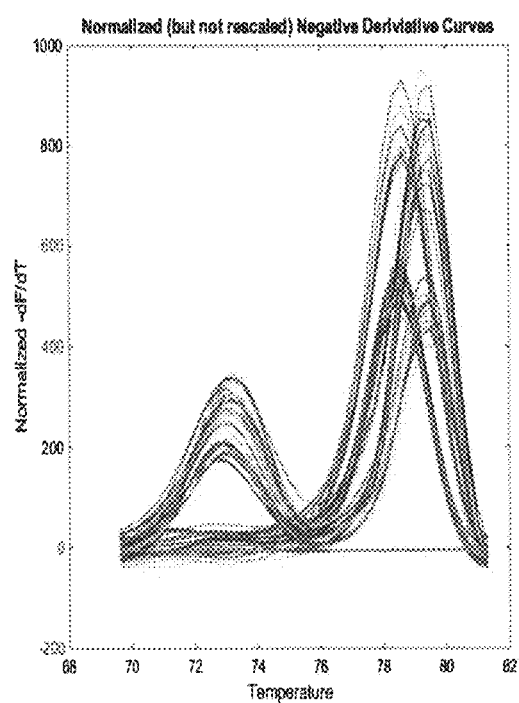

FIG. 41 demonstrates the negative derivative curves without rescaling.

Figure 42:
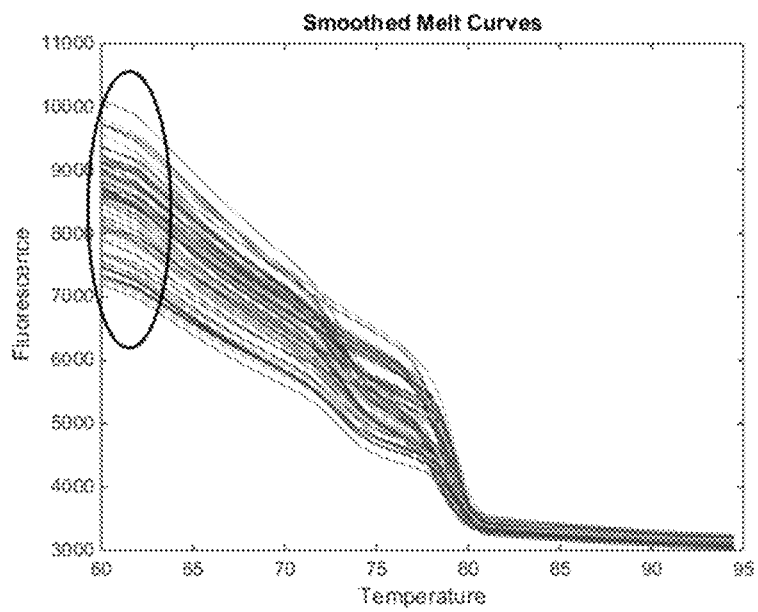

FIG. 42 demonstrates the negative derivative curves without normalization having an unusual kink identified by a circle.

Figure 43:
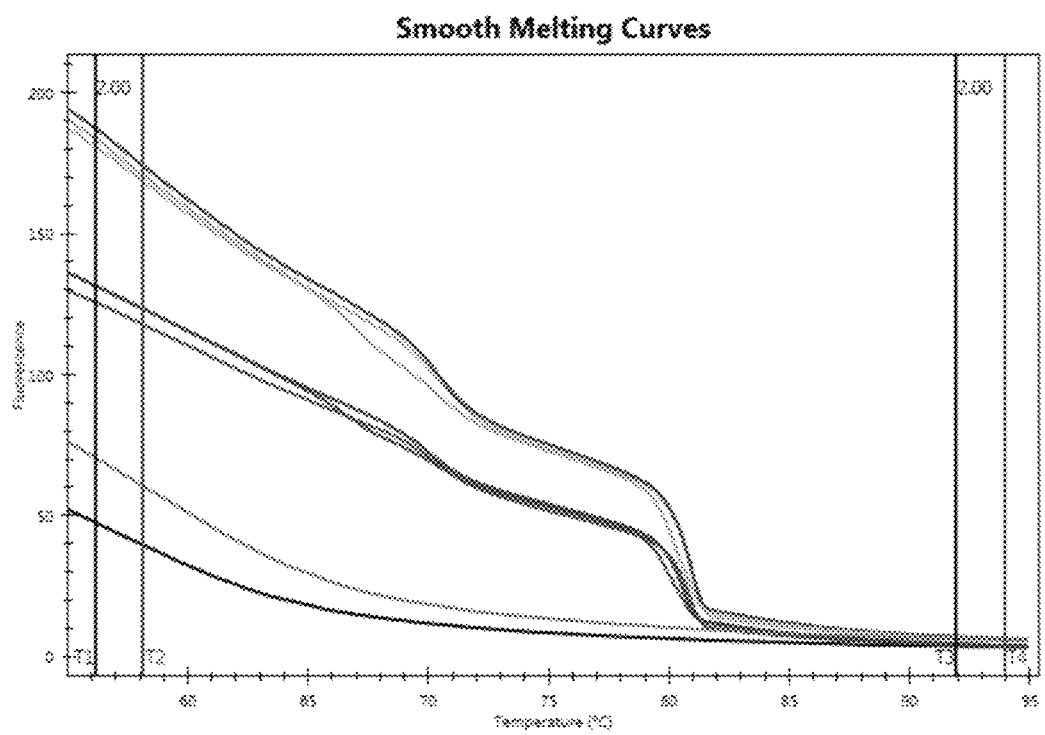

FIG. 43 demonstrates DNA melting curves with four vertical bars defining pre-melt region, a melt region, and a post-melt region.

Figure 34:
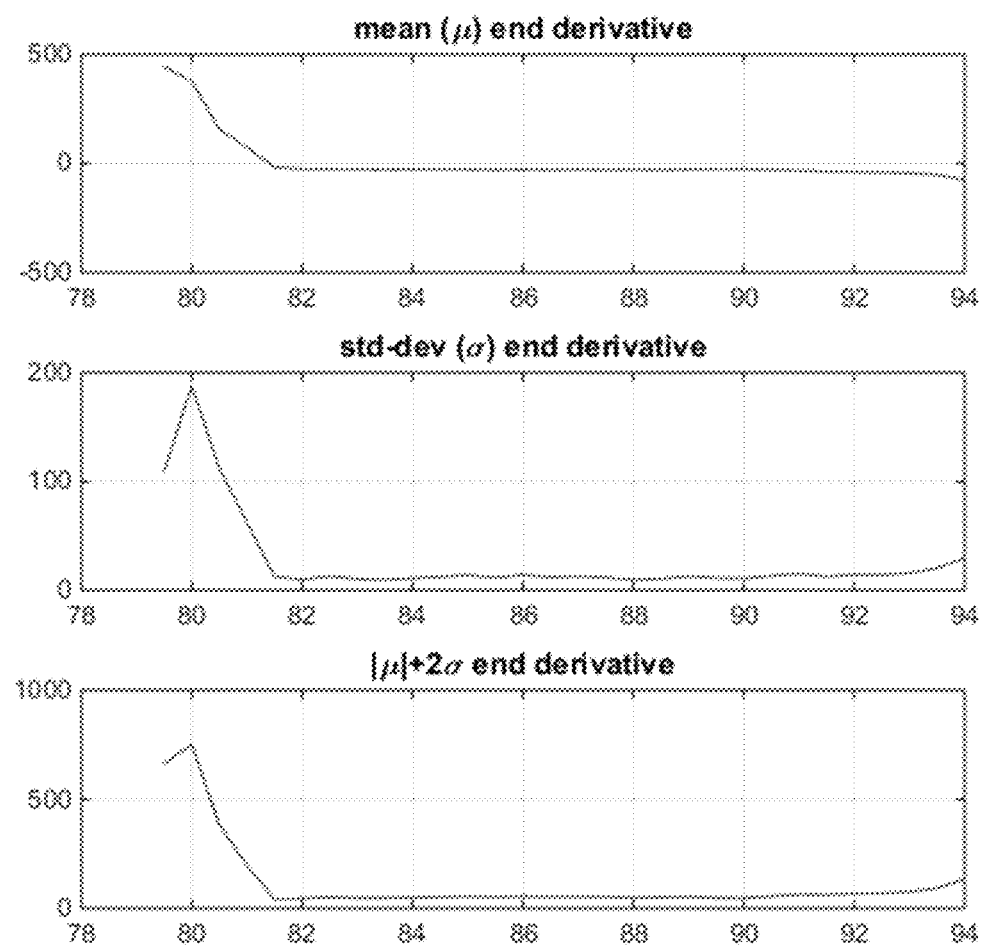
Figure 35:
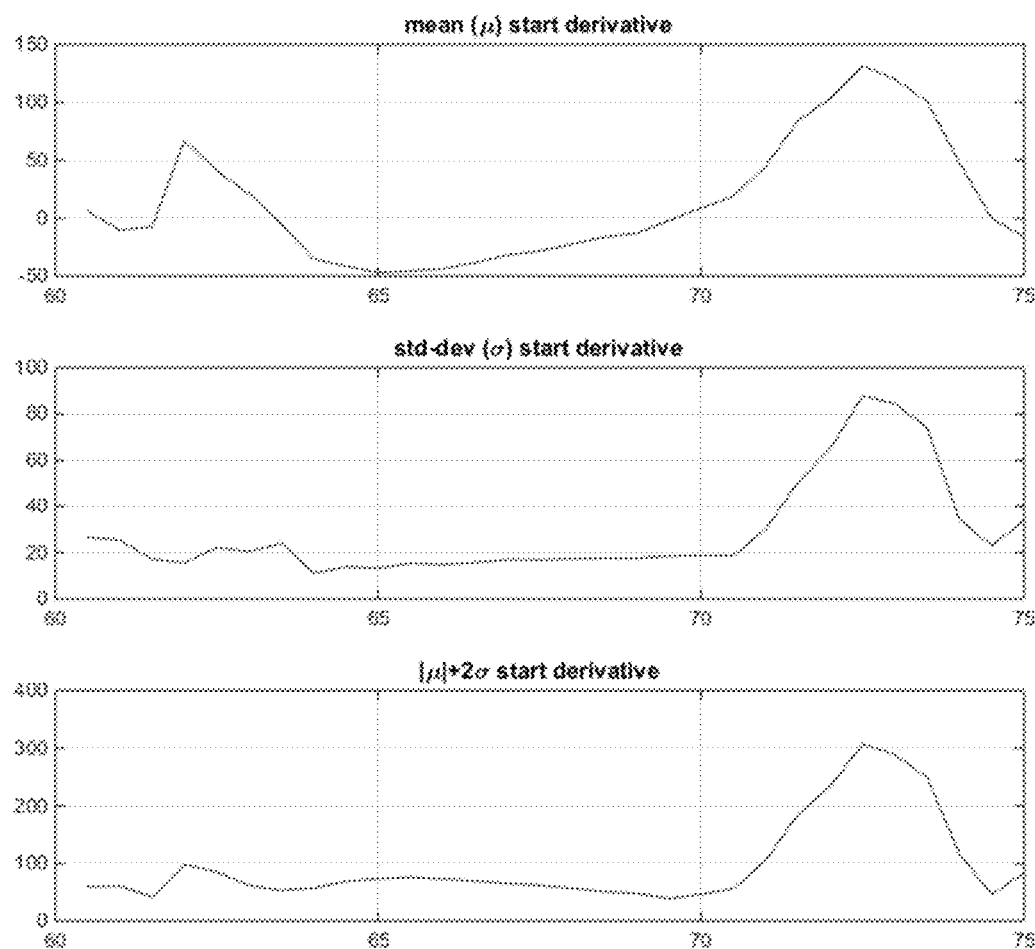
Figure 44:
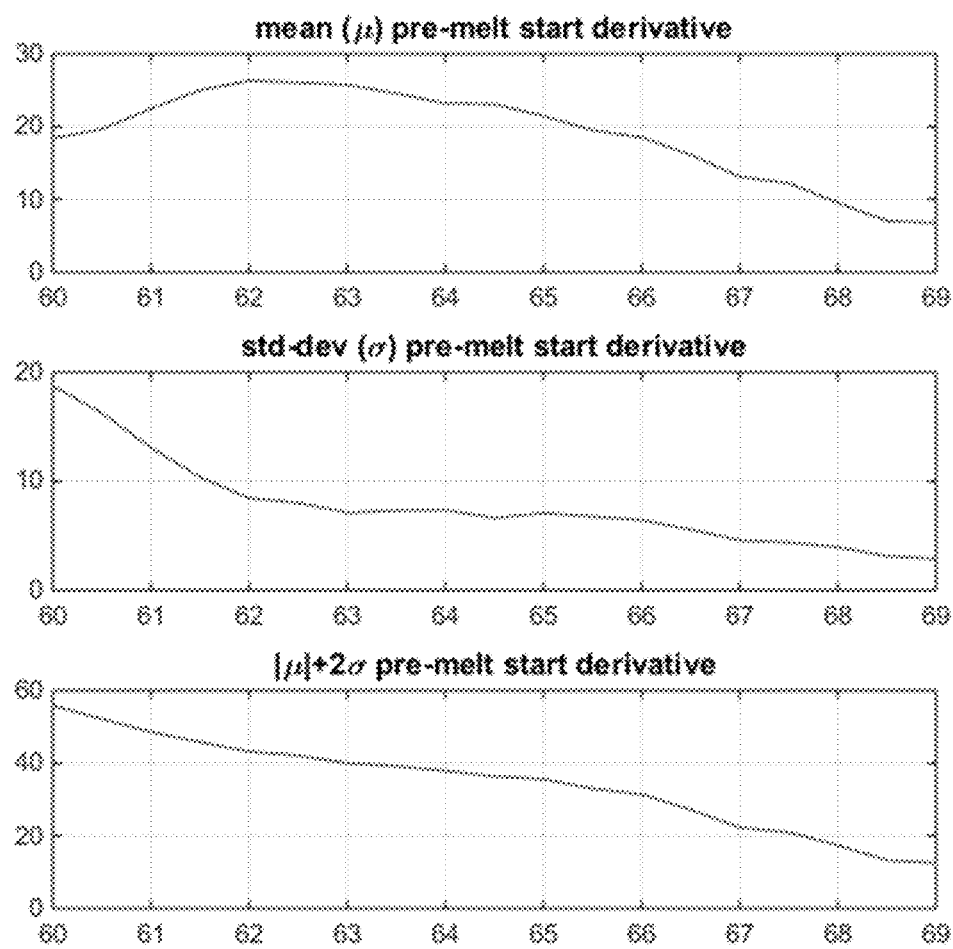

FIGS. 44A-C demonstrate determining the pre-melt start location once start and end temperatures are determined in FIGS. 34 and 35.

Figure 45:
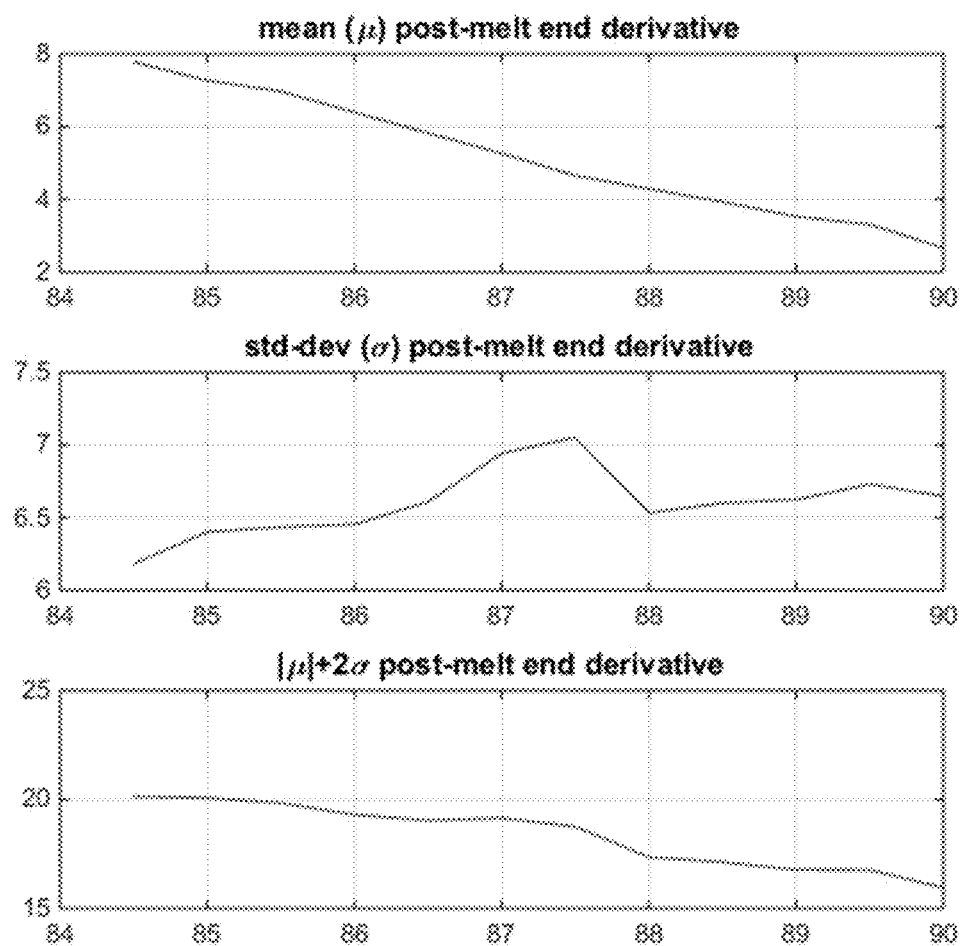

FIGS. 45A-C demonstrate determining the post-melt end location once start and end temperatures are determined in FIGS. 34 and 35.

Figure 46:
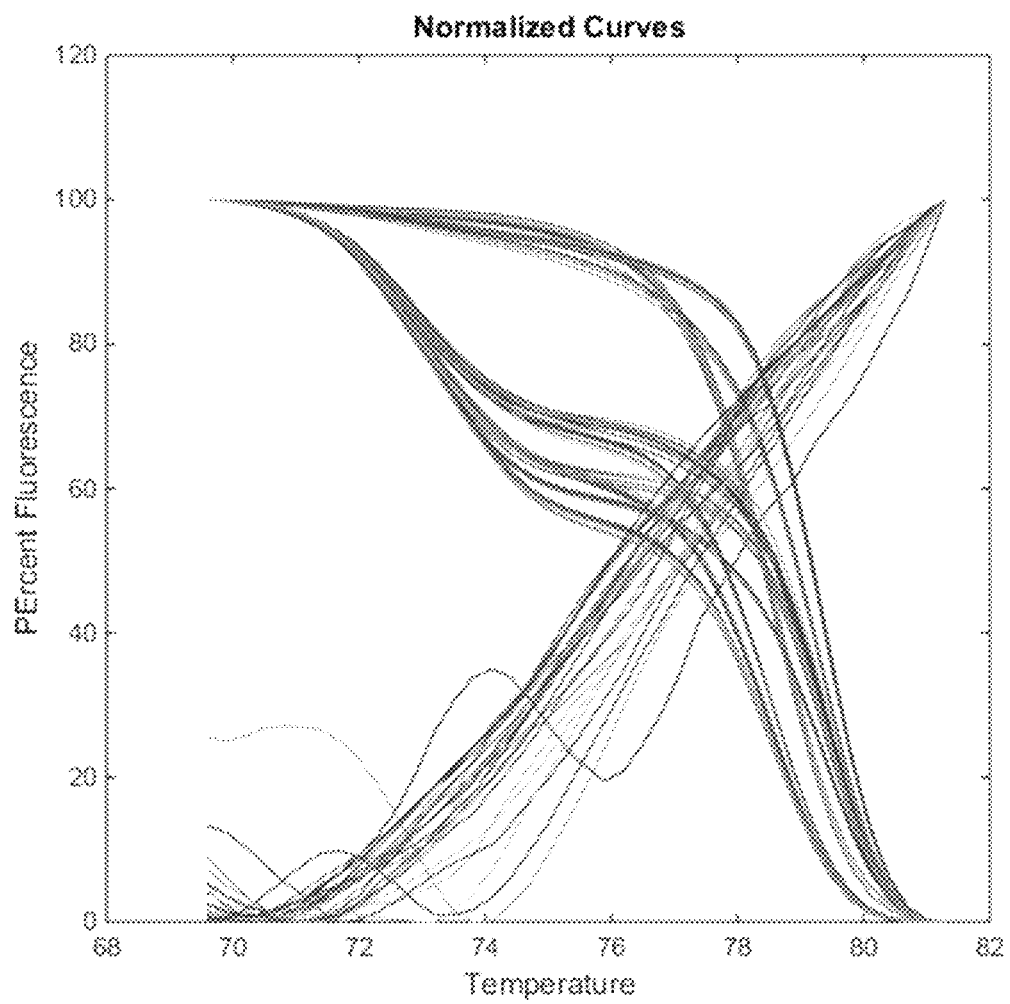

FIG. 46 demonstrates normalized active and non-active melting curves.

Figure 47:
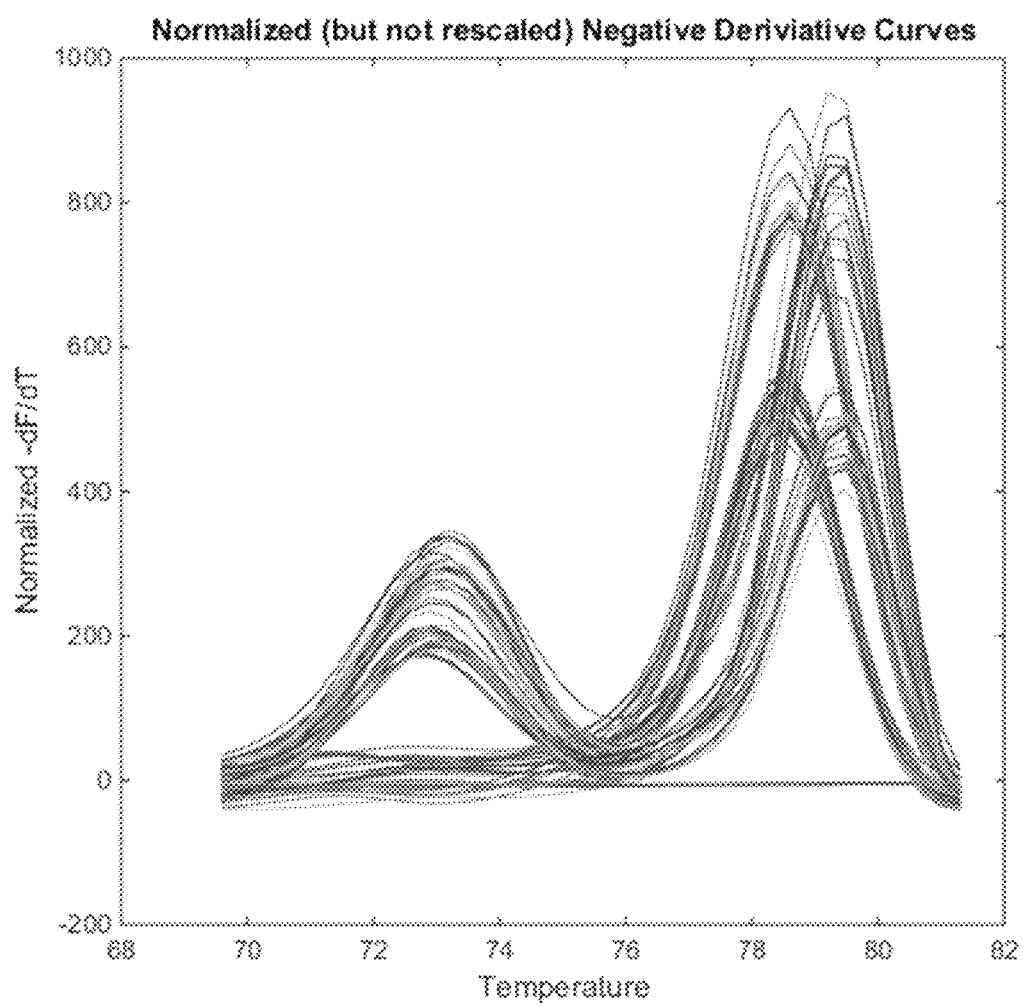

FIG. 47 demonstrates normalized (background removed but not scaled) derivative plots starting and ending near zero.

Figure 48:
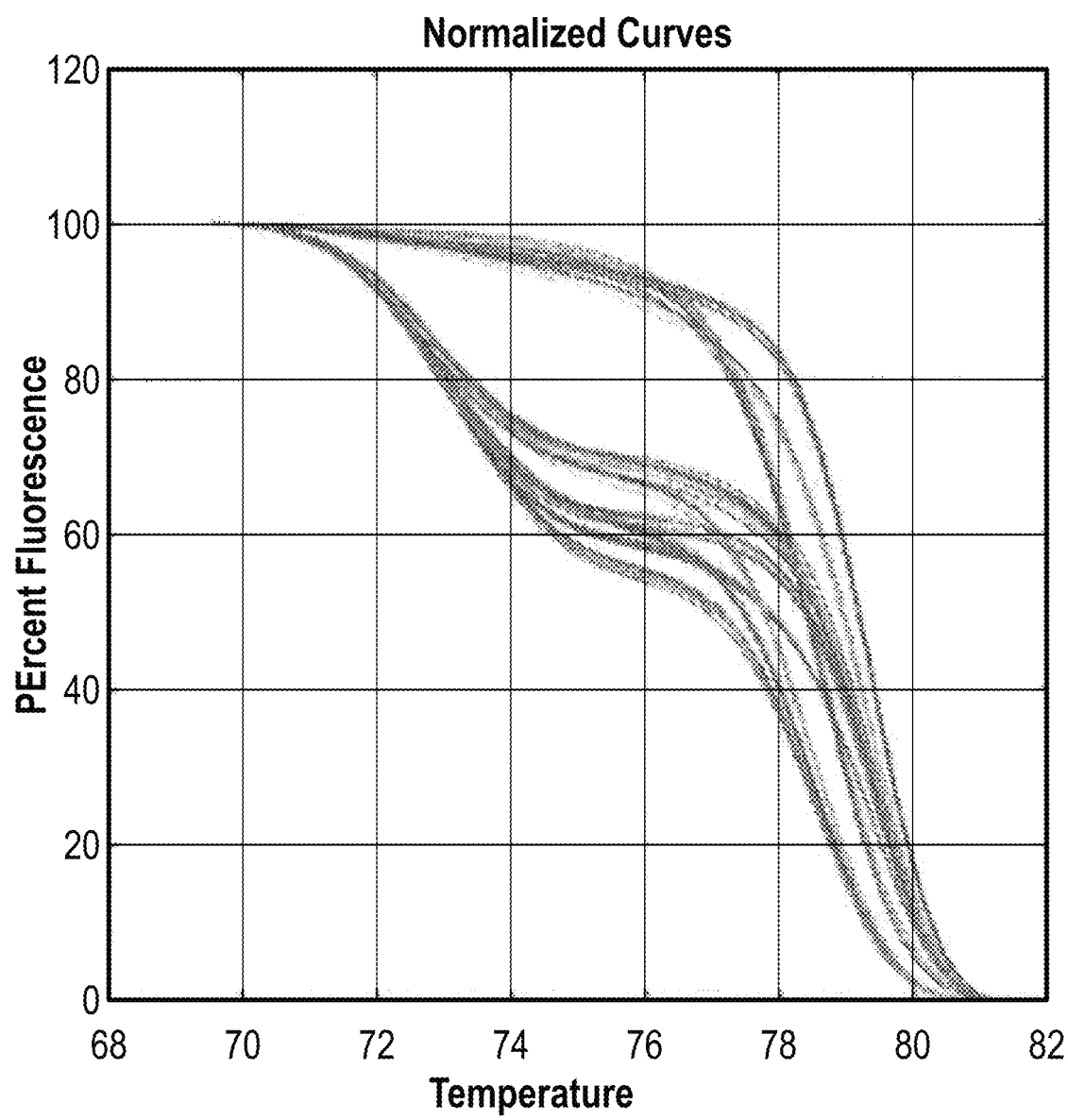

FIG. 48 demonstrates normalized active melting curves.

Figure 49:
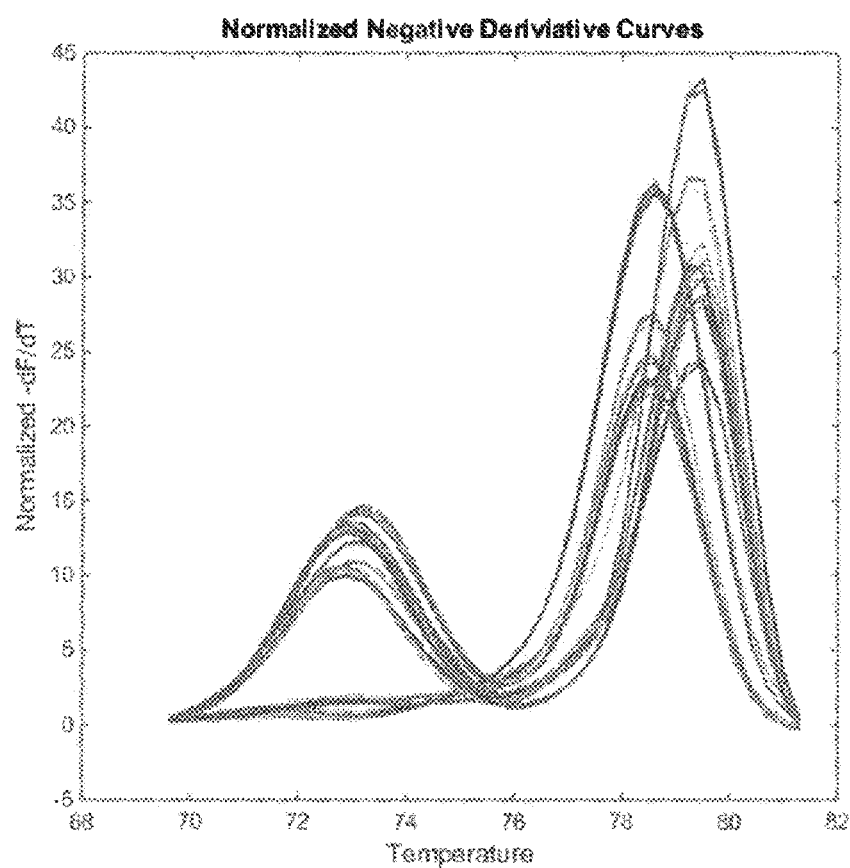

FIG. 49 demonstrates normalized negative derivative of active melting curves.

Figure 50:
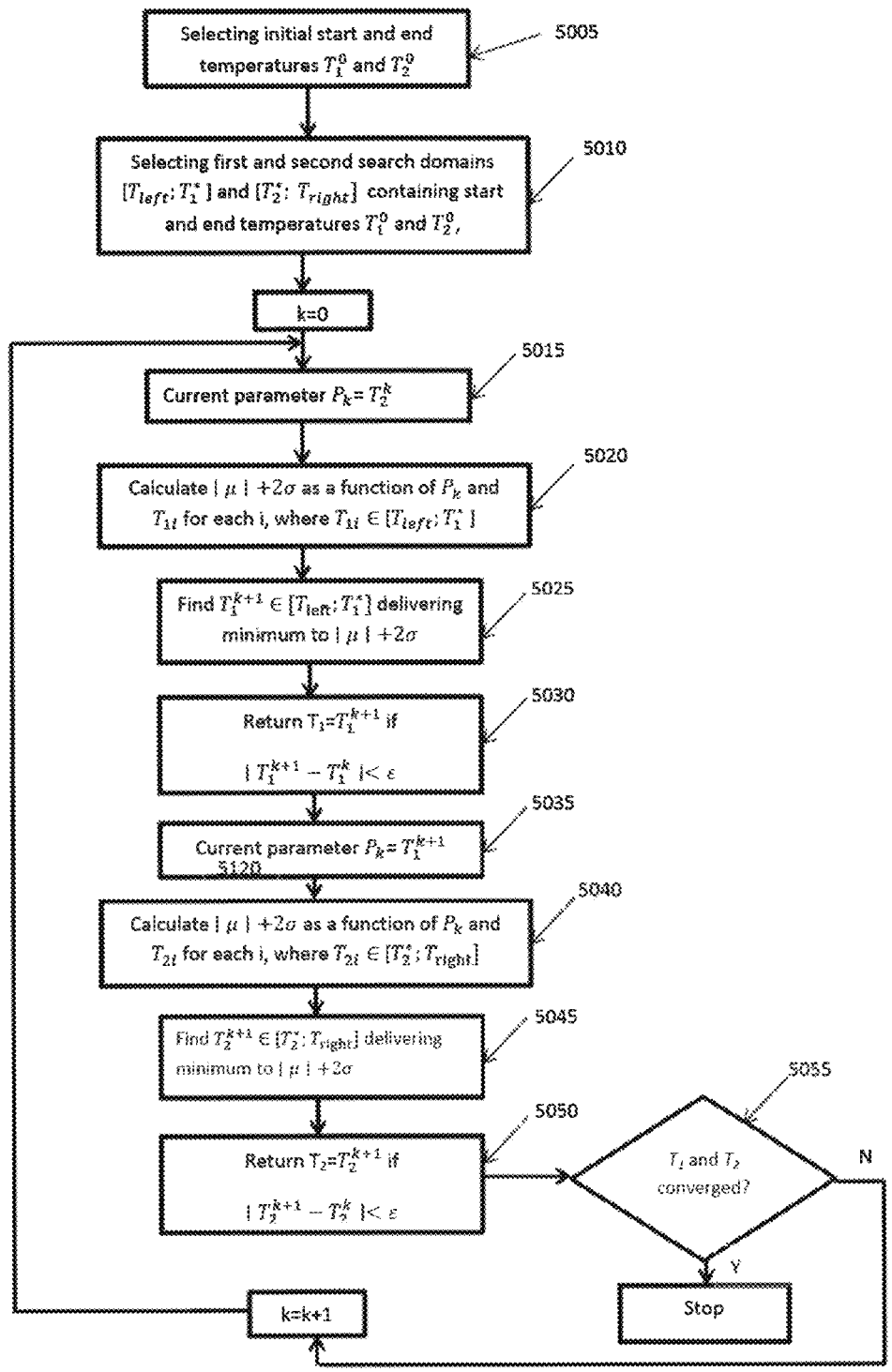

FIG. 50 is a flowchart demonstrating a process for determining a melting range in a melting curve.

Figure 51:
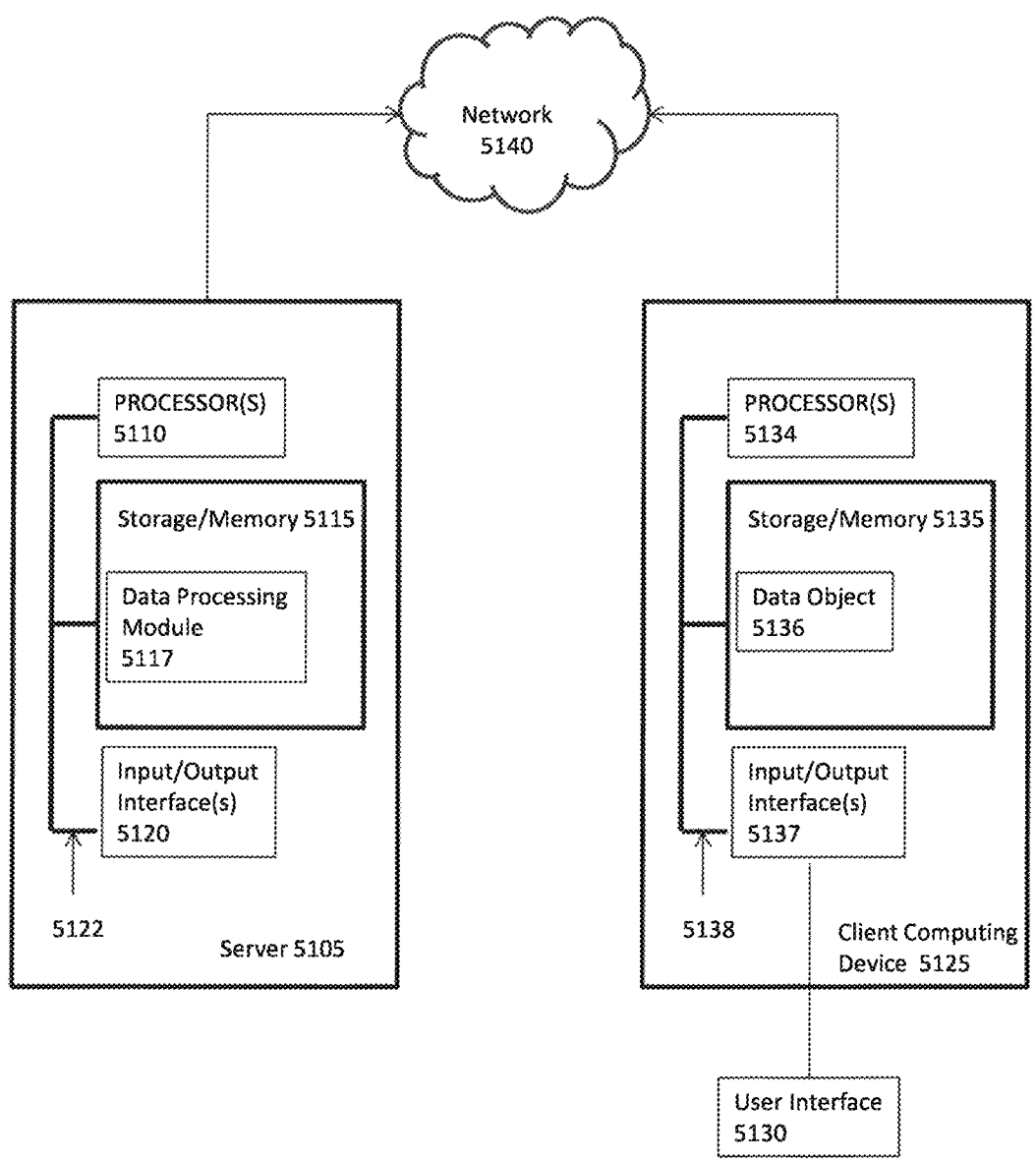

FIG. 51 is a block diagram demonstrating a system for processing experimental curves.

Figure 52:
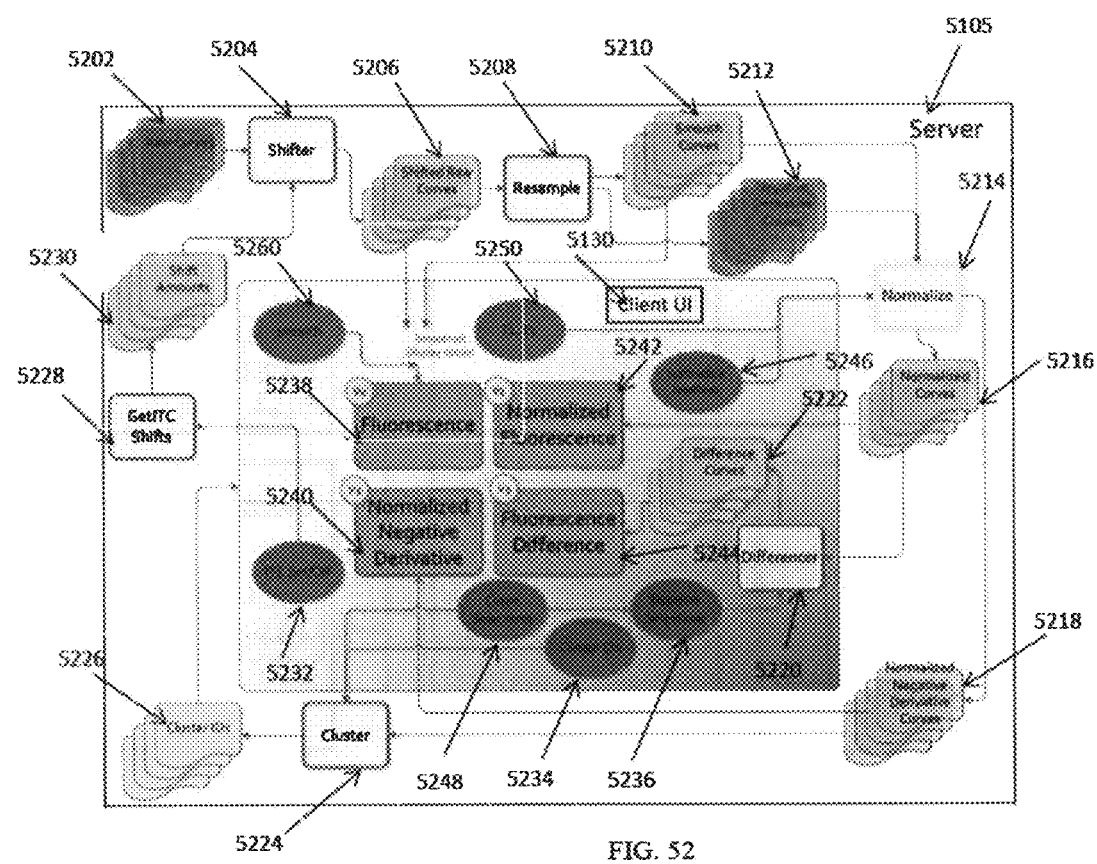

FIG. 52 is a diagram describing an optimized client/server workflow according to the present invention.

FIG. 53A demonstrates user interface (UI) displaying melting curves corresponding to different samples.

FIG. 53B demonstrates UI displaying a well plate corresponding to different samples (melting curves of FIG. 53A).

FIGS. 54A-B demonstrate UI displaying clusters displayed as tree views.

FIGS. 55A-E demonstrates UI displaying smooth melt curves, normalized curves, derivative curves, difference curves, and the side panel.

Figure 56:
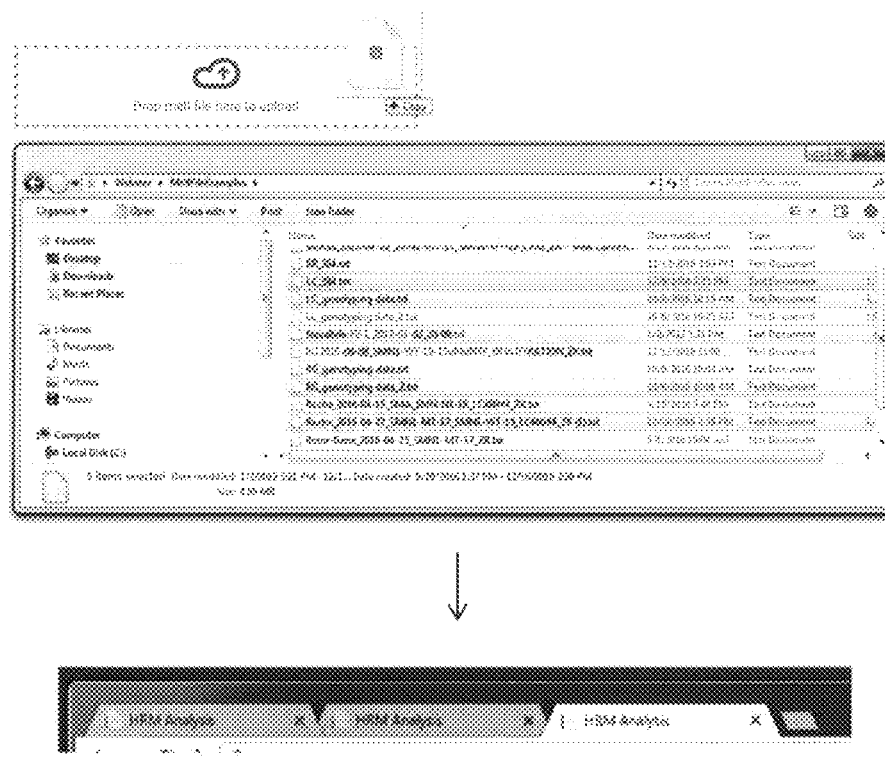

FIG. 56 demonstrates multiple melt files dragged and dropped or selected which will open multiple analysis tabs automatically.

FIGS. 57A-B demonstrates a circular plate before and after selecting sample wells according to one embodiment of the present invention.

FIGS. 58A-B demonstrates a circular plate before and after selecting sample wells according to another embodiment of the present invention.

DETAILED DESCRIPTION OF PREFERRED EMBODIMENTS

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

An apparatus and system for identifying and characterizing a nucleic acid in a sample including at least one unknown nucleic acid is provided. Methods directed to processing and analysis DNA melting curves according to the present invention can be performed at a plurality of different platforms (devices). Each device includes a DNA vessel having one or more DNA samples. The DNA vessel can be in the form of a well, tube, chamber, or channel. The DNA vessel is in communication with a temperature control system and an imaging system. The temperature in the one or more DNA samples is ramped by the temperature control system to achieve DNA denaturing. One or more DNA melting curve is generated for the plurality of samples by using the imaging system to measure fluorescence as a function of temperature.

An example of a suitable system in accordance with some aspects of the invention is illustrated in connection with FIG. 2. As illustrated in FIG. 2, system 100 may include a microfluidic device 102. Microfluidic device 102 may include one or more microfluidic channels 104 each having a heating element, the temperature of which is selectively configurable using one or more heating parameters. In one embodiment, the one or more heating parameters may be predetermined and set in advance by control application. In another embodiment, the one or more heating parameters may be selectively calculated and determined in response to data derived from one or more reactions chemical and/or physical reactions occurring or which have occurred on a sample contained in the respective microfluidic channels 104. In the examples shown, device 102 includes two microfluidic channels, channel 104a and channel 104b each of them including a respective heating element and able to receive one or more samples thereon and support various reaction processing on the samples contained therein. Although only two channels are shown in the exemplary embodiment, it is contemplated that device 102 may have fewer than two or more than two channels. For example, in some embodiments, device 102 includes eight channels 104.

In one embodiment, device 102 may include a single DNA processing zone 131 in which DNA amplification occurs prior to high resolution thermal melt processing which yields a dynamic signal such as a melt curve showing the relationship of fluorescence intensity level and temperature. In the DNA processing zone 131, a control application selectively controls a temperature of the respective heating element within the zone according to parameters specific to the type of reaction occurring at a given time. For example, during amplification, a temperature of the heating element in at a first time period may be different from a temperature at a second time period when melt processing is occurring. In operation and during DNA processing, a series of pumps is selectively controlled by an edge control algorithm which controls the flow of blanking fluid through the one or more channels 104. The edge control system, in real-time, ensures that that the sample being processed remains within a specified region of interest (ROI) so that appropriate temperature changes can be applied by the heating elements within respective channels and fluorescence levels can be captured.

In another embodiment, device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 2, PCR zone 131 includes a first portion of channels 104 and melt zone 132 includes a second portion of channels 104, which is downstream from the first portion. In these zones, a control application selectively controls a temperature of the respective heating element (also referred to herein as heating channel) within the respective zones 131 and 132 according to parameters specific to the type of reaction occurring in the respective zones 131 and 132. For example, a temperature of the heating element in the DNA amplification zone 131 may be set differently from a temperature of the DNA melt zone 132.

In operation and during DNA processing, a series of pumps is selectively controlled by an edge control algorithm which controls the flow of blanking fluid through the channels 104. The edge control system, in real-time, ensures that that the sample being processed remains within a specified region of interest (ROI) so that appropriate temperature changes can be applied by the heating elements within respective channels and fluorescence levels can be captured.

In one embodiment, the device 102 may also include a sipper 108. Sipper 108 may be in the form of a hollow tube. Sipper 108 has a proximal end that is connected to an inlet 109 which inlet couples the proximal end of sipper 108 to one or more channels 104. Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the one or more channels 104, system 100 may include a well plate 196 that includes a plurality of wells 198, at least some of which contain a sample solution (e.g., a solution containing a DNA sample). In the embodiment shown, well plate 196 is connected to a positioning system 194 which is connected to a main controller 130.

Main controller 130 is a central processing unit and includes hardware for performing a plurality of calculations and controlling the complete operational aspects of apparatus 100 and all components therein. Positioning system 194 may include a positioner for positioning well plate 196, a stepping drive for driving the positioner, and a positioning controller for controlling the stepping drive.

To introduce a sample solution into the one or more channels 104, the positioning system 194 is controlled to move well plate 196 such that the distal end of sipper 108 is submerged in the sample solution stored in one of the wells 198. FIG. 2 shows the distal end of 108 being submerged within the sample solution stored in well 198n. In order to force the sample solution to move up the sipper and into the channels 104, a vacuum manifold 112 and pump 114 may be employed. During DNA processing, the pump 114 is controlled by an edge control algorithm which controls the flow of blanking fluid through one or more channels 104 by monitoring the edge of the blanking fluid at separate imaging location 132 or alternatively within the processing zone 131. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into one or more channels 104. Additionally, this causes the reagents in wells 106 and 105 to flow into a channel. Accordingly, pump 114 functions to force a sample solution and real-time PCR reagents to flow through one or more channels 104. In operation where there is a single DNA processing zone 131, PCR occurs first followed by melt processing. In another embodiment having two separate DNA processing zones, melt zone 132 is located downstream from PCR zone 131. Thus, in this embodiment, a sample solution will flow first through the PCR zone and then through the melting zone. In embodiments having a single DNA processing zone, the sample solution will flow through the DNA processing zone 131 where it will undergo PCR and HRM, with a leading edge of the sample solution entering a separate imaging location 132. The embodiments having a single DNA processing zone are described in details in US Patent Application No. 2014/0272927 which is incorporated by reference herein in its entirety.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. In order to achieve PCR for a DNA sample flowing through the processing zone (or PCR zone) or single DNA processing zone 131, the temperature of the sample must be cycled, as is well known in the art. Accordingly, in some embodiments, system 100 includes a temperature control system 120. The temperature control system 120 may include a temperature sensor, a heater/cooler (e.g. heater elements or heater channels), and a temperature controller. In some embodiments, a temperature control system 120 is interfaced with main controller 130 so that main controller 130 can control the temperature of the samples in DNA processing zone 131 during PCR and during melt analysis (or when flowing through the PCR zone 131 and the melting zone 132). Main controller 130 may be connected to a display device for displaying a graphical user interface. Main controller 130 may also be connected to user input devices 134, which allow a user to input data and commands into main controller 130.

To monitor the PCR process and the melting process that occur in the single DNA processing zone 131 (or when two zones are present, PCR zone 131 and melt zone 132, respectively), system 100 may include an imaging system 118. Imaging system 118 may include an excitation source, an image capturing device, a controller, and an image storage unit.

The genetic analyzer device outputs data representing a melt curve showing the level of fluorescence at given temperatures. From the melt curve characteristics, various properties of the nucleic acid sample which underwent melt processing can be determined. However, to improve interpretation, it is advantageous to normalize the curve and subtract background data (e.g. information that is unrelated to the DNA melt reactions) from the set of data used to generate the melt curve or the negative derivate of the melt curve. A background identification algorithm according to invention principles uses raw melt curve data to identify reactions that are unrelated actual DNA melt reactions.

To achieve this goal, the device executes a melt processing algorithm which controls the components discussed above to perform melt processing on a plurality of samples in individual channels of a microfluidic device 102. The main controller 130 causes data representing a fluorescence level over a period time at different temperature levels to be output as a melt curve which shows this relationship. By analyzing the melt curve, at least one characteristic of the nucleic acid can be identified. In one embodiment, the at least one characteristic is one of a type of nucleic acid and a genotype of the nucleic acid. This characteristic determination is based on the temperature at which the fluorescence level drops indicating denaturation of the nucleic acid at that temperature. These values can be compared to known value to identify the at least one characteristic. To improve the ability of the device to identify the characteristic associated with the sample, a background identification algorithm can be applied to the data derived during melt processing prior to generating the melt curve from which information about a characteristic of a nucleic acid will be determined. In certain embodiments, the clustering algorithm may be embodied as any one of an executable application and a module, or a combination of both. Further, the remaining description may use the terms algorithm, application and/or module interchangeably but each refers to a set of instructions stored on a storage device (memory) that when executed by one or more controllers or central processing units, operate to control various elements of the system to act in a desired manner to achieve a desired goal.

The background identification algorithm advantageously improves the quality of information being conveyed by the melt curves that are generated during a single melt processing run on a particular microfluidic device by ensuring that background information (e.g. information relating to reactions other than DNA melt reactions) is removed during a normalization process. FIG. 3 illustrates additional hardware embodied within the system 100 shown in FIG. 1 that act on or are controlled by the execution of the clustering algorithm.

The main controller 130 includes one or more central processing units which are hardware circuits that executing instructions stored in one of memory 140, RAM 150 or ROM 160. The main controller 130 may include a central processing unit (CPU), one or more general-purpose microprocessor(s), application-specific microprocessor(s), and/or special purpose microprocessor(s), or some combination of such processing components. The main controller 130 may retrieve the instructions from the memory 140, RAM 150 and/or ROM 160, an internal register, or an internal cache. The main controller 130 then decodes and executes the instructions. Then, the main controller 130 writes one or more results to the storage device 140, RAM 150, the internal register, or the internal cache. The main controller 130 may provide the processing capability to execute the operating system, programs, user and application interfaces, and any other functions of the device 100.

In one embodiment, the background identification algorithm is embodied as a background identification application and may be stored in one of storage device 140 and be selectively executed by the main controller 130 to load, into specifically addressed sectors of RAM 150 (or other work area memory) the instructions for estimating information from an original melt curve representative of background reactions for removal therefrom when generating a normalized melt curve.

In a first embodiment, the background identification algorithm employs an iterative technique using mixture model for modelling melt fluorescence. In this embodiment, the mixture model used is derived from the Van't Hoff equation and hereinafter will be referred to as the Van't Hoff Mixture Model or Mixture Model. The mixture model is described in more details in a provisional application 62/353,602, filed on Jun. 23, 2016, which is incorporated herein by reference.

The mixture model employed to model the raw fluorescence curve assumes that there are M or fewer independent reactions that influence the fluorescence, and the total observed fluorescence is a mixture of these individual effects. Some embodiments of the mixture model can be described mathematically as follows:

$$F_{total}(T; \Theta) = \sum_{i=1}^{M} \alpha_i F_i(T; \Theta_i) \text{ such that} \quad (19)$$

$$\sum_{i=1}^{M} \alpha_i = 1 \text{ and } \alpha_i \geq 0 \text{ for all } i,$$

where $F_{total}(T)$ is the total fluorescence (and should match the observed data if the model is good), where $F_i(T; \Theta_i)$ is the fluorescence of the $i^{th}$ reaction as a function of temperature, where $\Theta_i$ is the set of parameters for the $i^{th}$ fluorescence model, where the mixture coefficient $\alpha_i$ is the contribution of $F_i(T;\Theta_i)$ (mixture coefficient $\alpha_i$ is also referred to as "contribution $\alpha_i$," and $F_i(T;\Theta_i)$ is also referred to as "model i") to the total model (mixture coefficient $\alpha_i$ is the weight factor of model i to the total reaction), and where $\Theta$ is the collection of all parameters $\{\alpha_i, \Theta_i : i \in 1, \ldots, M\}$. Furthermore, the constraints indicate that each model has some non-negative contribution to the total and that individual model contributions sum to 1. And a mixture model that is based on the Van't Hoff equation (the Van't Hoff equation forms the basis of $F_i(T; \Theta_i)$, which is the fluorescence profile of independent reaction i to the overall fluorescence) is referred to herein as the Van't Hoff mixture model.

The previous description presents a melt model that had two parameters: the melting temperature $T_m$ and the total enthalpy change $\Delta H$ of the reaction. Thus, for M reactions, the embodiments have 3M−1 parameters, including the M−1 choices for the contribution $\alpha_i$ values (note that the constraint fixes one contribution $\alpha_i$ value given the other values).

Additionally, if the background dye fluorescence is also a reversible reaction, and if the ITC is a reversible reaction, then a homozygous (Wild-type and variant) genotype will require M=3, and a heterozygous genotype will require M=4 (or more). Thus, for 4 reactions the model requires the determination of 11 parameters (2 for each reaction model and a mixture coefficient for each reaction model, where the last reaction mixture coefficient can be determined from the others because they all sum to 1).

Furthermore, consider some other common reactions that possibly affect the fluorescence. For example, the unbound fluorescence dye itself may be involved in a reversible reaction whereby the level of fluorescence changes before and after the reaction. Additionally, some parts of the solution may be relatively inert, so their fluorescence is unaffected by temperature. Other reactions may be irreversible. Below is a summary of some possible reaction models:

TABLE 1

| Reaction | Example | Fluorescence Model F(T) | Parameters |
|---|---|---|---|
| DNA double-stranded to single-stranded type-2 | AA' ⇌ A + A' | $F(T) = \dfrac{4 + h(T) - \sqrt{h^2(T) + 8h(T)}}{4}$ $h(T) = \exp\left[\dfrac{\Delta H}{R}\left(\dfrac{1}{T_m} - \dfrac{1}{T}\right)\right]$ | $\Delta H$ and $T_m$ |
| Single agent change type-1 | B ⇌ C | $F(T) = \dfrac{1}{1 + h(T)}$ $h(T) = \exp\left[\dfrac{\Delta H}{R}\left(\dfrac{1}{T_m} - \dfrac{1}{T}\right)\right]$ | $\Delta H$ and $T_m$ |
| No reaction (inert) type-0 | D ⇌ D | $F(T) = 1$ | None |
| Irreversible reaction type NR | E → F | $F(T) = e^{-T^2/2(T_m)^2}$ | $T_m$ |

The individual reactions that take place during the melting of a calibration product include at least two reactions for the two sequences and one reaction for the background product, which includes any remaining primers or other product. Each individual reaction is mathematically expressed as an individual Van't Hoff term. For DNA, a synthetic DNA sequence, or any product AA' that reversibly forms two separate products A and A' when heated (or AA' ⇌ A+A'), the Van't Hoff term can be described as follows:

$$F(T) = \frac{4 + h(T) - \sqrt{h^2(T) + 8h(T)}}{4}, \text{ and}$$

$$h(T) = \exp\left[\frac{\Delta H}{R}\left(\frac{1}{T_m} - \frac{1}{T}\right)\right].$$

where $\Delta H$ is the total enthalpy change, R is the ideal gas law constant, and $T_m$ is the melting temperature of the product AA'.

For the background product that is assumed to reversibly form a product C from B when heated (B ⇌ C), the Van't Hoff term can be described as follows:

$$F(T) = \frac{1}{1 + h(T)},$$

$$h(T) = \exp\left[\frac{\Delta H}{R}\left(\frac{1}{T_m} - \frac{1}{T}\right)\right],$$

where $\Delta H$ is the total enthalpy change, R is the ideal gas law constant, and $T_m$ is the melting temperature of the background product. The melting temperature $T_m$ and the total enthalpy change $\Delta H$ can be calculated by fitting a parametric model with respect to the obtained denaturation data.

Several approaches to estimate the parameters of the model exist. For example, one of these approaches is Expectation Maximization (EM). The Expectation Maximization algorithm is a standard approach for solving the parameters of a mixture model.

In this approach, two alternating steps are performed on the model until convergence (or until a certain number of steps have been performed). The standard form uses observed samples that are assumed to be drawn from some unknown distribution. First, initial guesses of the parameters of this distribution are made, and then the following two steps are repeated:

Expectation step: calculates the probability of the observation given that it was drawn from each of the individual distributions that make up the mixture and given the distribution and mixture parameter estimates.

Maximization step: finds the maximum likelihood estimates of the distribution parameters given the set of observations where the contribution of each sample to each sub-model (e.g., each independent reaction) is based on the probability that the observation originated from that model (as estimated in the Expectation step).

The approach is defined for samples that are drawn from a distribution. However, this approach essentially measures the distribution itself from the negative derivative of the fluorescence. Thus, some embodiments treat the EM problem like having a relative number of reaction "samples" at each temperature. The relative number of "samples" is proportional to the negative derivative of the fluorescence. One caution in this approach is that, because the pseudo-samples are coming from a range of temperatures, these embodiments need to modify the underlying theoretical distribution to account for the fact that they are "drawing" samples from a truncated Van't Hoff distribution, not from a complete Van't Hoff distribution (here the melt-temperature probability distribution is referred to as the Van't Hoff distribution; for example, for a type-2 reaction, the probability density takes the form of equation (17); while this function is only approximately a true density, it can be treated as a probability density, and when examined in a truncated form, it becomes a valid density).

However, EM has some limitations. First, because it is a descent-type algorithm, it can easily converge to a solution that is a local minimum instead of a global minimum. Therefore, EM can be sensitive to the choice of the initial parameters. If these initial parameters are chosen poorly, the global optima may be unreachable. The problem of choosing the initial parameters can be challenging, but a few operations to address this problem can be taken, for example the following:

1. For applications relating to automated genotyping, the embodiments will know a priori the approximate parameters that the embodiments will estimate, given the class of the PCR-generated genetic material. Thus, these embodiments can start their search around the expected parameters.
2. Some embodiments add additional mixture components so that they may more generally fit a broader range of melt curves. This runs the risk of over-fitting the model to the data. However, this risk can be mitigated through the use of regularization terms on the mixture-coefficient estimation or through a reaction-pruning process that tests the effects of eliminating reactions from the mixture model.
3. A non-EM algorithm or a stochastic EM-type algorithm may be used. For example, some embodiments use Markov Chain Monte Carlo to solve this problem.

Second, the maximization step requires the embodiments to know, or be able to reasonably derive, maximum-likelihood estimators. In some cases, like the case of Gaussian mixture models, maximum-likelihood (ML) estimates are easily obtained. However, in some embodiments, the distributions are not in a form that is conducive to ML estimation, at least in closed form. Some embodiments effectively overcome this problem by using optimization packages and using numerical derivatives.

The operational flow for Expectation Maximization may be implemented by a system or a device that executes an EM algorithm. Although an algorithm may be described as performing an operation in this description, the system or device that executes the algorithm executes the operation. After starting, the EM algorithm chooses the initial parameters. After the initial parameters have been determined, the EM algorithm next executes the expectation step (E-step) and then the maximization step (M-step) is performed. Next, the EM algorithm repeats the E-step and M-step until the algorithm converges.

In some embodiments, the expectation step (E-step) calculates the data memberships to each of the mixture-basis classes. That is, at any given temperature, the goal is to calculate how many of the occurring reactions are attributable to each of the underlying independent reactions. The membership to the reaction class k (mixture-basis class k) at a temperature t can be described by the following:

$$w_{t,k} = \frac{\alpha_k p_k(t \mid \Theta_k)}{\sum_{i=1}^{M} \alpha_i p_i(t \mid \Theta_i)}, \quad (20)$$

where $p_k(t|\Theta_k)$ is the truncated Van't Hoff density, which comes from equation (17) but is renormalized so that the function integrates to 1 in the temperature ranges being fit by the model. Also, $$p_k(t \mid \Theta_k) = \frac{p_{VH}(t \mid \Theta_k)}{\int_{T_L}^{T_H} p_{VH}(t \mid \Theta_k) dt}, \text{ and} \quad (21)$$

$$p_k(t \mid \Theta_k) = \frac{p_{VH}(t \mid \Theta_k)}{F_{VH}(T_H \mid \Theta_k) - F_{VH}(T_L \mid \Theta_k)},$$

where $F_{VH}(t|\Theta_k)$ is the cumulative distribution of the non-truncated Van't Hoff density.

The parameters of the distribution $\Theta_k$ include the reaction type and the parameters in the last column of Table 1. In some embodiments of the mixture model, the reaction type is assumed to be fixed, but the parameters and the mixture coefficients $\alpha_i$ are estimated.

In the M-step, the mixture coefficients are calculated (e.g., estimated) to obtain the maximum-likelihood estimates of the reaction functions. There are a few technical challenges that are addressed to accomplish these operations. These challenges are described below.

First, to estimate the mixture coefficients, some embodiments perform a constrained optimization to solve the constrained least squares problem:

$$\min_{x} \|Ax - b\|^2 \quad (22)$$

$$\text{subject to } x_i \geq 0 \text{ for all } i \in \{1, \ldots, M\} \text{ and } \sum_{i=1}^{M} x_i = 1.$$

This unmixing problem can be solved using the Lagrange multiplier theory.

The second challenge is overcoming the generation of the maximum-likelihood estimates of the distribution parameters for each distribution. Typically, ML estimation is based on a set of samples drawn from the distribution of interest. However, here, the melting process generates the fluorescence curve, which essentially measures one minus the cumulative distribution. So to perform ML estimation, some embodiments assume that the number of samples drawn at each sample temperature is proportional to the negative derivative of the fluorescence. With a set of temperatures and negative derivative fluorescence observations $Z = \{(t_j, f_j) : j \in \{1, \ldots, N\}\}$, some embodiments can act as though there are $C \times f_j \times w_{t_j,k}$ samples at each temperature $t_j$ (where C is a constant). And furthermore, these samples can be assumed to be drawn from the truncated model distribution. Thus, the likelihood probability of all of the samples is $$p(Z \mid \Theta_k) = \prod_{j=1}^{N} [p(t_j \mid \Theta_k)]^{Cf_j w_{t_j,k}} \qquad (23)$$

If this is converted to the log likelihood and maximized, it produces the following:

$$\max_{\Theta_k} \log p(Z \mid \Theta_k) = \max_{\Theta_k} \sum_{j=1}^{N} Cf_j w_{t_j,k} \log p(t_j \mid \Theta_k). \qquad (24)$$

Note that this is equivalent to $$\min_{\Theta_k} \sum_{j=1}^{N} f_j w_{t_j,k} \log \frac{f_j w_{t_j,k}}{p(t_j \mid \Theta_k)}, \qquad (25)$$

and this expression is the Kullback-Leibler divergence: $D_{KL}(f \cdot w \| p)$. This is a measure of how well p fits the distribution given by f·w, or more precisely, the measure of information loss when the theoretical distribution is used to approximate the observed data.

The optimization problem in (24) can be solved using gradient-descent-function minimization, which minimizes a continuously-differentiable function. One issue with using this approach is the need for the partial derivatives of the truncated Van't Hoff distribution with respect to the parameters. While the derivatives can be obtained, they are quite long and contain many terms in their expressions. Thus, some embodiments use numerical derivatives at a particular location by evaluating the distribution at a particular parameter setting and then at the same parameter setting plus some small epsilon. Some embodiments arbitrarily use an epsilon of 10e-6 for both melting temperature $T_m$ and total enthalpy change ΔH parameters, and then divide the difference of these two values by epsilon to estimate the derivative.

Additionally, some embodiments run the optimization for a predefined number of iterations or until convergence, but often the algorithm is mostly converged after just a few iterations. So to save time, some embodiments limit the number of iterations to 10. This probably does not cause a problem because this EM process is repeated several times until convergence.

The Van't Hoff Mixture Model advantageously enables a melting curve to be modeled by the summation of a background reaction and a number of DNA reactions—the number of DNA reactions depends upon the number of melting domains involved in the given DNA melt. While the number of melting domains is unknown and depends upon the underlying genotype or the presence/absence of a mutation on the DNA sequence, the information may be derived directly from analysis of the melting curve shape characteristic. However, the accuracy of such an analysis requires the original melt curve to be of sufficient quality. While, variability due to the instrument and DNA characteristics may limit accurate determination of the number of melting domains, using the Van't Hoff Mixture model to model fluorescence does not require determination of the exact number of melting domains. According to invention principles, the background identification algorithm uses an iterative procedure by successively adding DNA melt reactions to the mixture model and estimates associated model parameters, until the mixture model is found to minimize the difference with the original curve at least to a certain defined threshold. This iterative procedure does not require selection of pre- or post-DNA melt regions or thresholds. Though, while not required, the background algorithm may be configured to be applicable to the entire melting curve or a sub-region of the melting curve as manually defined by a user.

The background identification algorithm uses, as input, the negative derivative of the melt curve resulting from melt analysis. In one embodiment, the negative derivative of the melt curve may be calculated using the Savitzky-Golay (SG) filter. Once calculated, the negative derivative melt curve is rescaled so that the maximum fluorescence is set to 1. Thereafter, in one embodiment, the main controller 130 executes the following instructions of the background identification algorithm as shown in FIG. 4. The steps of FIG. 4 are executed iteratively until a determined maximum difference (d) is above a predetermined threshold value indicating that no further DNA melt reactions are likely to be present in the sample being analyzed. In one embodiment, the predetermined threshold value is set to 0.1. In step 402, the background identification algorithm estimates mixture model parameters for the considered number of reactions (n) where n is set equal to 0 in the first iteration of the algorithm. By setting n=0 in the first iteration, the algorithm corresponds to having only the background reaction in the mixture model. In step 404, the algorithm generates the resulting model curve representing n DNA reactions using the model parameter estimates derived in step 402. In step 406, the algorithm determines a difference of the resulting model curve having n DNA reactions from the original melt curve that was used as input to the background identification algorithm. In step 408, the maximum signed difference (d) between the negative derivative curve and the resulting fitted model is calculated as well as associated temperature location (T) where this maximum difference occurs. In step 410, the algorithm determines whether the maximum difference d is below a predetermined distance threshold (e.g. 0.1). If the query in step 410 is positive (YES in 410), the algorithm increments the value of n by a value of 1 (n+1) and identifies an additional reaction at a temperature value T that was used in step 408.

Thus, because the algorithm starts with the number of DNA melt reactions set to zero, the algorithm advantageously includes only the background reaction in the mixture model, and at each repeated steps listed above, n is incremented so that an additional reaction is incorporated into the mixture model. Adding reactions is performed at temperature point where the maximum difference between the mixture model and original curve occurs.

Successive addition of reactions into the mixture model generally induces a rapid decrease of the difference between the mixture model as shown in FIG. 5A and the original curve as can be seen in FIG. 5B. The background algorithm correctly accounts for up to two reactions plus background in the mixture model of FIG. 5A which shows a rapid decrease of the difference between the mixture model and the original curve. This is confirmed by the original melt curve of FIG. 5B which shows two melt domains therein.

Testing on a variety of assays (i.e., small amplicon assay, unlabeled probe assays) showed that the difference of the mixture model and original curve rapidly converges to a value of 0.1. This value is the point that a significant number of DNA reactions for the melt are identified and accounted for in the mixture model. Below this value, it was found that adding more reactions that are irrelevant for the DNA melt since being added to the background component may induce artifacts on the background model. This is especially remarkable on the extremities of the curve where the melt is essentially due to the background melt (i.e., unused primers). This phenomena is illustrated in FIG. 6 which illustrates the results when accounting for between zero DNA melt reactions and four DNA melt reactions in the mixture model. In FIG. 6, the results of the mixture model when accounting for n number of DNA reactions are shown such that each graph shows each resulting reaction (one for the background and n for the DNA) and the residual background curve. Adding DNA reactions induces a decrease of the maximum difference between the model and the original curve. The effect of adding a reaction where the melt is essentially due to the background is illustrated with 4 reactions. Testing on various types of assays and DNA samples revealed that when reaching a maximum difference of 0.1, most of the significant DNA reactions were identified and the resulting background model was found pertinent with respect to the original curve characteristics. FIG. 7 illustrates a single graph including the results of the background model for up to 3 DNA reactions accounted into the mixture model. In this example the background model for 2 reactions is about the same as 3 reactions but significantly better than zero or 1 reaction. Thus, 2 reactions, being the simpler model, is used.

Further confirmation of the advantageous identification and removal of the background reactions is shown in FIG. 8. which illustrates different type of assays and DNA genotypes having the background identified and removed therefrom (e.g. normalized). The iterative steps of the algorithm described in FIG. 4 were applied to the original negative derivative of melt curve ascertained for the particular panels shown in FIG. 8. The examples shown in FIG. 8 are for different assays (COAG small amplicon-type assay and Warfarin unlabeled probe-type assay) and for typical WT/HOM and HET samples as well as Non-Template Control (NTC) melts. The original melting curves are displayed in the graphs on the left while the resulting background-corrected (or normalized) curves are shown in the graphs on the right. The removal of the background allows a person analyzing these curves to focus on only the pertinent parts of the genetic test as it relates to genotyping, the non-pertinent background components being removed from the graphs shown to the user.

In a second embodiment shown in FIG. 9, the background identification algorithm may generate background model data that is modeled using the Van't Hoff equation. In a preprocessing step 902, the background algorithm may receive input from a user to select the pre-DNA($T_1$, $T_2$) or post-DNA ($T_3$, $T_4$) melt regions on a particular melt curve being input and for which background identification is sought. In one embodiment, the input to select the regions may be received via a graphical user interface generated by the background identification algorithm including user selectable image elements enabling input of the values for these regions. In another embodiment, if values for $T_1$, $T_4$ are not defined, the background identification algorithm automatically identifies these values as the start and end points of the melting curve.

In this embodiment, the melting curve data used as input into the algorithm may be any one of an original melting curve or the negative derivative of the original melting curve. No matter the type of melt curve used as input, the respective curve may be smoothed by applying a Savitzky-Golay filter. Additionally, either melting curve used as input may be rescaled so that the maximum fluorescence is set to 1 as discussed above with respect to the first embodiment. The following exemplary implementation of the algorithm uses the negative derivative of a melting curve from the Savitzky-Golay filtering method.

In this embodiment, the algorithm models the background reaction using the Van't Hoff type-1 reaction (shown above) equation shown in Equation 1.

$$f = \frac{1}{1+h} \quad (1)$$
$$h = \exp\left(\frac{HR}{Tm} - \frac{HR}{t}\right)$$

where t is the input temperature to evaluate, Tm is the melt temperature, H is the change in enthalpy and R is the gas law constant. Both H and Tm are the parameters to be estimated. In some embodiments, other reaction models or approximations thereof may be used.

The negative derivative g of the background reaction f is:

$$g = -\frac{df}{dt} = f^2 \cdot \frac{h \cdot HR}{t^2} \quad (2)$$

The estimated negative derivative of the background reaction is defined as equation (3):

$$\hat{g} = \alpha \cdot \hat{f}^2 \cdot \frac{\hat{h} \cdot \hat{H}R}{t^2} \quad (3)$$

where $\alpha$ is the scale factor needed to be estimated also.

To estimate the background reaction, the algorithm analyzes this curve as a non-linear curve regression problem. The algorithm estimates the three parameters ($\alpha$, H, Tm) by minimizing the sum of squared residuals (SSE) of estimated $\hat{g}$ and the given g on a set of $t_i$ where i=1, . . . , n. In other embodiments, other residuals such as the absolute value or even divergence based measures may also be used at this step of the equation.

In response to the user definition of the region to fit the background curve, in step 904, the algorithm introduces a value representing a weight $w_i$ where i=1, . . . , n. For example, if the region R chose by the user is from [$T_1$, $T_2$] and [$T_3$, $T_4$], then w equals to 1 from $w_{T_1}$ to $w_{T_2}$ and from $w_{T_3}$ to $w_{T_4}$, equals to 0 elsewhere. Equation 4 shows the objective function which needs to be minimized using, for example, conjugate gradient descent to perform the minimizing operation in step 906. Using the conjugate gradient descent to perform minimization is described for purposes of example only and other minimization techniques may be used in this embodiment of the background identification algorithm. The gradients may be calculated numerically.

$$J = \sum_i (g_i - \hat{g}_i)^2 w_i \quad (4)$$
$$w_i = \begin{cases} 1 & \text{if } T_1 < i < T_2 \text{ or } T_3 < i < T_4 \\ 0 & \text{else} \end{cases}$$

Once the regression solver approach converges, the algorithm determines, in step 910, whether the estimated background is above the original melting curve on the area $T_2$ to $T_3$. This determination is performed as a check/verification function because the background curve should always be below the melting curve. To account for noise in the melting curve used as input into the algorithm, a noise threshold $\theta$, as shown in Equation 5, is based on the median fitting error from the user specified region. Other measures of $\theta$ are also possible, such as $3\hat{\sigma}$ where $\sigma$ is the sample estimate standard deviation. The noise threshold $\theta$ is calculated in step 908.

$$\theta = 3 \cdot 1.48 \cdot \text{median}(\text{abs}(g_i - \hat{g}_i - \text{median}(g_i - \hat{g}_i))) i \in (T_1, T_2), (T_3, T_4) \quad (5)$$

The maximum difference value between the melting curve and the estimated background curve is illustrated in Equation 6. If val<$-\theta$, the algorithm adds a corresponding data point $T^*$ into the regression process by making the weight $w_{T^*}$ equal to $\lambda$ in step 911. The algorithm reverts back to step 906 and re-estimates the parameters ($\alpha$, H, Tm) by minimizing equation 4 with the updated w. Several choices for $\lambda$ exist. If $\lambda$ is sufficiently large, the regression will tend to pass through the sample point at $T^*$. Some embodiments may place the regression through a point a specified distance under the sample melt curve. In another embodiment, the specified point may be dynamically calculated, for example based on the estimated noise characteristics of the curve. However, if the determination in step 910 is negative indicting that the melt region is not below the background noise, a value for $T_m$ is returned.

$$val = \min(g_i - \hat{g}_i) \; i \in (T_3, T_4) \quad (6)$$

This check/verification process is shown in FIGS. 10A and 10B. FIGS. 10A and 10B illustrate an original melt curve 1001 and an estimated background curve 1002. In FIG. 10A, the initial background estimation shows that portions 1003 of the estimated background curve between $T_2$ and $T_3$ are above the original melt curve. In response to this determination as discussed above, original melt curve 1000, the algorithm accounts for noise and re-estimates the background curve as shown in FIG. 10B whereby the portions 1004 of the background curve 1002 that were above the original curve 1001 in FIG. 10A are now below the original melt curve indicating that the re-estimated background curve in FIG. 10B is more correct than the one shown in FIG. 10A.

Further illustrations of the advantageous results of estimating the background reaction are shown in FIGS. 11A-11D which each illustrate melt characteristics associated with the WARFARIN dataset. Each of FIGS. 11A-11D, the original curve 1101, the estimated background curve 1102 and the normalized curve 1103 having the background curve 1102 subtracted therefrom.

In certain other embodiments, the background identification algorithm may estimate some background model parameters, such as $T_m$ and $\Delta H$, collectively. In one such embodiment, the mean values of $T_m$ and $\Delta H$ are used from multiple channels to obtain a consensus estimate. Median values may also be used for example to obtain more robust estimates. In another example embodiment, $T_m$ and $\Delta H$, $\alpha_1$, $\alpha_2$, ... $\alpha_n$ are estimated simultaneously to fit N curves. This method may also include additionally weighted points in the region from $T_2$ to $T_3$, as described previously which is advantageous because the background may be similar across all channels and, to account for this similarity, better results may be provided.

In one embodiment, to normalize melting curves shown in FIG. 29, a melt region (or non-melt regions) defined by the start and end temperatures $T_1$ and $T_2$ (start and end temperature bars) of the melt region is automatically identified. The goal of the temperature bar placement is to automatically identify non-melt regions of the melting curves which may be fit to background fluorescence models as described in FIG. 9.

FIGS. 29 and 30 demonstrate raw melting curves from a high resolution melt instrument. Most of the curves start with relatively high fluorescence at low temperatures. The fluorescence decreases as the temperature is increased. Part of the fluorescence decrease is due to the DNA denaturing from double stranded to single stranded DNA. The intercalating dye only fluoresces when bound to double stranded DNA. Thus the curves represent profiles of the temperature dependency of the concentrations of double and single stranded DNA. Since the temperature dependency is related to the genetic sequence in the DNA, it is possible to determine subtle changes in a sequence (i.e. a mutation) through the analysis of these melt curves.

Some of the curves in FIGS. 29 and 30 do not represent DNA melting. For example, they may be control samples used to detect any DNA contamination. These curves are shown with much lower fluorescence at low temperatures. In addition to a dependency on concentrations of double stranded and single stranded DNA, the dye also has a temperature dependency whereby the fluorescence of the dye generally decreases with temperature. Methods that allow for removing background from the curves (normalization of the curves) are described above with the reference to FIG. 9. Once normalization is done, one can consider the normalized curves to be predominantly characterized by the relative concentrations of double stranded and single stranded DNA.

FIG. 31 demonstrates negative derivatives of the melting curves shown in FIG. 29. The dashed line shows the mean negative derivative of all of the curves. The peaks in the negative derivative plot indicate the temperatures at which the fluorescence is most sensitive to temperature change. The two large peaks in the curve represent temperature regions of active DNA disassociation. In one embodiment, each curve in FIG. 31 is analyzed according to the algorithm provided in FIG. 21 to identify active melting curves by deselecting the non-active melt curves that fall below the dashed line in FIG. 31. In yet another embodiment, a certain percentage of the curves (by way of example and without limitation, 50 to 75%) which have the highest starting fluorescence values is selected for further analysis. FIG. 32 demonstrates melting curves with the non-active curves removed. The melting curves as demonstrated in FIG. 32 are automatically normalized according to the present invention by identifying the melt region or by identifying the pre and post-melt regions.

Specifically, the start and end temperatures $T_1$ and $T_2$ (see FIG. 29) of the active melt region are iteratively identified by fixing one parameter (i.e. the end melt region temperature) and searching the other, and then vice-versa. FIG. 50 is a flowchart demonstrating a process for automatically determining the start and end temperatures of a melt region in a melting curve. The process starts in step 5005 by initializing the start and end temperatures $T_1$ and $T_2$ of the melt region by selecting $T_1^0$ and $T_2^0$. Specifically, $T_1^0$ and $T_2^0$ can be selected in several ways. In one embodiment, the initial start and end temperatures, $T_1^0$ and $T_2^0$, are selected to be a certain percentage from the start point of the negative derivative curve, $T_{left}$, and the end point of the curve, $T_{right}$. For example, if the curve temperature range is 60° C. ($T_{left}$) to 90° C. ($T_{right}$) and the start and end temperatures of the melt region are picked 10% from the boundaries ($T_{left}$ and $T_{right}$), 63° C. and 87° C. will be chosen as initial start and end temperatures, $T_1^0$ and $T_2^0$, of the melt region. In yet another embodiment, a fixed number of temperature samples is picked from the curve start and end points, $T_{left}$ and $T_{right}$, respectively. Another approach is to pick fixed temperatures from the boundaries ($T_{left}$ and $T_{right}$). For example, if 1° C. is chosen from the boundary, the initial temperatures $T_1^0$ and $T_2^0$ will be at 61° C. and 89° C., respectively.

Next, in step 5010, a first interval $[T_{left}; T_1^*]$ is selected for searching an optimal start temperature and a second interval $[T_2^*; T_{right}]$ is selected for searching an optimal end temperature. In one embodiment, the optimal start temperature of the melt region $T_1$ may be searched in the interval $[T_{left}; T_1^*]$, where $T_1^* = T_{left} + (T_{right} - T_{left})/2$. For example, in the case of melting curves ranging from 60° C. ($T_{left}$) to 90° C. ($T_{right}$), $T_1^* = 75°$ C.

The optimal start temperature should cause the normalized curves (of the active melt curves) to become flat at that starting temperature. Stated another way, the normalized negative derivative at the candidate start temperature should be small in magnitude. In step 5020, the mean negative derivative μ and the standard deviation σ of all of the active melting curves are calculated at each candidate start temperature $T_{1i}$ from the interval $[T_{left}; T_1^*]$ for the melt region defined from $T_{1i}$ to $T_2^k$, where $T_2^k$ is the current candidate end temperature of the melt region and i goes from 1 to n, n being the number of points in a search interval. In one embodiment, $T_{1i} = T_{1(i-1)} + \Delta$ and $T_{2i} = T_{2(i-1)} + \Delta$, where $\Delta$ is a selected incremental value. In step 5015, $T_2^k$ is set as a parameter $P_k$ for calculating the current value of $T_1^k$. The mean derivative μ of all of the active curves at temperature $T_{1i}$ serves as a measure of how good the candidate melt start temperature $T_{1i}$ is. However, the mean negative derivative μ may be misleading because there could be a large variation of the normalized curve slopes and the mean may still coincidently be around zero. Thus, in one embodiment, the standard deviation σ of the negative derivative of all of the melting curves is used at the start temperature $T_{1i}$. In yet another embodiment, the magnitude $|\mu|+2\sigma$ is calculated to determine the optimal start temperature of the melt region with both a low mean μ and a low standard deviation σ. Specifically, the optimal start temperature $T_{1i}$ is determined as the temperature delivering minimum to $|\mu|+2\sigma$.

After determining the current optimal start temperature $T_1^{k+1}$ in step 5025, it is further determined whether $T_1^{k+1}$ converges ($|T_1^{k+1} - T_1^k| < \varepsilon$, where ε is a small non-negative value). If $T_1^{k+1}$ converges, its value is returned as a final $T_1$.

In one embodiment, an additional measure may be the second moment of the negative derivative of the curves. This is akin to the variance of the negative derivatives assuming the true mean is zero. In essence it is a measure of the spread of the negative derivatives at the start temperature around zero.

Next, the algorithm proceeds to step 5035 where the current optimal start temperature $T_1^{k+1}$ determined in step 5025 is fixed as a parameter and the end temperature $T_2^{k+1}$ of the melt region is searched for in the second search interval $[T_2^*; T_{right}]$. In step 5040, the mean negative derivative μ and the standard deviation σ of all of the active melting curves are calculated for each end temperature $T_{2i}$ selected from the interval $[T_2^*; T_{right}]$ for the melt region interval $[T_1^{k+1}; T_{2i}]$, where $T_1^{k+1}$ is the current start temperature of the melt region and i goes from 1 to n, n being the number of points in a search interval. $T_1^{k+1}$ is used as a parameter for calculating the current value of the end temperature $T_2^{k+1}$ in step 5045.

In the current example as shown in FIGS. 33A-C, various melt region start temperatures are tested from 0.5° C. to 15° C. from the minimum temperature $T_1^0 = 60°$ C. in increments of 0.5° C. The mean μ (FIG. 33A), the standard deviation σ (FIG. 33B) of the normalized negative derivatives, and the combination of the two and $|\mu|+2\sigma$ (FIG. 33C) are calculated for each temperature in the interval $[T_{left}; T_1^*] = [60°$ C.; 75° C.]. The optimal start temperature $T_1^{k+1}$ delivering a minimum value to $|\mu|+2\sigma$ is identified in step 5026. In the particular example of FIGS. 33A-C, the measures μ, σ, and $|\mu|+2\sigma$ for the start temperature $T_1$ searched in the interval from 61° C. to 75° C. Ignoring the first 2° C., the minimum of the combined scores $|\mu|+2\sigma$ is at $T_1^1 = 70°$ C.

FIGS. 34A-C show the results of the search for the end temperature $T_2^1$ performed on the second search interval [79° C.; 94° C.] analogously to the search for $T_2^1$ as described above and using $T_1^1 = 70°$ C. as a parameter. The minimum of the combined scores $|\mu|\pm 2\sigma$ is at $T_2^1 = 81.5°$ C.

After determining the current optimal start temperature $T_2^{k+1}$ in step 5045, it is further determined whether $T_2^{k+1}$ converges ($|T_2^{k+1} - T_2^k| < \varepsilon$, where ε is a small non-negative number). If $T_2^{k+1}$ converges, its value is returned as a final $T_2$. If in step 5055 a determination is made that both $T_1$ and $T_2$ have converged or a predefined number of iterations are performed, the algorithm stops, otherwise the process goes to the next iteration to refine the start and end temperatures $T_1$ and $T_2$ by returning to step 5015.

The algorithm repeats steps 5015-5055 to refine the start and end temperatures $T_1$ and $T_2$ while fixing the other previously found temperature as a parameter. This may repeat until the parameters converge or a fixed number of steps is reached. FIGS. 35A-C and FIGS. 36A-C show the result of another iteration following the iteration demonstrated in FIGS. 34A-C and FIGS. 35A-C. Specifically, FIGS. 34A-C and FIGS. 35A-C demonstrate that by repeating the process again with the end temperature $T_2^1$ as a parameter set at 81.5° C., the choice of $T_1^2$ moves to 69.5° C., and that after fixing the start temperature $T_1^2$ to 69.5° C., the next test does not change the end location of 81.5° C. so the algorithm stops.

In yet another embodiment, the temperature search method may employ various implementations such as a grid search as shown in the example above. Other embodiments may follow a line search commonly used in gradient descent methods. Additionally the parameter search may use gradient descent over multiple parameters instead of the coordinate descent described above.

After the process of determining a melt domain is complete, the normalized curves can be examined from the detected start and end melt region temperatures. FIG. 37 shows both active and non-active melting curves after normalization. FIG. 38 shows just the active melt curves. The curves are mostly flat at the beginning and ending of the identified melt domain.

FIG. 39 shows all of the negative derivative curves after normalization. FIG. 40 shows just the active normalized negative derivative curves. The negative derivatives of the active curves are close to zero at the beginning and ending of the melt domain identified. FIG. 41 shows all of the normalized negative derivative curves before rescaling. Since the non-active curves have typically small negative derivatives to begin with, their non-scaled negative derivatives are actually close to zero since the magnitude of their negative derivatives is not exaggerated by rescaling.

This observation leads to an embodiment of the present invention which evaluates the negative derivatives of the non-scaled normalized curves (active and inactive) in the determination of the optimal start and end melt domain temperatures. In this embodiment, non-active curves do not need to be eliminated first in order to estimate the melt domain temperatures.

The current method as described above can be extended to detecting pre and post melt domains (regions). In the example of FIG. 42, some curves are not completely flat at the beginning of the identified melt temperature domain. This may be due to curve anomalies in the 60° C. to 62° C. range. This is highlighted by the oval in FIG. 42. In fact, if this range is excluded from the pre-melt region, the normalization would be better.

If a pre-melt region is defined as being between temperatures $T_1$ and $T_2$ and a post-melt region as being between temperatures $T_3$ and $T_4$, where $T_1<T_2<T_3<T_4$ as shown in FIG. 43, then the melt domain is described as being between $T_2$ and $T_3$.

The method according to the present invention as described in FIG. 50 can be further extended to find pre and post melt domains by searching for the optimal parameters of $T_1$, $T_2$, $T_3$, $T_4$.

In one embodiment, the process may be started by first searching for $T_2$ and $T_3$ and then $T_1$ and $T_4$, $T_2$ and $T_3$ can be found based on the algorithm demonstrated in FIG. 50. Specifically, the process can be started with $T_2$ and $T_3$ being the parameters of the melt domain determined in FIGS. 33-36 as shown above, and then search for $T_2$ from the interval between $T_{left}$ and $T_2$, for example. FIG. 44A-C shows the process as described above with a reference to FIG. 50. Specifically, the minimum of the combined scores $|\mu|+2\sigma$ is at $T_1=69°$ C. Fixing $T_1$, $T_2$, and $T_3$ one can search for an optimal $T_4$ from the interval between $T_3$ and $T_{right}$ for example. As shown in FIG. 45A-C, it is found that the optimal $T_4$ was actually the previous $T_4$ of 90° C. (the maximum temperature).

FIGS. 46-49 demonstrate normalized melting curves and their negative derivatives obtained by using the algorithm of FIG. 50 for automatically determining the melt region. In FIG. 46 the resulting normalized negative derivative melting curves (unsealed) are examined. It is noticed that the negative derivatives at the beginning and ending of the identified melt domain are all near zero. FIG. 47 shows that the active normalized negative derivative curves are all nearly zero at the beginning and ending of the identified melt domain. This is a good indicator of a good normalization. FIG. 48 shows only the active curves of FIG. 47. The results in FIG. 48 take on the appearance of well normalized melt curves. FIG. 49 shows the resulting normalized negative derivative curves for the active melt curves.

In a third embodiment, a background identification algorithm that uses the raw melt curve data is provided. This differs from certain other methods of identifying background reactions which uses filtered melting curves or negative derivative curves as input. While filtering the data is usually advantageous in reducing noise present in the raw data that is due to instrumental and sample variability, it is known that noise reduction is almost always accompanied with local alterations/distortions of the underlying curve shape. This embodiment also does not rely on manual or semi-manual selection of the DNA region of interest (i.e., pre- and post-DNA melt regions) which may be performed using temperature threshold sliders overlapping the displayed melting curves. In a semi-manual selection mode, initial positioning of the sliders may be suggested by an algorithm based on the information derived on the second derivative of the curve which provides information on the local curvature of a curve—convex vs. concave shapes. However, because jittering noise is present in melting curves—even if these curves are filtered to some extent, calculating the second derivative of the melting curves will almost always emphasize that noise. Therefore, curvature information that are only relevant to the DNA characteristics may be difficult to differentiate from the noise component. Using the second derivative of melting curves may provide an approximate location of the DNA melt regions, but are greatly inaccurate. Finally, the choice of positioning the sliders may also impact the estimation of the background melt and thereby the resulting appearance of the normalized melting curves.

Moreover, certain conventional curve normalization processes may depend upon the assay used. It was observed that, for example, background identification/normalization methods optimized for small amplicon assays may fail or are inappropriate when used on unlabeled probe assays. This means that in these existing methods, the underlying model for the background melt is dependent on the DNA sequence being investigated. Such dependency is in fact a demonstration of the great limitation of these methods. Furthermore, conventional methods give an approximation of the background melt and their underlying assumption is that there are actually two different products for the background, instead of one. For example, the method that uses the baseline model for the background provides two different sets of parameters, one set of parameters for the pre-DNA melt background and another set for the post-DNA melt background. Thereby, two models are derived for the background, which means that the background is considered as being two separate different products with different melt characteristics, instead of one background product.

In this embodiment of the background identification algorithm advantageously provides an automated technique for background identification and curve normalization does not need—nor use in any manner, filtered/smoothed melting curves and calculation of any curve derivatives. A further advantage provided by this background identification algorithm is that no a-priori information about the type of assay/DNA sequence being investigated is required. Thus, the background identification algorithm according to invention principles can be used on with any type of sample including, but not limited to small amplicon assays, unlabeled probe assays, scanning assays. Moreover, it is not necessary to know whether a DNA sequence is actually present in the product melt. This embodiment of the background identification algorithm advantageously and uniquely uses raw melting curves acquired by a genetic instrument as input provided that representative portions of the melting curves due to the background must be present on either side of a DNA sequence melt. In other words, as long as the raw melt curve data only reveals information on the background information at the "start" and "end" of the melting curves. A further assumption relied on by this embodiment of the background identification algorithm is that the background melt is invariant/independent (model parameters-wise of the background) whether a DNA sequence melt has occurred or not.

This embodiment performs a series of transformation of the raw fluorescence and determines the optimal transformation such as the transformation resulting in a unique background model independent of whether the background melt is on "starting" or "ending" regions of the melting curve (also referred herein as pre-DNA melt background and post-DNA melt background). The algorithm according to this embodiment is depicted in FIG. 12. In step 1202, a transformation of the raw fluorescence is performed. In step 1204 a step for identifying the background is performed and in step 1210, a step for normalizing the curve is performed.

In step 1202, the transformation of the original melt curve data is performed. The background melt component in a melting curve (herein noted with F(T)) reveals strong characteristics of an exponential function. Therefore, step 1202 transforms the original melt curve data using a log function of the fluorescence of a melting curve or shifted-fluorescence (i.e., F(T)–u with u being a shift factor of the fluorescence) of a melting curve. In doing so, the background melt portion in the melting curve should reveal simple linear characteristic. This exponential background model differs from conventional exponential background models by determining a curve shift factor which allows a single background model over the entire curve.

An example of a raw non-template control (NTC) melting curve which does not contain any DNA and is primary used to detect any potential contamination in the primers/dimers (e.g. a "background" product) and corresponding log fluorescence is shown in FIGS. 13A and 13B. The log of the shifted melting curve reveals a linear trend that is indicative of the 'exponentiality' of the shifted curve background. FIG. 13A illustrates the original melting curve for a NTC sample and corresponding simple log of the shifted fluorescence having a shift factor of +3 is shown in FIG. 13B. FIG. 13 B illustrates that the log of the melting curve reveals a linear trend that is indicative that the shifted curve background can be modeled by a simple exponential function.

According to this embodiment, a shift factor u of the original fluorescence is necessary and should be determined in an optimal manner. The process to determine an optimal shift value will be discussed below. However, the graphs in FIGS. 14A and 14B illustrate why a shift factor is advantageous. When an experiment on the original melt curve data shown in FIG. 14A was performed where a shift factor was sequentially changed, it was observed that almost perfect linearity for the log-transformed curve can be obtained for one value of the shift factor as shown in FIG. 14B. In FIG. 14A, an overview of the experimentation using the melting curve of a NTC is shown and the log of the curve using different shift factors is shown in FIG. 14B such that log shifted fluorescence curve with a shift factor of +5 reveals a better linearity of the log-transformed curve than using other shift factor for the given sample. Here we see that without the shift factor the linearity of the log (or the exponential background assumption) fails.

Turning now to step 1204 of FIG. 12, the condition for the proposed technique is that representative portions of the melting curve due to the background melt must be present on either side of a DNA sequence melt. After log shifting the fluorescence of the melting curve, an automatic detection of the extents of the background melt (using a simple line fit procedure) from the starting point of the curve (step 1206) and from the ending point of the curve (step 1208) are identified separately. On either the "starting" or "ending" side, this automated detection consists in iteratively adding points on the curve, determining the parameters of the line fit and calculating the R-squared ($R^2$), also called the coefficient of determination that provides a measure of how close the curve data are to the fitted line for the considered points of the curve. For each iteration, i.e., addition of points on the curve for the background fit, the following is calculated:

$$R^2 = 1 - \frac{SS_{res}}{SS_{tot}}$$

with $SS_{res} = \sum_i (y_i - f_i)^2$ and $SS_{tot} = \sum_i (y_i - \bar{y})^2$ $y_i$ being a point on the considered extent of the background either from the starting point of the curve or from the ending point of the curve, $f_i$ being the value of the fitted line at the point i, included in the considered extent of the background.

The extent of the background (and thereby the best line fit for the background) is determined by using the maximum value of $R^2$ as shown in FIGS. 15A and 15B when the number of points on the curve (or temperature range) for the background line fit is increased from the starting point of the curve and from the ending point of the curve. The dash lines correspond to the best line fit and thereby the determined optimal background extents on either side of a DNA sample melt. The log shifted melting curve produced from the graph in FIG. 15A is shown in FIG. 15B which shows the log shifted melting curve and background extents that maximize $R^2$.

It is during the background identification step 1204 that the optimal shift factor (u) to be applied on the original fluorescence is determined. At least three values of the shift factor are considered (e.g., −1, 0, and +1). An example of outcomes where five values for the shift factor are used is shown in FIG. 16 for a COAG assay melting curve. For each value, the extent of background melt is determined as described in previous subsection. The slopes of the background melt from the starting point of the curve and from the ending point of the curve are estimated and the ratio of these two slopes provides an indication whether the background on either side is the same or not. In the present algorithm only one model (i.e., one product for the background) should be derived. Thus, the optimal shift value is defined as that resulting to a slope ratio of 1 (i.e., parallel lines for the background on either side). Using a linear regression for modeling the relationship between the resulting ratios of the slopes for the background on either side and the three considered shift factor values, the optimal shift factor corresponding to a slope ratio of 1 is derived. As shown in FIG. 16, background regions prior to the DNA melt and after the DNA melt are modeled with fitted lines of identical slope when the original fluorescence value are shifted with a factor of −4.5462.

Further examples of shift determination using COAG assay and WARFARIN assay data set are shown in FIGS. 17A and 17B, respectively. FIG. 17A shows examples of the slope ratios for the determined background on either side (i.e., from the starting point of the curve, and from the ending point of the curve) using seven shift factor of the original fluorescence of four separated COAG assay samples. For each sample, a linear regression is used to model the relationship between the slope ratio and the considered shift factor, and allows determination of the optimal shift factor, i.e., that corresponding to a slope ratio for the background of 1 where the same background model is used on either side of the melt.

FIG. 17B shows examples of the slope ratios for the determined background on either side (i.e., from the starting point of the curve, and from the ending point of the curve) using seven shift factor of the original fluorescence for four WARFARIN assay samples. For each sample, a linear regression is used to model the relationship between the slope ratio and the considered shift factor, and allows determination of the optimal shift factor, i.e., that corresponding to a slope ratio for the background of 1 where the same background model is used on either side).

Turning back to step 1204 in FIG. 12, the background model parameters are determined using the optimal shift factor u (value corresponding to a ratio of the background slopes equal to 1). The model parameters are determined by repeating step 1204 such that the raw fluorescence is shifted using the optimal value, the resulting shifted fluorescence is then log-transformed, and the background extents and model parameters are determined for each side, i.e., from the starting point of the curve (with $B_1$ for the model background on that side) and from the ending point of the curve (with $B_2$ for the model background on that side). $B_1$ and $B_2$ models are determined to have the same slope value.

$$B_1(T)=sT+t_1 \text{ and } B_2(T)=sT+t_2$$

with $t_1$ and $t_2$ constant variable. FIG. 18 shows an example of the resulting background models for a COAG assay sample, overlapping either the log shifted fluorescence curve, or the original fluorescence curve. In the latter case, the inverse transformation (exponential and a shift of u) is performed for each resulting background models. In FIG. 18, the top graph shows the raw melting curve for the given COAG assay sample, with the resulting inversed-transformed (exponential followed with a shift) background models positioned above and below the raw melt curve using the optimal shift of the raw fluorescence. The middle graph of FIG. 18 shows the log-shifted fluorescence data positioned between the background extents and models. The bottom graph of FIG. 18 shows the normalized melting curve having the background identified by the background identification algorithm removed.

After the competition of step 1204, the algorithm normalizes the resulting estimates of the background models (i.e., $B_1$ and $B_2$) are then subtracted either (1) from the log shifted fluorescence curve or (2) the original fluorescence curve. In the case where the models are subtracted from the log shifted fluorescence curve, the resulting background subtracted curve is then transformed back using an exponential function, followed by a shift back using the u factor determined earlier. In the case where the background models are subtracted from the original fluorescence curve, a transformation with an exponential function is required and is then shifted back with a u factor for each background models $B_1$ and $B_2$. In this situation, the normalized fluorescence is obtained as follows:

$$F_N(T) = \frac{F(T) - (\exp(B_1(T)) + u)}{\exp(B_2(T)) - \exp(B_1(T))}$$

FIG. 19 illustrates various results example of the background identification algorithm according to invention principle which advantageously fully-automates background extent (range) identification and model parameters determination. The background identification algorithm does not require any input from an analyst, nor any manual selection of threshold, nor any a-priori information on the type of assay or other prior knowledge before the background can be identified and removed. Furthermore, as only the raw melting curve is needed, there is no preprocessing required such as the use of a filtering process or any calculation of derivatives. The result is automated background identification including shift-correction of the melting curve in order to verify that the background is only one product melt.

In the third embodiment described above, and in order to reduce the number of iterations necessary to simultaneously define the limits of the background as well as parameters, and determine the optimal shift factor (u), an approximate solution may be employed allowing faster computational determination of the four parameters u, s, $t_1$ and $t_2$. In this approach, the shift u and slope s parameters are solved simultaneously using a gradient descent algorithm such that the residual of the difference between the background curve and the melt curve in the pre- and post-melt regions is minimal. The residual of the log of the curve and a linear function are used to solve the parameter estimation. Likewise, the slope and shift are solved iteratively by fixing one and solving for the other and vice versa.

For this resolution, it is assumed that the pre-DNA melt background ($R_1$) and post-DNA melt background ($R_2$) is defined either manually or automatically through a preliminary additional step. In this approach, a minimum squared error criteria is used. Because of the non-linearity introduced by the log, it is not possible to find a closed form solution for all of the parameters. However, if u is given, a solution for [s, $t_1$, $t_2$] can be determined. Likewise, if [s, $t_1$, $t_2$] is given, then a solution for u can be determined. Therefore, for determination of [s, $t_1$, $t_2$], the following objective function is employed:

$$J(s, t_1, t_2 \mid u) = \sum_{j=1}^{2} \sum_{i \in R_j} \{sT_i + t_j - \log[F(T_i) + u]\}^2$$

It can be shown that this objective function is convex with respect to the parameters s, $t_1$, $t_2$ given u. Thus the minimizer of this is given by the setting the first partial derivatives equal to zero and solving the following system of linear equations:

$$\begin{bmatrix} \sum_{j=1}^{2} \sum_{i \in R_j} T_i^2 & \sum_{i \in R_1} T_i & \sum_{i \in R_2} T_i \\ \sum_{i \in R_1} T_i & N_1 & 0 \\ \sum_{i \in R_2} T_i & 0 & N_2 \end{bmatrix} \cdot \begin{bmatrix} s \\ t_1 \\ t_2 \end{bmatrix} = \begin{bmatrix} \sum_{j=1}^{2} \sum_{i \in R_j} \log[F(T_i) + u] T_i \\ \sum_{i \in R_1} \log[F(T_i) + u] \\ \sum_{i \in R_2} \log[F(T_i) + u] \end{bmatrix}$$

With $N_1$ and $N_2$ being the number of data points in the pre-DNA melt background ($R_1$) and post-DNA melt background ($R_2$), respectively.

For determination of u, the following objective function is used:

$$J(u \mid s, t_1, t_2) = \sum_{j=1}^{2} \sum_{i \in R_j} \{\exp(sT_i + t_j) - [F(T_i) + u]\}^2$$

The objective function is convex with respect to u. The minimum value is found by setting the derivative with respect to u to zero and solving for u.

$$u = \frac{\sum_{j=1}^{2}\sum_{i \in R_j}[\exp(sT_{ij}+t_j)-F(T_{ij})]}{N_1+N_2}$$

Initial values are chosen such as:

$$u = -\frac{1}{2}\left[\min_{i \in R_1 \text{ or } R_2} F(T_i)\right]$$

$$s = 0$$

$$t_1 = \max_{i \in R_1}\log[F(T_i)+u]$$

$$t_2 = \min_{i \in R_2}\log[F(T_i)+u]$$

The two objective functions are then iterated on until convergence. One novel aspect of this approach is the formulation of $J(s,t_1,t_2|u)$ and $J(u|s,t_1,t_2)$. The first objective finds the parameters s, $t_1$, $t_2$ which minimize the squared error of the log of the shifted fluorescence with the linear model. The second however minimizes with respect to u the squared error of the shifted fluorescence with the exponential of the linear model. If the model exactly describes the background these two objectives could both minimize to a zero error in a coordinate descent approach and assuming the descent does not get caught in a local minima, the change in the objective function will not cause any problems. The convenience of this approach is that the updates to the parameters are very simple since and fast they can be provided in closed form. Since there is noise and the model does not always fit the data perfectly however, we have found that the algorithm still converges to a solution in both of the update equations and that this approach provides a fast computational approach that can provide a background model.

In analyzing data from high resolution thermal melting (HRTm), thresholding is used to identify regions of high fluorescence sensitivity for all melting curves in a data set. The user can adjust the threshold bar (horizontal bar as shown in FIG. 26) on the normalized negative derivative graph of a melting curve in order to identity regions of high fluorescence sensitivity. In yet another embodiment, the thresholding process is automated making the usage of the application more reliable, quick and hence user-friendly, especially in case of multiple analyses on the same data by the same or different users.

FIG. 20 is a block diagram demonstrating the steps to perform automated thresholding in the negative derivative plot of a melting curve. Specifically, raw DNA melting data is provided in step 2010. Conversion of the raw data into a smooth and normalized derivative curve is performed in step 2020. The normalized derivative curve represents the variation of fluorescence with respect to change in temperature of reaction related to the DNA disassociation. In order to eliminate insignificant, noisy data from analysis, selection of active curves (discussed in more details below with a reference to FIG. 21) is performed in step 2030. The active curves obtained in step 2030 are used to identify peaks and troughs (discussed in more details below with reference to FIG. 23) in step 2040. Finally, the threshold can be calculated in step 2050 based on the peaks and troughs identified in step 2040.

FIG. 21 is directed to identifying active negative derivative curves (step 2030 of FIG. 20). Normalized negative derivative curves with relatively lower fluorescence values are classified as non-active curves. Non-active curves do not contribute significantly to the melting curve analysis and hence can be removed. In step 2110, the average value of fluorescence negative derivative (−dF/dT) is calculated in each negative derivative melting curve. Then, the average of the averages is estimated to obtain an average fluorescence negative derivative value (AD) for all negative derivative curves. Maximum negative derivative (Max. D) of each negative derivative curve is determined based on normalized melting data. In step 2115, a determination is made for each negative derivative melting curve whether its maximum negative derivative fluorescence value (Max.D) is greater than the average negative derivative fluorescence (AD). If the determination is positive and Max.D is greater than AF, the melting curve is determined to be active in step 2125. Otherwise, the melting curve is determined to be non-active in step 2120. Accordingly, the negative derivative curves whose maximum values are greater than the average are retained as active curves for further analysis. In a non-limiting example, FIG. 22A demonstrates negative derivative curves including both active and non-active curves. FIG. 22B retains only active curves.

The process of identifying all peaks and troughs in a given active negative derivative curve is demonstrated in FIG. 23. Variation in the difference value at peaks and troughs is used to identify a peak or trough. Specifically, in order to identify all the peaks and troughs in a given negative derivative curve as provided in step 2305, the differences between consecutive data points are calculated in step 2310. Specifically, D1 is defined as a difference between current data point and previous data point and D2 is defined as a difference between next data point and current data point. In step 2315 it is determined whether both D1 and D2 are greater (less) than zero. If both D1 and D2 are greater/less than zero, the current point is determined to be neither a peak nor a trough (step 2321). Next, in step 2325, a determination is made whether D1<0 and D2>0. If D1<0 and D2>0, the current point is determined to be a trough in step 2335. Otherwise, the current point is determined to be a peak in step 2330.

Based on all the peaks detected in the process described in FIG. 23, the average peak negative derivative value (AP) is calculated over all curves and used for thresholding in order to identify significant peaks where the fluorescence values are highly sensitive to change in temperature.

FIG. 24 is a flowchart demonstrating a process for valid peak classification. An average peak value (AP) for a plurality of negative derivative curves and peak values (P) of individual curves are calculated in step 2420. Next, a determination is made for each peak whether the peak value (P) is greater than the average peak value (AP). If P>AP, the peak is classified as valid in step 2440. Otherwise, the peak is classified as invalid, step 2430. Adjacent to each valid peak, troughs are identified in step 2450 by identifying the lowest valued point between each consecutive identified peak.

FIG. 25 is a flow chart demonstrating a process for peak threshold calculation according to the present invention. Once valid peak and trough values are obtained according to the processes demonstrated in FIG. 24, the average of the peaks (AP) and the average of the troughs (AT) are calculated in step 2510. In one embodiment, the peak threshold value is calculated as (AP+AT)/2 in step 2520.

Normalized negative derivative curves are demonstrated in FIG. 26. The placement of a threshold bar 2610 is chosen as a particular proportion of the range between the two averages. This value could be determined based on the assay being analyzed. The best position of the threshold bar 2610 is checked for by ensuring that all the valid peaks and troughs detected lie above and below this threshold respectively. For instance, placing the threshold half in between the average peak and average trough value gives good performance with most assays.

Additional embodiments include setting the threshold at a predefined relative distance such as setting it at 26% of the way from average trough to average peak. In other embodiments, the threshold is set as low as possible plus a margin m in this range such that it doesn't create more than M peaks for more than p percent of the curves.

The objective of defining an internal template control (ITC) region is to allow aligning of all the curves in the dataset that allows for better analysis. Defining ITC region involves identifying the temperature regions where ITC reaction peaks occur on the negative derivative graph. These regions denote higher sensitivity of the control denaturing with respect to changes in the temperature. In some high resolution melt (HRM) systems, controls are designed to denature at a temperature higher than the denaturing temperature of the DNA sequence of study.

Internal template control (ITC) shift method is based upon an independent control characterized by a known melting temperature that is included in an amplicon melting reaction. The known melting temperature of the independent control should be outside the range of the amplicon melting temperature. The difference between the known and measured melting temperature of the independent control is then estimated for each channel and differences between the channels are used to adjust the temperatures. In some embodiments, the true melting temperature may be estimated by averaging the measured ITC melting temperatures and the differences of each channel to the mean are used to adjust temperature.

To define the internal template control region, normalized negative derivative of raw melting data is used. The normalized negative derivative graph is obtained using a series of steps of normalization, selection of active curves (FIG. 21), and peak identification (FIG. 23).

FIG. 27 is a flowchart demonstrating a process for ITC region definition. Specifically, temperature values where valid peaks (as identified in FIG. 24) occur across all melting curves negative derivatives are identified in step 2710. Clustering of the temperature values where valid peaks occur results in temperature clusters that define the different regions where peaks occur. Since a peak represents a high change in fluorescence value with respect to variation in temperature, these clusters represent regions of high fluorescence sensitivity. In one embodiment, there are three clusters chosen initially in step 2720. Based on the difference between the cluster centers, as determined in step 2730, and the nature of the assay being analyzed, re-clustering may be done if needed in step 2740. In yet another embodiment, if the difference between the higher valued cluster centers is less than a given value, the temperature values are re-clustered into two clusters, in step 2740. Since the two cluster centers represent the temperature values where the peaks occur, the mid-point between the two clusters (in case of three clusters (step 2750), the two with the higher valued centers (step 2760)) is used as the start temperature for the internal template control region (ITC1). Specifically, for two cluster centers $ITC1=(T_1+T_2)/2$ and for three cluster centers $ITC1=(T_2+T_3)/2$. The end temperature value (ITC2) for the template control region is chosen to be at an equal distance from the higher cluster center as the start value is. For two cluster centers $ITC2=T_2+(T_2-ITC1)$ and for three cluster centers $ITC2=T_3+(T_3-ITC1)$. The ITC template region is therefore decided based on the clustering results. In one embodiment, K-means clustering algorithm is used to perform clustering. FIG. 28 demonstrates normalized negative derivative curves and an internal template control region 2830 defined by vertical bars 2810 and 2820. In this example all DNA samples (and hence all active melting curves) have an identical ITC component added, whereby the ITC component has a known (and consistent) melting temperature.

In one embodiment of the present invention, interactive data analysis involving computational operations over a cloud based web application is provided. Cloud computing is characterized by using a network of remote servers hosted on the Internet to store, manage, and process data, rather than use a local server or a personal computer. While the cloud server is capable of processing client-side changes in analysis configuration parameters, the delay in communication and processing time of handling changes on the server may negatively affect the user's experience. The current invention provides strategies for overcoming the challenge. Additionally, the current invention provides a user interface (UI) design that allows browsers and tablets with limited screen space to actively and intelligently present information to the user.

FIG. 51 demonstrates a system according to the present invention including one or more client computing device(s) (client machine) 5125 that can selectively communicate with a server 5105 over a network 5140. The network 5140 that connects and facilitates communication between the server 5105 and the one or more client computing devices(s) 5125 may be any suitable network. For example, one or more portions of the network 50 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these.

The server 5105 comprises one or more processors 5110, one or more input/output (I/O) interfaces 5120 and storage (memory) 5115. These hardware components of server 5105 communicate by means of one or more buses or other electrical connections 5122. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 5110 include one or more central processing units (CPUs), which include microprocessors (e.g., a single core microprocessor, a multi-core microprocessor); graphics processing units (GPUs); or other electronic circuitry. The one or more processors 5110 are configured to read and perform computer-executable instructions, such as instructions that are stored in the storage 5115. The I/O interfaces 5120 include communication interfaces to input and output devices, which may include a keyboard, a display device, a mouse, a printing device, a touch screen, a light pen, an optical-storage device, a scanner, a microphone, a drive, a controller (e.g., a joystick, a control pad), and a network interface controller. In some embodiments, the I/O interfaces 5120 also include communication interfaces for the server 5105

By way of example, the server 5105 may load instructions from the storage 5115 or another source. During or after execution of the instructions, the processor(s) 5110 may write one or more results (which may be intermediate or final results) to the storage 5115. One or more memory buses 5122 (which may each include an address bus and a data bus) may couple the processor(s) 5110 to the storage 5115. One or more memory management units (MMUs) may reside between the processor(s) 5110 and the storage 5115 and facilitate accesses to the storage 5105 requested by the processor(s) 5110. The storage 5115 may include one or more memories. The memory 5115 may be random access memory (RAM), read only memory (ROM) or a combination of both.

The storage 5115 includes one or more computer-readable storage media. As used herein, a computer-readable storage medium, in contrast to a mere transitory, propagating signal per se, refers to a computer-readable media that includes a tangible article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 5115, which may include both ROM and RAM, can store computer-readable data or computer-executable instructions.

The storage 5115 includes one or more processing modules 5117 that include instructions for controlling various functionality of the server 5105. A module includes logic, computer-readable data, or computer-executable instructions, and may be implemented in software (e.g., Assembly, C, C++, C#, Java, BASIC, Perl, Visual Basic, or any computer programing language), hardware (e.g., customized circuitry), or a combination of software and hardware. In some embodiments, the devices in the system include additional or fewer modules, the modules are combined into fewer modules, or the modules are divided into more modules. When the modules are implemented in software, the software can be stored in the storage 5115. In one embodiment, the data processing module 5117 a set of instructions for processing raw experimental data. In one embodiment, the raw experimental data includes raw DNA melting curves. In this case, instructions for processing raw experimental data include instructions for shifting, normalizing, and clustering melting curves. The normalization of raw DNA melting curves can be performed by using any normalization method according to one or more of the embodiments described herein. In exemplary operation, the raw experimental data may be acquired from (or be provided to the server 5105 by) a source external to server 5105 and stored at a location in the storage 5115. In one embodiment, the external source is the client computing device 5125. In other embodiments, the external source from where the data is acquired may be a cloud storage application whereby an API executed by server 5105 enables access to a location in cloud storage where the raw experimental data is hosted (or stored) and from where the raw experimental data may be downloaded or otherwise acquired. The raw experimental data may be stored as a data object in the storage 5115 and may be used as input by the data processing module 5117. The data processing module 5117 may then generate further processed data that has been processed according to one or more of the algorithms described herein and further stored in a particular location of the storage 5115 for output to the client computing device 5125.

In certain embodiments, a data object may include information that is stored as one or more files in any suitable file type (or format) used by the module or computer executed instructions. The data object is information which may be incorporated in and/or used by one or more of the algorithms described herein and executed by the one or more processors of the server 5105 and/or client computing device 5125. In some embodiments, the data object is processed as an entity distinct from other information or components incorporated in or used by by one or more of the algorithms described herein and executed by the one or more processors of the server 5105 and/or client computing device 5125. The data object may include information grouped together by one or more of the algorithms described herein and executed by the one or more processors of the server 5105 and/or client computing device 5125. A representation of the data object may be presented in a graphical user interface (GUI) as a discrete unit, which may include one or more elements. In some embodiments, the data object may be stored in one or more locations. The data object may include one or more of the following: a data entry, a file, a portion of a file, executable code, an image, or other content.

The client computing device 5125 includes one or more processors 5134, one or more input/output (I/O) interfaces 5137 and storage (memory) 5135. These hardware components of server 5105 communicate by means of one or more buses or other electrical connections 5122. Examples of buses include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 5134 include one or more central processing units (CPUs), which include microprocessors (e.g., a single core microprocessor, a multi-core microprocessor); graphics processing units (GPUs); or other electronic circuitry. The one or more processors 5134 are configured to read and perform computer-executable instructions, such as instructions that are stored in the storage 5135. The I/O interfaces 5137 include communication interfaces to input and output devices, which may include a keyboard, a display device, a mouse, a printing device, a touch screen, a light pen, an optical-storage device, a scanner, a microphone, a drive, a controller (e.g., a joystick, a control pad), and a network interface controller. In some embodiments, the I/O interfaces 5137 also include communication interfaces for the client computing devices 5125. The I/O interfaces further provide interfaces for interacting with and communicating data between the client computing device 5125 and a user interface 5130.

The user interface 5130 includes hardware, software, or both for providing the functionality of the user interface 5130. The user interface 5140 may receive input signals from a user and generate output signals that are displayed by a display device. The display device may be embodied within the user interface 5130 or electrically coupled thereto. The user interface 5130 facilitates interaction between a user and the client computing device 5125 and/or the server 5105.

The user interface 5130 may receive information from an application for processing raw experimental data executing on the server 5130 that controls the operation of the user interface 5130 to implement the functions thereof. In some embodiments, the user interface 5130 enables interaction with a browser application executing on the client computing device 5125 that facilitates connection to the server 5130 via the internet. The browser may be a web browser such as MICROSOFT INTERNET EXPLORER, GOOGLE CHROME or MOZILLA FIREFOX, and may be used to access a resource, such as a web page. The browser may enable a user to display and interact with text, images, form elements, or other information typically located on a web page served by a web server on the World Wide Web or a local area network. The browser may support various types of downloadable, executable, software modules, such as applets or plug-ins. For example, the browser may incorporate a virtual machine configured to execute a program, such as a JAVA applet, embedded in a web page accessed by the browser. The client computing device 5125 may have various add-ons, plug-ins, or other extensions for use in or with the browser.

The information received from the experimental data processing module executing on server 5130 includes data objects defining the structure and type of output to be generated by the user interface 5130. By way of non-limiting example, the experimental raw data module may output data objects representative of elements to be included in a graphical user interface associated with at least one of the functions of module. The user interface 5130 may use these data objects and generate the graphical user interface based on these data objects.

In some embodiments, the user interface 5130 receives input data signals generated by an input/output (I/O) device in order to facilitate the interaction referenced above and described in further detail below. Exemplary I/O devices include but are not limited to keyboards, mouse, touch sensitive displays, microphones, gesture-based input devices and the like.

The user interface 5130 is depicted as external to the client computing device 5130 for purposes of example only and should not be considered limiting in this manner. Skilled artisans will understand that the user interface 5130 may be formed integral with the client computing device 5125 and electrically coupled to the respective components shown therein. In other embodiments, the user interface 5130 may be embodied as a discrete computing device that can be used to connected with the client computing device 5125 such a smartphone or a tablet computing device. In other embodiments, the user interface 5130 may be included in an operation panel that is coupled to the computing device, for example, in a case where the client computing device is a stand-alone device such as thermal melt device as described herein.

The storage 5135 includes one or more computer-readable storage media. As used herein, a computer-readable storage medium, in contrast to a mere transitory, propagating signal per se, refers to a computer-readable media that includes a tangible article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). Also, as used herein, a transitory computer-readable medium refers to a mere transitory, propagating signal per se, and a non-transitory computer-readable medium refers to any computer-readable medium that is not merely a transitory, propagating signal per se. The storage 5135, which may include both ROM and RAM, can store computer-readable data or computer-executable instructions.

The storage 5115 includes one or more processing modules that include instructions for controlling various functionality of the server client computing device 5125 and enables interaction with the server 5105. For example, the storage 5135 may include the browser application described above that allows the user to connect to the server 5105 and which the user may interact with via the user interface 5130. A module includes logic, computer-readable data, or computer-executable instructions, and may be implemented in software (e.g., Assembly, C, C++, C#, Java, BASIC, Perl, Visual Basic, or any computer programing language), hardware (e.g., customized circuitry), or a combination of software and hardware. In some embodiments, the devices in the system include additional or fewer modules, the modules are combined into fewer modules, or the modules are divided into more modules. When the modules are implemented in software, the software can be stored in the storage 5135.

The storage 5135 includes a data object representing a storage reference 5136 comprising the location of raw experimental data obtained from an instrument where DNA amplification and subsequent melting (denaturing) are performed to measure DNA fluorescent signal as a function of temperature. Storage reference 5136 is accessible by the user interface (UI) 5030 as demonstrated in FIG. 52. In one embodiment, as shown in FIG. 52 and FIGS. 55A-E, the UI displays raw fluorescence melting curves (FIG. 55A), normalized fluorescence curves (FIG. 55B), normalized negative derivative curves (FIG. 55C), and fluorescence difference curves (FIG. 55D). In yet another embodiment, the UI displays clustering data and a well plate corresponding to the instrument where the raw melting curves originated from (FIG. 55E). THE UI displays in FIGS. 55A-55E are generated based on data objects received from the experimental raw processing data module executing on the server 5105 and communicated to the client computing device 5125 via the network 5140 based on user interaction and selection with various elements being displayed a given display on the user interface 5130. These data objects are used by the user interface to form displays that provide the desired functionality of the experimental raw data processing module.

In some embodiments, the experimental raw data processing module 5117 executing on the server 5105 provides one or more data objects that enable the user to connect an external storage device to the client computing device 5125 and allows for acquisition of the raw experimental data on which is communicated to the server 5105 and stored in server storage 5115 to allow for respective types of experimental raw data processing to occur at the server 5105. In another embodiment, user interface 5130 enables a user to use the browser application to access a remote location (or application) on the network such as cloud storage application to direct the experimental raw processing data module to access and acquire a set of experimental raw data stored therein and which may be acquired, stored and used by the server 5105 as discussed herein.

The client computing device 5125 may be any computing device having one or more applications or modules that, when executed enable the client computing device to connect to the server 5105 via the network and control the user interface to display one or more display screens that enable a user to make use of the experimental raw processing module executing on the server 5105. This may include, but is not limited to, a desktop computer, a laptop computer, a cellular phone, a smartphone, a tablet computer, a wearable computing device, etc.

FIG. 52 illustrates a workflow in the system of FIG. 51 providing fast data analysis on the web at the expense of reduced resolution of the data. Each element and combination of elements of the workflow described hereinbelow represent one or more set of instructions embodied as the raw experimental data processing module 5117 stored on server 5105. Upon execution thereof, various data objects are communicated via the network to the client computing device and used by one or more applications (e.g. browser application) to render a graphical user interface by the user interface 5130 that allows a user to make use of the various functions provided by the experimental raw processing data module. Powerful server computations are provided by processors 5110 to the user, even if the client computing device 5125 is computationally not very powerful. The data is analyzed by the raw experimental data processing module 5117 at the server 5105 at full resolution. The data processing unit 5117 of the server 5105 comprises instructions for shifting curves (boxes 5228, 5206), resampling curves (box 5208), normalizing curves (box 5214), and clustering curves (box 5224). All instructions in the data processing unit 5117 are executed by the processor(s) 5110. However, to improve graphing responsiveness, fewer points may be chosen to be plotted when displaying curves to the user. In this embodiment, applying the shift on the original curves before resampling greatly simplifies the computation needed for functions such as clustering and curve differencing. Clustering and differencing need the curves to be sampled at the same temperature, but shifting curves individually may cause the curves to be sampled at differing temperatures. Additionally, curve smoothing and derivative calculations use Savitzky-Golay filtering which can be computationally expensive if the curves are not sampled on an even temperature grid. However, if the resample function generates curves at evenly spaced temperatures, the Savitzky-Golay filter may be implemented much more efficiently.

The client computing device 5125 provides a data object representing a plurality of raw experimental curves 5202 to the server 5105 by selecting a data file through the UI 5130. In one embodiment, the raw experimental curves are DNA melting curves obtained on an instrument providing for DNA amplification and melting analysis. Optionally, if ITC button 5232 is activated at the user interface 5130, temperature shifts 5230 obtained by the server 5105 at box 5228 through internal temperature calibration are performed on the raw curves 5202 prior to further processing. Specifically, the plurality of raw curves 5202 together with shift amounts 5230 are provided to the data processing unit 5117 that includes instructions for a shifter 5204. Then, the shifted raw curves 5206 are resampled on evenly spaced temperature increments from the minimum temperature to the maximum temperature by using resampling instructions in the data processing unit 5117, box 5208. While the resampling requires a relatively computationally expensive asynchronous Savitzky-Golay filter to generate the smooth curves 5210, according to the user selection 5260 and negative derivative curves 5212, the workflow only requires this expensive operation to be performed once. The server 5105 provides the smooth melting curves 5210 over the network 5140 to the client computing device 5125 to be displayed in the first graph 5238 through the UI5130.

Next, the resampled smooth curves 5210 and negative derivative curves 5212 are passed to the data processing module 5117 having instructions corresponding to a normalizing unit 5214. The normalizing unit 5214 generates normalized curves 5216 and normalized negative derivative curves 5218 which are provided to the UI 5130 over the network 5140 and displayed in graphs 5242 and 5240, respectively. The normalization method may be defined by the user through the UI 5130, button 5246. In one embodiment, melting region defined by start and end temperatures, $T_1$ and $T_2$ (FIG. 55A), may be determined in a melting curve prior to normalization. The start and end temperatures, $T_1$ and $T_2$, can be determined manually by the user or automatically by applying an algorithm of FIG. 50 by operating a button 5250 of the UI 5130.

Next, the normalized negative derivative curves 5218 may be clustered in several different numbers of clusters by executing corresponding instructions in the data processing module 5117, box 5224. In one embodiment, a determination is made to estimate the optimal number of clusters to be initially shown to the user. Clustering is the process of grouping or categorizing a set of samples that are similar to each other into the same group. When cluster button 5234 is turned on the UI 5130, the clusterings, including cluster IDs 5226, obtained by executing corresponding instructions of the data processing unit 5117 are provided to the client browser (FIGS. 54A-B and FIG. 55E) and the curves are colored according to the clustering.

Graph 5244 on the UI 5130 displays curve differences (FIG. 55D). These differences may be calculated on the server 5105 or the client computing device 5125, box 5220. The baseline curve selection can be done by the user through the user interface by selecting samples to be used in the baseline calculation 5236 as further shown in FIGS. 54A-B. Clusters and individual samples can be selected as baselines for difference curve. In one embodiment, difference curve calculations are performed on the client side instead of the server so that changing the baseline settings is more responsive and doesn't require a call to the server for computation.

FIGS. 53A-B demonstrate a screenshot from the web application according to the present invention displaying curves (FIG. 53A) for different samples shown in an associated well plate (FIG. 53B). In one embodiment, the web application provides a means for users to select the number of clusters. The number of clusters ranges from 1 to n, where n is a natural number. By way of example and without limitations, FIG. 53B indicates that for 96 samples, the number of clusters n is selected to be 10. If the number of samples is less than 10, the number of clusters, n, equals the maximum number of samples. As the user changes the number of clusters, re-clustering needs to be performed on the server. In order to avoid expensive calls to the server, each time the user changes the number of clusters, clustering up to n clusters (including an automated best guess for number of clusters) is pre-calculated at the server 5105 and provided to the client 5125. The pre-calculated cluster data consists of up to n+1 arrays corresponding to each cluster selection. Each array contains a mapping between sample ID and cluster ID identifying which cluster each sample belongs to. The first array corresponds to the best fit clustering result, the second array corresponds to one cluster (where each sample belongs to the same cluster), the third array corresponds to two clusters, and so on and so forth. When the user changes the number of clusters through the UI (FIG. 53B), the client 5125 simply uses the pre-calculated cluster data without having to go back to the server 5105 to recalculate the clustering.

FIGS. 54A-B demonstrate a list of clusters displayed as tree views. Each cluster can be expanded displaying each sample belonging to it (FIG. 54A). In one embodiment, using the UI as shown in FIGS. 54A-B, each sample can be graded with a result selection. Selecting the result at the cluster level sets all samples of the cluster to the selected result. If all samples of a cluster do not have the same result, the cluster result is set as "Mixed". In yet another embodiment, each sample can also be selected to be used as a baseline for use in calculating difference curves (see box 5220 of FIG. 52). Selecting the checkbox at the cluster sets all of its samples as baselines. If not all samples of a cluster are set as a baseline, the cluster checkbox shows a solid checkbox instead of a checked one. In a further embodiment, the UI can also provide an option to remove (or unselect all curves in a particular cluster). For example, some clusters may represent data that is trivial or not interesting to the user. Additionally, when clustering is on, the users can choose to see all of the curves, or just a single curve per cluster that is an average or is the most representative (i.e. a mediod of the cluster).

FIGS. 55A-E demonstrate the UI displaying smooth melt curves, normalized curves, derivative curves, difference curves, and a side panel including clustering data and a well plate having a plurality of samples arranged therein. Each graph can contain a large number of points, many of which may not be needed to appropriately render the curve on the client-side. Sub-sampling can reduce the number of points for each curve that needs to send to the client. Accordingly, performance is improved by decreasing the amount of data to send to the client and decreasing the number of points for a curve the client needs to plot. In one embodiment, all of the data is processed on the server (at full resolutions). However, to improve plotting time, the client sub-samples the data to ensure that no more than N points per plot are drawn.

Sample selection/unselection is only performed in non-clustering mode by selecting samples on the well plate as shown in FIG. 55E. When the user selects/unselects a sample in clustering mode, the mode changes to non-clustering so that any sample selection/unselection won't cause recalculation of clustering results. This allows the user to unselect or select multiple samples without the need for a response from the server. Multiple sample selections/unselections will reflect only on the graphs as shown in FIGS. 55A-D, not the underlying calculation of the clusters (since clustering is turned off). Only when the user turns back on clustering will graph calculations be re-performed with the remaining selected samples. In one embodiment, clustering is performed on all of the samples as a whole and do not consider the selection or unselection of channels when performing clustering. In this embodiment, it is often possible that there are more outlier samples (i.e. bad data or noisy). In this case the maximum number of clusters may be increased (even up to the total number of curves) when pre-calculating the clusterings. By way of example and without limitation, if the user requests for n clusters and all the curves from one cluster were unselected, the client may either reduce the number of clusters to n−1 or increase the clustering level of all of the data so that the selected curves comprise n clusters. Conversely, if the user requested n clusters and the user selects a curve not belonging to the current n clusters at the current clustering level, then the clustering level may be decreased such that n clusters from the selected data are generated.

In this embodiment, selection/unselection of curves does not require recalculation of the clusters on the server thereby improving responsiveness and performance. One benefit of the above approach when used with a large number of curves is the ability to provide a feature which removes outlying samples from the curves selected by providing an option to remove small size clusters and only retain the most populated clusters. In one embodiment, multiple sample selections/unselections may be performed with the click and drag of the mouse.

Experimental data files may contain a large number of samples. In order to facilitate these files without affecting usability, the displayed well plate used for sample selection/unselection as shown in FIG. 55E automatically enlarges when hovering the mouse over it. Furthermore, the side panel (FIG. 55E) can be minimized to display a larger view of the graphs (FIGS. 55A-D) by selecting the close button. The side panel can be opened again by selecting the open button. In one embodiment, during communication with the server, a loading screen is displayed to let the user know that the application is busy.

As demonstrated in FIG. 56, multiple melt files can be dragged and dropped or selected which will open multiple analysis tabs automatically. The web application according to the present invention supports melt files from a variety of vendors. The vendor/instrument name is parsed or inferred from the melt file and displayed to the user as shown in FIGS. 55A-D. In one embodiment, the instrument has a rectangular shaped well plate as illustrated in FIG. 53B and FIG. 55E.

In yet another embodiment demonstrated in FIGS. 57A-B and 58A-B, the well plate is circular. Each circular wedge represents an individual sample well. When clustering is off the wedges are uniquely colored. When clustering is on, the color of the wedges represent the cluster the sample belongs to. Each sample well has a different sample. Gray circular sectors represent empty sample wells. Sample selection with circular plates is implemented with the use of dots to visually represent selected and unselected channels. To select sample wells the user needs to click and hold a wheel wedge and drag the mouse in a clockwise fashion. If the wedge at the location when the mouse button is pushed down is a selected sample, gray dots will appear as the mouse moves signifying which selected sample wedges disabled if the mouse button is released in the current mouse position. as shown in FIG. 57A-B. If the sample at the mouse down position is an unselected wedge, black dots will appear as the mouse moves signifying that the selected wedges will become enabled as shown in FIG. 58A-B. Hollow dots are used to represent disabled wedges that exist within the selection range. Selections always follow the clockwise direction. If the mouse is moved counter-clockwise one wedge before the first selection, then all non-disabled wedges will be selected (same behavior as starting with the first channel and moving the mouse clockwise all the way around to the wedge just before the starting wedge).

In summary, a method and system for interactive data analysis involving a server based application in communication with a client machine is provided. In one embodiment, the server is a cloud server. Specifically, the system comprises a server communicating with a user interface on the client machine over a network. The server has memory including instructions to process raw experimental data received over the network from the client machine. The experimental data is formatted to define an instrument where the raw experimental data originated from. The UI is in communication with the client machine to present processed experimental data to a user, the UI reflecting a type of the instrument. The type of the instrument is characterized by a sample arrangement displayed through the UI.

In one embodiment, the experimental data is DNA raw melting curves measured at a microfluidic instrument. The experimental data is analyzed at the server at full resolution, but fewer points are chosen to be plotted when displaying curves through the UI.

The processing of the melting curves performed on the server includes shifting, normalization, and clustering. The UI presents sample data to the user in an arrangement corresponding to a sample plate design of the instrument. By way of example and without limitation, the sample plate may be rectangular or circular.

An instrument name is parsed or inferred from the raw experimental data and displayed to the user through the UI. Temperature shifts performed through an internal temperature control calibration are performed on the DNA raw melting curves prior to further processing. Furthermore, the server pre-calculates up to a selected number of clusters to present required number of clusters through the UI. The number of clusters is selected through the UI. In one embodiment, the UI allows for selecting/unselecting a sample to be presented to the user.

Furthermore, according to the present invention, a system for analyzing DNA melting curves comprises a microfluidic device having at least one DNA sample therein, a thermal system, and a imaging system. In one embodiment, the at least one DNA sample is in a microchannel of the microfluidic device. The microfluidic device is in communication with a thermal system that is configured to continuously increase the temperature of the at least one DNA sample to cause a DNA melting reaction resulting in denaturing dsDNA to ssDNA. The imaging system is in communication with the microfluidic device to acquire images of the at least one DNA sample. The images are indicative of a fluorescence signal level emitted from the DNA sample. Furthermore, a controller is provided in communication with the thermal system and the imaging system. The controller comprises a memory having a first set of instruction for removing a background signal from the DNA melting curve:

(a) generating a melting curve F(T) for a DNA sample, wherein F is a fluorescence signal indicative of a DNA denaturation process and T is the temperature of the DNA sample.

(b) providing a mathematical model to fit to the melting curve F(T), the mathematical model represented by a sum of a background reaction term and at least one DNA melting reaction term, each DNA melting reaction term being indicative of the DNA denaturation process and the background reaction term being indicative of the background signal;

(c) fitting the mathematical model to the melting curve by calculating model parameters for a model curve;

(d) estimating a maximum difference between the melting curve F(T) and the model curve and a temperature corresponding to the maximum difference;

(e) iteratively adding one DNA melting reaction term at a time to the sum representing the mathematical model and refitting the sum to the melting curve F(T) to recalculate all model parameters in response to the difference between the melting curve and the model curve estimated in step (d) being greater than a threshold, wherein an initial temperature parameter for each newly added DNA melting reaction term equals to the temperature corresponding to the maximum difference between the melting curve and the model curve obtained in step (d);

(f) stopping the iteration process of step (e) when the difference between the melting curve and the model curve is less than the threshold; and (g) subtracting the background reaction term having parameters estimated in the last iteration of step (e) from the melting curve F(T). In one embodiment, the mathematical model to fit to the melting curve F(T) is represented by the formula:

$$F_{total}(T; \Theta) = \sum_{i=1}^{M} \alpha_i F_i(T; \Theta_i) \text{ such that}$$

$$\sum_{i=1}^{M} \alpha_i = 1 \text{ and } \alpha_i \geq 0 \text{ for all } i$$

where T is temperature, $F_{total}(T; \Theta)$ is a total fluorescence, $F_i(T; \Theta_i)$ is a fluorescence of the $i^{th}$ reaction model, $\Theta_i$ is a set of parameters for the $i^{th}$ reaction model, $\alpha_i$ is a coefficient indicative of a contribution of the $i^{th}$ reaction model to the total fluorescence $F_{total}(T; \Theta)$, and $\Theta$ is a collection of all parameters $\{\alpha_i, \theta_i : i \in 1, \ldots, M\}$. $F_i(T; \Theta_i)$ is the fluorescence of the $i^{th}$ DNA melting reaction and is represented by $$F(T) = \frac{4 + h(T) - \sqrt{h^2(T) + 8h(T)}}{4}$$

and the background reaction is represented by $$F(T) = \frac{1}{1 + h(T)}$$

where $$h(T) = \exp\left[\frac{\Delta H}{R}\left(\frac{1}{T_m} - \frac{1}{T}\right)\right],$$

$\Delta H$ is the total enthalpy change, $T_m$ is the melting temperature of the DNA melting reaction, $\theta = \{\Delta H, T_m\}$ is a set of model parameters, and R is the ideal gas law constant.

In yet another aspect of the invention, the controller comprises a second set of instructions for removing a background signal from a DNA melting curve:

(a) generating a melting curve F(T) for a DNA sample, wherein F is a fluorescence signal indicative of a DNA denaturation process and T is the temperature of the DNA sample;

(b) dividing the melting curve into three regions, the three regions being a pre-DNA melt region $[T_1, T_2]$ and a post-DNA melt region $[T_3, T_4]$ corresponding to a background reaction, and a central melt region $[T_2, T_3]$ corresponding to the DNA melting reaction;

(c) fitting a background reaction model to the regions $[T_1, T_2]$ and $[T_3, T_4]$ of the melting curve by determining parameters of the background reaction model and calculating a background reaction curve; and (d) subtracting the background reaction curve from the melting curve F(T) at the temperature interval $[T_1, T_4]$.

In one embodiment, the background reaction model is represented by $$F(T) = \frac{1}{1 + h(T)}$$

$$h(T) = \exp\left[\frac{\Delta H}{R}\left(\frac{1}{T_m} - \frac{1}{T}\right)\right],$$

wherein the total enthalpy change, $\Delta H$, and the melting temperature of the background reaction, $T_m$, are model parameters, and R is the ideal gas law constant. The model parameters $\Delta H$ and $T_m$ are calculated by minimization of an objective function. In one embodiment the objective function is represented by $$J = \sum_i (g_i - \hat{g}_i)^2 w_i$$

$$w_i = \begin{cases} 1 & \text{if } T_1 < i < T_2 \text{ or } T_3 < i < T_4 \\ 0 & \text{else} \end{cases},$$

wherein $g_i$ is a negative derivative of the melting curve F(T), $w_i$ is weight, and $$\hat{g} = \alpha \cdot \hat{F}^2 \cdot \frac{\hat{h} \cdot \overline{\Delta HR}}{T^2}.$$

In yet another aspect of the invention, the controller comprises a third set of instructions for removing a background signal from a DNA melting curve:

(a) generating a melting curve F(T) for a DNA sample, wherein F is a fluorescence signal indicative of a DNA denaturation process and T is the temperature of the DNA sample;

(b) transforming the melting curve F(T) to a curve log(F(T)−u) for different values of a u factor;

(c) for each value of the u factor, fitting a first background model $B_1(T)=s_1T+t_1$ to a pre-DNA melt region $[T_1, T_2]$ of the transformed melting curve log(F(T)−u) and a second background model $B_2(T)=s_2T+t_2$ to a post-DNA melt region $[T_3, T_4]$ of the transformed melting curve log(F(T)−u) thereby determining $s_1$, $s_2$, $t_1$, $t_2$, $T_1$, $T_2$, $T_3$, and $T_4$;

(d) selecting the u factor for which $s_1=s_2$; and (e) removing the background signal from the melting curve F(T) based upon the first and second background models $B_1(T)$ and $B_2(T)$. In one embodiment, step (e) further comprises subtracting $B_1(T)$ and $B_2(T)$ from the log(F(T)−u) curve, transforming the resulting curve back using an exponential function, and subsequently adding the u factor that is determined in step (d). Furthermore, in one embodiment, step (e) further comprises transforming with an exponential function and shifting back with the u factor determined in step (d) each background model $B_1(T)$ and $B_2(T)$ and subtracting the transformed $B_1(T)$ and $B_2(T)$ from the melting curve F(T). In yet another embodiment, step (c) further comprises calculating $T_2$ and $T_3$ by iteratively adding points to each individual fit of the background curves $B_1(T)$ and $B_2(T)$ such that $T_2$ and $T_3$ independently maximize $$R^2 = 1 - \frac{SS_{res}}{SS_{tot}},$$

where $SS_{res}=\Sigma_i(y_i-f_i)^2$, $SS_{tot}=\Sigma_i(y_i-\bar{y})^2$, $y_i=\log(F(T_i)-u)$ on the intervals $[T_1, T_2]$ and $[T_3, T_4]$, $f_i$ is either the fitted line $B_1(T_i)$ or $B_2(T_i)$ at a temperature point $T_i$, $\bar{y}$ is the mean of $y_i$.

In yet another aspect of the invention, the controller comprises a fourth set of instructions for removing a background signal from a DNA melting curve for:

(a) generating a melting curve F(T) for a DNA sample, wherein F is a fluorescence signal indicative of a DNA denaturation process and T is the temperature of the DNA sample;

(b) transforming the melting curve F(T) to a curve log(F(T)−u) for a first approximation of a u factor;

(c) calculating a first background model $B_1(T)=sT+t_1$ for a predefined pre-DNA melt region $[T_1, T_2]$ of the transformed melting curve log(F(T)−u) and a second background model $B_2(T)=sT+t_2$ for a predefined post-DNA melt region $[T_3, T_4]$ of the transformed melting curve log(F(T)−u) by minimizing a first objective function to calculate parameters s, $t_1$, and $t_2$;

(d) taking s, $t_1$, and $t_2$ calculated in step (c) as an approximation to calculate a second approximation of the u factor, the second approximation for the u factor being calculated by minimizing a second objective function;

(e) repeating steps (c) and (d) until the parameters u, $t_1$, and $t_2$, and s converge, wherein u, $t_1$, and $t_2$, and s ultimately minimize the first and second objective functions; and (f) removing the background signal from the curve F(T) based upon the first and second background models $B_1(T)$ and $B_2(T)$.

In one embodiment, step (f) further comprises subtracting $B_1(T)$ and $B_2(T)$ from the transformed melting curve log(F(T)−u), transforming the resulting curve back using an exponential function, shifting the transformed back curve by the u factor determined in step (e). Step (f) further comprises transforming with an exponential function and shifting back with the u factor determined in step (e) each background model $B_1(T)$ and $B_2(T)$ and subtracting the transformed $B_1(T)$ and $B_2(T)$ from the melting curve F(T). In one embodiment, the first objective function is $$J(s, t_1, t_2 | u) = \sum_{j=1}^{2} \sum_{i \in R_j} \{sT_i + t_j - \log[F(T_i) + u]\}^2,$$

and the second objective function is $$J(u | s, t_1, t_2) = \sum_{j=1}^{2} \sum_{i \in R_j} \{\exp(sT_i + t_j) - [F(T_i) + u]\}^2,$$

where $R_1$ is the pre-DNA melt region $[T_1, T_2]$ and $R_2$ is the post-DNA melt region $[T_3, T_4]$.

In yet another aspect of the invention, a system for identifying an internal template control (ITC) region in a melting curve derivative is provided. The system comprises a DNA vessel, a temperature control system, and an imaging system. In one embodiment, the DNA vessel is a microchannel of a microfluidic chip. A plurality of DNA samples undergoing melting analysis in the DNA vessel is provided. Each sample includes an internal template control (ITC) having a pre-determined melt temperature. The DNA vessel is in communication with a temperature control system and an imaging system. The temperature in the plurality of DNA samples is ramped by the temperature control system to achieve DNA denaturing. A controller in communication with the temperature control system and imaging system comprises instructions for: generating a plurality of DNA melting curves for the plurality of samples by using the imaging system to measure fluorescence as a function of temperature; a negative derivative plot is calculated for each generated DNA melting curve; and calculating by start and end temperature values, ITC1 and ITC2, defining an internal template control (ITC) region in the derivative plot of the plurality of DNA melting curves.

In one embodiment, the start and end temperature values, ITC1 and ITC2, defining the internal template control region are calculated by identifying peaks and temperatures corresponding to the peaks in each negative derivative plot. Next, the temperatures corresponding to the peaks are clustered including determining temperature cluster centers. The start and end temperature values are identified for the ITC region based on the temperature cluster centers. In one embodiment, temperatures corresponding to the peaks of the plurality of melting curve derivatives are clustered into three temperature clusters and the start and end temperature values of the ITC region, ITC1 and $ITC_2$, are calculated as follows: $ITC1=(T_2+T_3)/2$ and $ITC2=T_3+(T_3-ITC1)$, wherein $T_1$, $T_2$, and $T_3$ are centers of the first, second, and third clusters, respectively, and $T_3>T_2>T_1$.

In yet another embodiment, the temperatures corresponding to the peaks of the plurality of melting curve derivatives are clustered into three temperature clusters and the start and end temperature values ITC1 and ITC2 are calculated as follows: $ITC1=(T_1+T_2)/2$ and $ITC2=T_2+(T_2-ITC1)$, wherein $T_1$ and $T_2$ are centers of the first and second clusters, respectively, and $T_2>T_1$.

In yet another embodiment, non-active melting curves are removed based on comparing a maximum value of a negative melting curve derivative with an average negative derivative for the plurality of melting curve derivatives. Valid peaks are identified for each melting curve derivative by comparing each peak value to an average peak value for the plurality of melting curve derivatives.

In yet another aspect of the invention, a system for normalizing a plurality of DNA melting curves by determining a melt region in a plurality of DNA melting curves. The system comprises a DNA vessel, a temperature control system, and an imaging system. In one embodiment, the DNA vessel is a microchannel of a microfluidic chip. A plurality of DNA samples undergoing melting analysis in the DNA vessel is provided. The DNA vessel is in communication with a temperature control system and an imaging system. The temperature in the plurality of DNA samples is ramped by the temperature control system to achieve DNA denaturing. A controller in communication with the temperature control system and the imaging system comprises instructions for:

generating a plurality of DNA melting curves for the plurality of samples by using the imaging system to measure fluorescence as a function of temperature;
identifying, start and end temperatures of the melt region in the plurality of melting curves; and
normalizing, by the controller, the plurality of DNA melting curves based at least in part on the identified melt region of the melting curves.

In one embodiment, the start and end temperatures of the melt region in the plurality of melting curves are identified by the controller executing instructions for:

(a) determining a first temperature interval to search for a start temperature of the melt region;
(b) determining a second temperature interval to search for an end temperature of the melt region;
(c) fixing the end temperature and calculating a statistic of a normalized derivative curve at each candidate start temperature from the first search interval;
(d) determining the start temperature based on the statistic calculated in step (c); and
(e) fixing the start temperature obtained in step (d) and calculating the statistic of the normalized derivative curve at each candidate end temperature from the second search interval.

Steps (c)-(e) are optionally repeated until the start and end temperatures converge. In one embodiment, the statistic is based at least in part on a mean and a standard deviation. The start and end temperatures of the melt region deliver the minimum statistic to a combination of the mean $\mu$ and standard deviation $\sigma$ calculated as $|\mu|+2\sigma$. In one embodiment, the initial start and end temperatures are selected to be a certain percentage from start and end points of the melting curve derivatives. Identification and removal of non-active melting curves is based on comparing a maximum value of a negative melting curve derivative with an average negative derivative for the plurality of melting curve derivatives. In yet another embodiment, the controller comprises and executes instructions for: identifying a pre-melt region between temperatures $T_1$ and $T_2$, and a post-melt region between temperatures $T_3$ and $T_4$, where $T_1<T_2<T_3<T_4$, wherein the melt region is between temperatures $T_2$ and $T_3$; determining $T_2$ and $T_3$ according to steps (c)-(f); selecting a search intervals for $T_1$ and $T_4$, respectively; and determining $T_1$ and $T_4$ according to steps (c)-(f) using $T_2$ and $T_3$ as parameters.

In another embodiment, there is provided a system comprising a server including one or more processors and a memory storing at least one set of raw experimental data and instructions that, when executed by the one or more processors, configure the server to process raw experimental data for output processed experimental data, the raw experimental data having a format defining an instrument that generated the raw experimental data; and a client computing device including one or more processors and a memory storing instructions that, when executed by the one or more processors of the client computing device, configure the client computing device to generate a user interface (UI) enabling user interaction with the server via a communications network to obtain the processed experimental data generated by the server and generate the UI reflecting the type of the instrument that generated the raw experimental data.

In a further embodiment, there is provided a method comprising receiving, at a server, raw experimental data from a client machine, the experimental data having a format defining an instrument where the raw experimental data was generated; and processing, at the server, the received raw experimental data to generate processed experimental; obtain, by the client computing device, the processed experimental data; and generating a user interface on the client machine that reflects a type of the instrument that generated the raw experimental data.

In a further embodiment, the system described above can be used in the above method.

In further embodiments, the method described above includes analyzing, at the server, the raw experimental data at full resolution including all data points, and generating the processed data by selecting a subset of data points from the full resolution that are selectively usable by the client computing device to generate one or more plots representative of the processed experimental data in the user interface.

In other embodiments, the raw experimental data includes one or more melt curve data, and the processing of the melting curve data at the server includes one or more of the following: shifting, smoothing, normalization, differentiation, differencing, and clustering. In some embodiments of the system and method described herein, the server may be a cloud server. In some embodiments, the type of instrument is characterized by a sample arrangement displayed through the UI. In another embodiment, the experimental data is DNA raw melting curves. In some embodiments, the UI presents the processed experimental data in an arrangement corresponding to a well plate design used in the instrument that generated the raw experimental data. The sample plate can be of any shape that is known to those of skill in the art, including but not limited to rectangular or circular. In a further embodiment, the instrument name is determined form the raw experimental data and provided to the client machine for display in the UI.

The method can additionally include performing, at the server at least one temperature shift calculated by using an internal template control calibration process on the raw experimental data prior to further processing and/or generating the processed experimental data at the server by pre-calculating up to a selected number of clusters to present required number of clusters through the UI. The method can also include selecting, via the UI at the client machine, a number of clusters that the raw experimental data is to be clustered. Similarly, the method can include selecting a particular sample and associated processed data to be presented to the user and the UI can allow for selecting/unselecting more than one sample simultaneously.

Embodiments also include a server comprising one or more processors; a storage including instructions that, when executed by the one or more processors, configures the server to: receive raw experimental data including format information identifying an instrument that was used to generate the raw experimental data; store the raw experimental data in the storage; generate processed experimental data using the stored raw experimental data including perform one or more processing operations on the raw experimental data using the format information to generate a data object usable to generate a user interface that provides a visual depiction of a sample plate used in the instrument that generated the raw experimental data; and transmit the data object representing the processed experimental data to a client computing device for outputting the user interface generated based on the transmitted data object.

In further embodiments, the server can be used in the methods and/or the systems described above.

In some embodiments, the type of instrument is characterized by a sample arrangement on the sample plate and is included in the format information. In further embodiments, execution of the stored instructions further configures the server to: analyze the raw experimental data at a full resolution including all data points; generate the processed data by selecting a subset of data points from the full resolution that are selectively usable by the client computing device in generating one or more plots representative of the processed experimental data in the user interface. In further embodiments, the execution of the stored instructions further configures the server to perform at least one temperature shift calculated by using an internal template control calibration process on the raw experimental data prior to further processing.

There is also provided a method comprising receiving, at a server, raw experimental data including format information identifying an instrument that was used to generate the raw experimental data; storing the raw experimental data in a storage of the server; generating, at the server, processed experimental data using the stored raw experimental data including perform one or more processing operations on the raw experimental data using the format information to generate a data object usable to generate a user interface that provides a visual depiction of a sample plate used in the instrument that generated the raw experimental data; and transmitting the data object representing the processed experimental data to a client computing device for outputting the user interface generated based on the transmitted data object.

Further, another embodiment provides a computing device comprising one or more processors; a storage including instructions that, when executed by the one or more processors, configures the server to: provide, to a server, raw experimental data including format information identifying an instrument that was used to generate the raw experimental data; receive, from the server, a data object representing processed experimental data that was generated using the stored raw experimental data and which includes processed format information; generating a user interface using the processed format information that provides a visual depiction of a sample plate used in the instrument that generated the raw experimental data; and displaying the generated user interface on a display screen.

A further embodiment provides a computing device comprising one or more processors; a storage including instructions that, when executed by the one or more processors, configures the server to: provide, to a server, raw experimental data including format information identifying an instrument that was used to generate the raw experimental data; receive, from the server, a data object representing processed experimental data that was generated using the stored raw experimental data and which includes processed format information; generating a user interface using the processed format information that provides a visual depiction of a sample plate used in the instrument that generated the raw experimental data; and displaying the generated user interface on a display screen.

A yet further embodiment provides a method comprising providing, by a client computing device to a server, raw experimental data including format information identifying an instrument that was used to generate the raw experimental data; receive, at the client computing device from the server, a data object representing processed experimental data that was generated using the stored raw experimental data and which includes processed format information; generating, by the client computing device, a user interface using the processed format information that provides a visual depiction of a sample plate used in the instrument that generated the raw experimental data; and displaying, at the client computing device, the generated user interface on a display screen.

For the avoidance of doubt, any of the systems, methods, and devices described herein can be utilized with any of the embodiments described herein, whether or not the particular embodiment was specifically described as being applicable.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for removing a background signal from a DNA melting curve on a device having at least one DNA sample and which includes a thermal system in communication with the device, the thermal system being controlled to continuously increase a temperature of the at least one DNA sample to cause a DNA melting reaction resulting in denaturing dsDNA to ssDNA, the method comprising:
    (a) generating, by the device performing the DNA melting reaction, a melting curve F(T) for the at least one DNA sample, wherein F is a fluorescence signal indicative of a DNA denaturation process being performed using the thermal system and T is the temperature of the DNA sample;
    (b) providing a mathematical model to fit to the melting curve F(T), the mathematical model represented by a sum of a background reaction term and at least one DNA melting reaction term, each DNA melting reaction term being indicative of the DNA denaturation process being performed by the device and the background reaction term being indicative of the background signal;
    (c) fitting the mathematical model to the melting curve by calculating model parameters for a model curve;
    (d) estimating a maximum difference between the melting curve F (T) and the model curve and a temperature corresponding to the maximum difference;
    (e) iteratively adding one DNA melting reaction term at a time to the sum representing the mathematical model and refitting the sum to the melting curve F (T) to recalculate all model parameters in response to the difference between the melting curve and the model curve estimated in step (d) being greater than a threshold, wherein an initial temperature parameter for each newly added DNA melting reaction term equals to the temperature corresponding to the maximum difference between the melting curve and the model curve obtained in step (d);
    (f) stopping the iteration process of step (e) when the difference between the melting curve and the model curve is less than the threshold;
    (g) subtracting the background reaction term having parameters estimated in the last iteration of step (e) from the melting curve F(T); and
    (h) outputting the generated melting curve F(T) based on the subtraction in step (g), wherein the generated melting curve output in step (h) includes information associated with DNA melt reactions without the background reaction terms enabling identification of one or more characteristics associated with the at least one DNA sample undergoing the melting reaction.

2. The method of claim 1, wherein the mathematical model to fit to the melting curve F(T) is represented by $$F_{total}(T;\Theta) = \sum_{i=1}^{M} \alpha_i F_i(T;\Theta_i) \text{ such that}$$

$$\sum_{i=1}^{M} \alpha_i = 1 \text{ and } \alpha_i \geq 0 \text{ for all } i$$

where T is temperature, $F_{total}(T;\Theta)$ is a total fluorescence, $F_i(T;\Theta_i)$ is a fluorescence of an $i^{th}$ reaction model of the mathematical model, $\Theta_i$ is a set of parameters for the $i^{th}$ reaction model, $\alpha_i$ is a coefficient indicative of a contribution of the $i^{th}$ reaction model to the total fluorescence $F_{total}(T;\Theta)$, and $\Theta$ is a collection of all parameters $\{\alpha_i, \Theta_i : i \in 1, \ldots, M\}$.

3. The method of claim 2, wherein $F_1(T;\Theta_i)$ is the fluorescence of the $i^{th}$ DNA melting reaction and is represented by $$F(T) = \frac{4 + h(T) - \sqrt{h^2(T) + 8h(T)}}{4}$$

and and the background reaction is represented by $$F(T) = \frac{1}{1 + h(T)}$$

where $$h(T) = \exp\left[\frac{\Delta H}{R}\left(\frac{1}{T_m} - \frac{1}{T}\right)\right],$$

$\Delta H$ is the total enthalpy change, $T_m$ is the melting temperature of the DNA melting reaction, $\Theta = \{\Delta H, T_m\}$ is a set of model parameters, and R is the ideal gas law constant.

4. The method of claim 1, wherein a detection system that detects one or more images is provided and is in communication with the device, and wherein generating the melting curve F(T) includes capturing, by the detection system, one or more images of the DNA sample, wherein the captured one or more images indicate a fluorescence signal level emitted from the DNA sample.

5. The method of claim 1, wherein the device is a microfluidic device.

6. The method of claim 5, wherein the at least one DNA sample is in a microchannel of the microfluidic device.

7. A device that generates a DNA melting curve for at least one DNA sample, the device comprising:
    a thermal system configured to continuously increase a temperature of the at least one DNA sample to cause a DNA melting reaction resulting in denaturing dsDNA to ssDNA; and
    one or more controllers configured to
    (a) generate, by the device performing the DNA melting reaction, a melting curve F(T) for the at least one DNA sample, wherein F is a fluorescence signal indicative of a DNA denaturation process being performed using the thermal system and T is the temperature of the DNA sample;

(b) provide a mathematical model to fit to the melting curve F (T), the mathematical model represented by a sum of a background reaction term and at least one DNA melting reaction term, each DNA melting reaction term being indicative of the DNA denaturation process being performed by the device and the background reaction term being indicative of the background signal;

(c) fit the mathematical model to the melting curve by calculating model parameters for a model curve;

(d) estimate a maximum difference between the melting curve F(T) and the model curve and a temperature corresponding to the maximum difference;

(e) iteratively add one DNA melting reaction term at a time to the sum representing the mathematical model and refitting the sum to the melting curve F(T) to recalculate all model parameters in response to the difference between the melting curve and the model curve estimated in (d) being greater than a threshold, wherein an initial temperature parameter for each newly added DNA melting reaction term equals to the temperature corresponding to the maximum difference between the melting curve and the model curve obtained in step (d);

(f) stop the iteration process of (e) when the difference between the melting curve and the model curve is less than the threshold;

(g) subtract the background reaction term having parameters estimated in the last iteration of step (e) from the melting curve F(T); and (h) output the generated melting curve F(T) based on the subtraction in (g), wherein the generated melting curve output in (h) includes information associated with DNA melt reactions without the background reaction terms enabling identification of one or more characteristics associated with the at least one DNA sample undergoing the melting reaction.

8. The device of claim 7, wherein the mathematical model to fit to the melting curve F(T) is represented by $$F_{total}(T; \Theta) = \sum_{i=1}^{M} \alpha_i F_i(T; \Theta_i) \text{ such that}$$

-continued $$\sum_{i=1}^{M} \alpha_i = 1 \text{ and } \alpha_i \geq 0 \text{ for all } i,$$

where T is temperature, $F_{total}(T; \Theta)$ is a total fluorescence, $F_i(T; \Theta_i)$ is a fluorescence of an $i^{th}$ reaction model of the mathematical model, $\Theta_i$ is a set of parameters for the $i^{th}$ reaction model, $\alpha_i$ is a coefficient indicative of a contribution of the $i^{th}$ reaction model to the total fluorescence $F_{total}(T; \Theta)$, and $\Theta$ is a collection of all parameters $\{\alpha_i, \Theta_i : i \in 1, \ldots, M\}$.

9. The device of claim 8, wherein $F_i(T; \Theta_i)$ is the fluorescence of the $i^{th}$ DNA melting reaction and is represented by $$F(T) = \frac{4 + h(T) - \sqrt{h^2(T) + 8h(T)}}{4},$$

and and the background reaction is represented by $$F(T) = \frac{1}{1 + h(T)}$$

where $h(T) = \exp\left[\frac{\Delta H}{R}\left(\frac{1}{T_m} - \frac{1}{T}\right)\right],$ $\Delta H$ is the total enthalpy change, $T_m$ is the melting temperature of the DNA melting reaction, $\Theta = \{\Delta H, T_m\}$ is a set of model parameters, and R is the ideal gas law constant.

10. The device of claim 7, further comprising a detection system that detects one or more images, and the controller is configured to generate the melting curve F(T) by capturing, by the detection system, one or more images of the DNA sample, wherein the captured one or more images indicate a fluorescence signal level emitted from the DNA sample.

11. The device of claim 7, wherein the device is a microfluidic device.

12. The device of claim 11, wherein the at least one DNA sample is in a microchannel of the microfluidic device.

\* \* \* \* \*